United States Patent
Ferguson et al.

(10) Patent No.: US 9,034,336 B2
(45) Date of Patent: May 19, 2015

(54) IMMUNOMODULATORS AND IMMUNOMODULATOR CONJUGATES

(75) Inventors: David M. Ferguson, St. Paul, MN (US); John Ohlfest, St. Paul, MN (US); Courtney Aldrich, St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 14/342,269

(22) PCT Filed: Aug. 30, 2012

(86) PCT No.: PCT/US2012/053064
§ 371 (c)(1),
(2), (4) Date: Feb. 28, 2014

(87) PCT Pub. No.: WO2013/033345
PCT Pub. Date: Mar. 7, 2013

(65) Prior Publication Data
US 2014/0212442 A1 Jul. 31, 2014

Related U.S. Application Data

(60) Provisional application No. 61/529,090, filed on Aug. 30, 2011.

(51) Int. Cl.
C07D 471/04 (2006.01)
A61K 47/48 (2006.01)

(52) U.S. Cl.
CPC ........ *C07D 471/04* (2013.01); *A61K 47/48238* (2013.01)

(58) Field of Classification Search
None
See application file for complete search history.

(56) References Cited

FOREIGN PATENT DOCUMENTS

WO WO 2006/031878 3/2006

OTHER PUBLICATIONS

Coffman et al., "Vaccine Adjuvants: Putting Innate Immunity to Work", *Immunity*, 33, 492-503 (2010).
Edwards et al., "Toll-like receptor expression in murine expression DC subsets: lack of TLR7 by CD8α+ DC correlates with unresponsiveness to imidazoquinolines", *Eur J Immunol.*, 33, 827-833 (2003).
Gibson et al., "Plasmacytoid dendritic cells produce cytokines and mature in response to the TLR7 agonists, imiquimod and resiquimod", *Cell Immunol.*, 218, 74-86 (2002).
Gill et al., "Use of imiquimod 5% cream (Aldara™) in cats with multicentric squamous cell carcinoma in situ: 12 cases (2002-2005)", *Vet comp Oncol.*, 6, 55-64 (2008).
Ingale et al., "Robust immune responses elicited by a fully synthetic three-component vaccine", *Nat Chem Biol.* 3 (10), 663-667 (2007).
Kastenmuller et al., "Protective T cell immunity in mice following protein-TLR7/8 agonist-conjugate immunization requires aggregation, type I IFN, and multiple DC subsets", *J. Clin. Invest*, 121 (5), 1782-1796 (2011).
Krishnamachari, "Innovative strategies for co-delivering antigens and CpG oligonucleotides", *Adv Drug Deliv Rev.*, 61, 205-217 (2009).
Lu et al., "Treatment Failure of a TLR-7 Agonist Occurs Due to Acute Self-Regulation of Acute Inflammation and Can be Overcome by IL-10 Blockade", *J. Immunol.*, 184, 5360-5367 (2010).
Nierkens et al., "In vivo Colocalization of Antigen and CpG within Dendritic Cells is Assocaited with the Efficacy of Cancer Immunotherapy", *Cancer Res.* 68, 5390-5396 (2008).
Patent Cooperation Treaty, International Searching Authority, Search Report and Written Opinion for PCT/2012/053064, 11 pages, Jan. 3, 2013.
Shi et al., "Discovery of Imidazoquinolines with Toll-Like Receptor 7/8 Independent Cytokine Induction", *ACS Med. Chem. Lett.*, 3, 501-504 (2012).
Wu et al., "Resiquimod: a new immune response modifier with potential as a vaccine adjuvant for th1 immune responses", *Antiviral Res.* 64, 79-83 (2004).

*Primary Examiner* — Janet L Andres
*Assistant Examiner* — Timothy R Rozof
(74) *Attorney, Agent, or Firm* — Viksnins Harris & Padys PLLP

(57) ABSTRACT

The invention provides compounds of formula I: wherein $R_1$-$R_3$, $R_a$, and $R_b$ have any of the values defined herein, and salts thereof. The compounds have immunomodulatory properties.

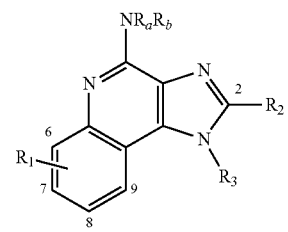

26 Claims, 44 Drawing Sheets

Inflammatory cytokines

BMDC

Inflammatory cytokines

BMDC

Inflammatory cytokines

BMDC

Inflammatory cytokines

Splenocyte

Inflammatory cytokines

Splenocyte

IMMUNOMODULATORS AND IMMUNOMODULATOR CONJUGATES

PRIORITY OF INVENTION

The application claims priority to U.S. Provisional Application No. 61/529,090, filed 30 Aug. 2011. The entire content of this provisional application is hereby incorporated by reference herein.

BACKGROUND OF THE INVENTION

Vaccines contain two components: antigen and adjuvant. The antigen is the molecular structure encoded by the pathogen or tumor against which the immune response is directed. To activate an antigen-specific immune response, the antigen must be presented in the appropriate immunostimulatory microenvironment. Adjuvants establish such microenvironments by stimulating the production of immune-activating molecules such as proinflammatory cytokines. Vaccine efficacy depends on the types of antigen and adjuvant, and how they are administered. Striking the right balance among these components is key to eliciting protective immunity.

Toll-like receptors (TLR) sense infection by recognizing pathogen associated molecular patterns and triggering inflammation. Therefore TLR ligands have been developed as vaccine adjuvants. The uptake of antigen and activation of TLR signaling by adjuvants are dynamic, extremely tenuous processes. Ideally, antigen-presenting cells (APC) that engulf antigen will also take up TLR ligand, resulting in upregulation of co-stimulatory molecules, secretion of inflammatory cytokines, and presentation of antigen to T cells. This is certainly the case when APCs process viral particles, which contain both TLR ligands (e.g., dsRNA) and viral proteins. However, in the case of cancer vaccines the antigen and TLR ligand have been administered in mixture. This approach can result in several theoretical outcomes at the injection site: APCs that engulf antigen alone, TLR ligand alone, or TLR ligand with antigen (the desired outcome). Thus, co-administration can create a problem of signal to noise in the resulting immune response (FIG. 2). Even when antigen and TLR ligand are engulfed by the same APC, the timing is critical. This was best demonstrated by Nierkens et al, who showed that uptake of TLR9 ligand prior to antigen significantly reduced cross presentation of antigen to CTLs relative to concurrent uptake (Nierkens S, et al., *Cancer Res.* 2008; 68:5390-5396). Accordingly, Ingale et al. have demonstrated that direct conjugation of TLR2 ligands to antigen by a covalent bond increased the titer of tumor-reactive IgG over 100,000 times relative to vaccination with a mixture of each component (Ingale S, et al., *Nat Chem Biol.* 2007; 3:663-667). Similarly, coupling antigen to TLR9 ligands increases the number of antigen-specific T cells 5 to 100 fold relative to co-administration of the two components separately (Krishnamachari Y, Salem A K. *Adv Drug Deliv Rev.* 2009; 61:205-217).

Imidazoquinolines are a tricyclic organic molecules that have shown significant potential for use as vaccine adjuvants. Imiquimod (a simple imidazoquinoline) is an FDA-approved immune response modifier administered as a cream on the skin for the treatment of cutaneous tumors. Imiquimod exerts its immunostimulatory effects through TLR 7 expressed on plasmacytoid dendritic cells and B cells in humans. Imiquimod treatment causes release of proinflammatory cytokines including interferonα, interferonγ, and IL-12, all of which are important for priming a robust $T_h1$ immune response associated with anti-tumor and anti-viral activity in animals. Topical imiquimod has been used as a vaccine adjuvant with modest success in numerous studies targeting established tumors and viral infection. However the efficacy of imiquimod is restrained by relying solely on TLR7 signaling because TLR7 is not expressed in one of the most abundant professional APCs, the $CD8\alpha^+TLR7^-$ myeloid dendritic cells (Edwards A D, et al., *Eur J Immunol.* 2003; 33:827-833), thereby limiting efficacy. For this reason other compounds have been developed by modification of imiquimod.

Resiquimod is a potent dual TLR 7 and TLR 8 ligand (Wu J J, et al., *Antiviral Res.* 2004; 64:79-83). Since TLR 8 is expressed in $CD8\alpha^+$ myeloid dendritic cells, it has overcome one of the limitations of imiquimod (Coffman R L, et al., *Immunity;* 33:492-503). Nonetheless, many factors have limited the efficacy of resiquimod and imiquimod. One recently identified mechanism for treatment failure is that although these drugs induce proinflammatory cytokines, they concurrently induce high levels of anti-inflammatory cytokines such as IL-10 (Gibson S J, et al., *Cell Immunol.* 2002; 218:74-86; and Lu H, et al., *J Immunol;* 184:5360-5367). Of clinical relevance, application of imiquimod cream works on the treated tumor, but not distal tumors, suggesting an impairment in systemic immunity (Lu H, et al., *J Immunol;* 184: 5360-5367; and Gill V L, et al., *Vet Comp Oncol.* 2008; 6:55-64). Indeed blockade of IL-10 following imiquimod treatment was shown to result in control of treated and distal (untreated) tumors, demonstrating the clinical significance of the self-regulating cytokine response induced by currently used Imidazoquinolines. Thus, a need exists to develop novel imquidazolequinoline-based compounds that trigger a more desirable ratio of pro- to anti-inflammatory cytokines.

An analysis of recent work in the field shows that triggering multiple receptors and/or alternative pathways is typically better for immune stimulation and, the triggering additional receptors might shift the cytokine prolife to a more desirable one. Since imiquimod (exclusive TLR7 ligand) and resiquimod (dual TLR7/8) ligands prime limited immunity, it would be desirable to develop improved compounds that tap additional receptors. Finally, studies have indicated dual TLR7/8 agonists are suboptimally immunogenic unless they are directly conjugated to antigen (Kastenmuller K, et al., *J Clin Invest;* 121:1782-1796); thus new compounds that are amenable to conjugation should also be developed.

SUMMARY OF THE INVENTION

Imquidazolequinoline-based compounds that trigger a more desirable ratio of pro- to anti-inflammatory cytokines have been discovered. Accordingly there is provided a compound of the invention which is a compound of formula I:

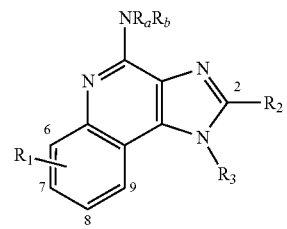

wherein:
$R_1$ is $R^k$—O—C(=O)—;
$R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl, optionally substituted with one or more hydroxy, halo, oxiranyl, $(C_3-C_8)$cycloalkyl, aryl, $(C_1-C_6)$alkoxy, $(C_1-C_6)$alkylthio, or $NR^gR^h$;

$R_3$ is $(C_1-C_6)$alkyl, optionally substituted with one or more hydroxy, aryl, $(C_1-C_6)$alkoxy, or oxiranyl;

$R_a$ is H or $(C_1-C_6)$alkyl;

$R_b$ is H or X—Y;

$R^g$ and $R^h$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;

$R^m$ and $R^n$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

X is a linking group; and

Y is an antigen or maleimide;

wherein the tricyclic ring structure in formula I can optionally be further substituted on one or more carbons with one or more groups independently selected from halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and $R^p$ and $R^q$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

or a salt thereof.

The invention also provides a pharmaceutical composition comprising a compound of formula I, or a pharmaceutically acceptable salt thereof, and a pharmaceutically acceptable diluent or carrier.

The invention also provides a method for treating a pathological condition (e.g. a viral infection, a bacterial infection or cancer) in an animal comprising administering a compound of formula I, or a pharmaceutically acceptable salt thereof, to the animal.

The invention also provides a method for stimulating an immune response in an animal comprising administering a compound of formula I, or a pharmaceutically acceptable salt thereof, to the animal.

The invention provides a compound of formula I or a pharmaceutically acceptable salt thereof for use in the prophylactic or therapeutic treatment of a pathological condition (e.g. a viral infection, a bacterial infection or cancer) in an animal.

The invention provides a compound of formula I or a pharmaceutically acceptable salt thereof for use in medical therapy.

The invention provides the use of a compound of formula I or a pharmaceutically acceptable salt thereof for the manufacture of a medicament useful for the treatment of a pathological condition (e.g. a viral infection, a bacterial infection or cancer) in an animal.

The invention also provides processes and intermediates disclosed herein that are useful for preparing compounds of formula (I) or salts thereof.

The presence of the ester group ($R_1$) at C-7 unexpectedly provided compounds that activate inflammatory cytokine response even in the absence of TLR7 or TLR8 agonist activity. The compounds of the invention are the first compounds for which this has been reported. Additionally, the type of cytokine (IL-1β) triggered by the compounds of the invention demonstrates that they activate the inflammasome which other known TLR7/8 agonists are poor at doing. IL-1β is clinically important because it serves as a unique signal for the activation of CD4 T cells. (Curtsinger J M, Mescher M F, *Curr Opin Immunol*, 2010, 22, 333-40.) By optimally activating CD4 T cells, one can increase the antibody response and/or CD8 T cell response, which is important in vaccines for the prevention of infection and the treatment of tumors, for instance. The unique IL-1β signature of certain compounds of the invention is thus expected to give them improved ability to combat infection and better treat diseases such as cancer.

DETAILED DESCRIPTION

Figure 1:
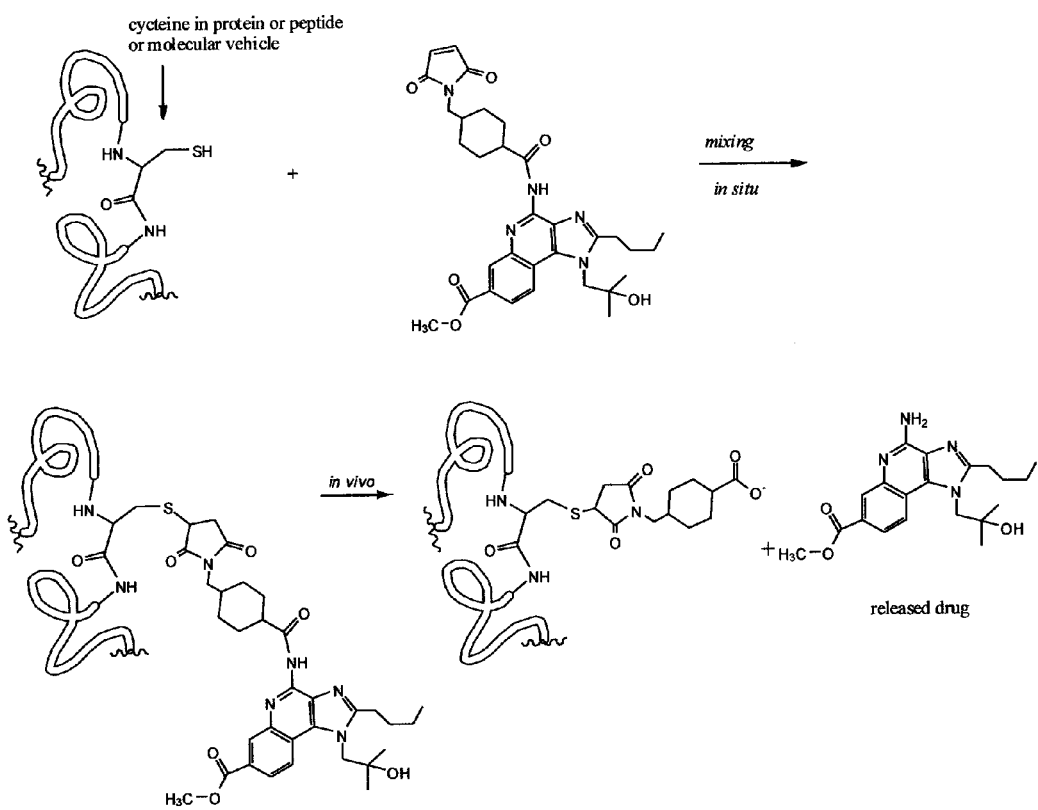
FIG. 1 Illustrates a process by which a drug pharmacophore is carried into the target cell or tissue or bio-compartment. The maleimide containing drug reagent is conjugated to the biomolecule via simple mixing forming a covalent complex. The biomolecule carries the pharmacophore to the target cell or biological target where it is released in the active form by hydrolysis.
Figure 2:
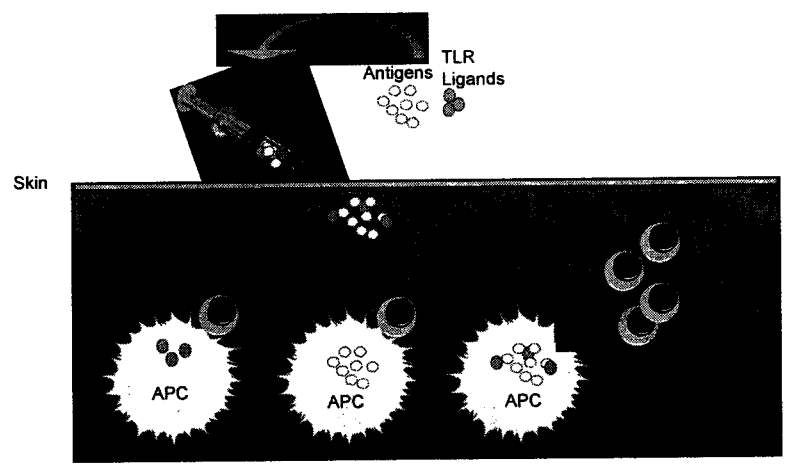
FIG. 2 Illustrates what is known about co-injection of tumor-antigens and toll like receptor (TLR) ligands as vaccine adjuvant into the skin. Antigen presenting cells (APCs) engulf debris at the injection site and migrate to the draining lymph nodes to present antigen. APCs that engulf TLR ligand alone do not present tumor antigen, promoting immunological ignorance. APCs that engulf antigen without a concomitant danger signal in the form of TLR ligand do not adequately activate T cells, resulting in tolerance to the tumor antigen. APCs that become activated by TLR ligand while engulfing antigen upregulate the necessary inflammatory gene expression program to elicit expansion of tumor-reactive T cells.
Figure 3:
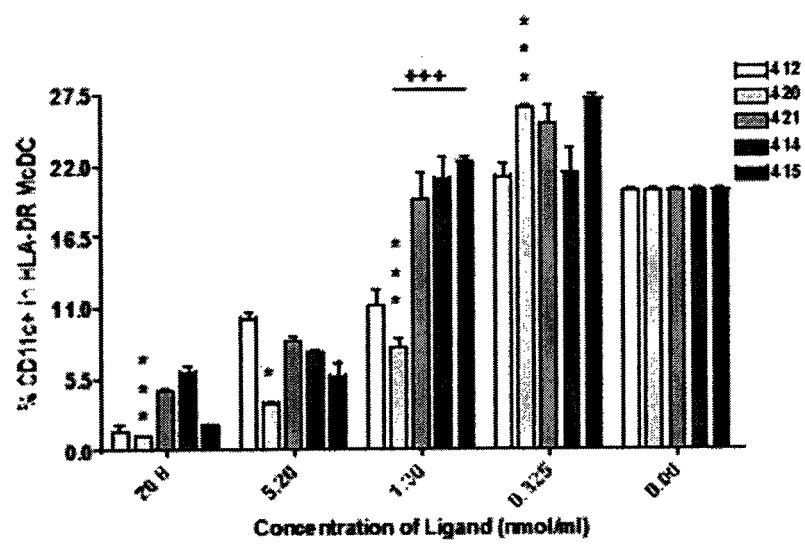
FIGS. 3-15 show results from Example 5.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Specific Embodiments

In one specific embodiment $R_2$ is H, $NR^gR^h$, $(C_1-C_6)$alkanoyl, $(C_1-C_6)$alkoxycarbonyl, $(C_1-C_6)$alkanoyloxy, $R'''R''NC(=O)$—, or $(C_1-C_6)$alkyl, optionally substituted with one or more hydroxy, halo, oxiranyl, $(C_3-C_8)$cycloalkyl, aryl, $(C_1-C_6)$alkoxy, or $NR^gR^h$.

In one specific embodiment $R_1$ is methoxycarbonyl, ethoxycarbonyl, isopropoxycarbonyl, benzyloxycarbonyl, and butoxycarbonyl.

In one specific embodiment $R_1$ is methoxycarbonyl.

In one specific embodiment $R_2$ is $NR^gR^h$, $(C_1-C_6)$alkanoyl, $(C_1-C_6)$alkoxycarbonyl, $(C_1-C_6)$alkanoyloxy, $R'''R''NC(=O)$—, or $(C_1-C_6)$alkyl, optionally substituted with one or more hydroxy, halo, oxiranyl, $(C_3-C_8)$cycloalkyl, aryl, $(C_1-C_6)$alkoxy, oxiranyl, or $NR^gR^h$.

In one specific embodiment $R_2$ is $(C_1-C_6)$alkyl, optionally substituted with one or more hydroxy, halo, oxiranyl, $(C_3-C_8)$cycloalkyl, aryl, $(C_1-C_6)$alkoxy, oxiranyl, or $NR^gR^h$.

In one specific embodiment $R_2$ is $(C_1-C_6)$alkyl, optionally substituted with one or more hydroxy, oxiranyl, or $(C_1-C_6)$alkoxy.

In one specific embodiment $R_2$ is $(C_1-C_6)$alkyl, substituted with one or more hydroxy.

In one specific embodiment $R_2$ is H, methyl, ethyl, propyl, butyl, or pentyl.

In one specific embodiment $R_2$ is H, methyl, ethyl, or propyl.

In one specific embodiment $R_3$ is $(C_1-C_6)$alkyl, substituted with one or more hydroxy.

In one specific embodiment $R_3$ is isobutyl, benzyl, 2-hydroxy-2-methylpropyl, 2-hydroxypropyl, 2-hydroxyethyl, 2-methoxyethyl, or 2-benzyloxyethyl.

In one specific embodiment $R_3$ is isobutyl, benzyl, 2-hydroxy-2-methylpropyl, 2-hydroxypropyl, 2-hydroxyethyl, or 2-benzyloxyethyl.

In one specific embodiment $R_b$ is H.

In one specific embodiment $R_b$ is X—Y.

In one specific embodiment X is $(C_1-C_6)$alkyl, $(C_2-C_6)$alkenyl, or $(C_1-C_6)$alkynyl, which $(C_1-C_6)$alkyl, $(C_2-C_6)$alkenyl, or $(C_1-C_6)$alkynyl is optionally substituted with oxo.

In one specific embodiment Y is maleimide.

In one specific embodiment Y is an antigen associated with a bacteria or virus.

In one specific embodiment Y is an antigen associated with a an influenza, HIV, or HCV.

In one specific embodiment Y is an antigen associated with a tumor cell or a tumor cell lysate.
In one specific embodiment Y is an antigen that comprises a peptide sequence containing cysteine or lysine.
In one specific embodiment the compound is selected from:
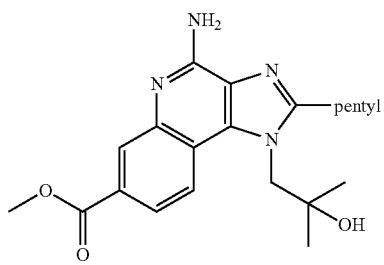
527
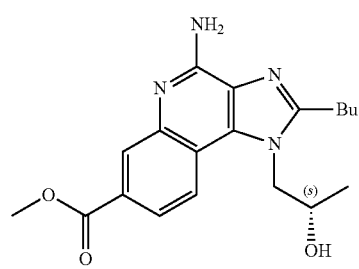
528
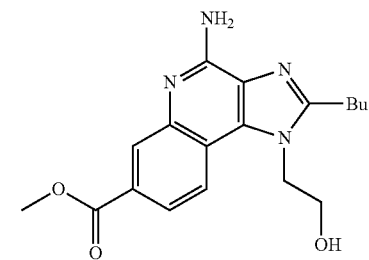
529
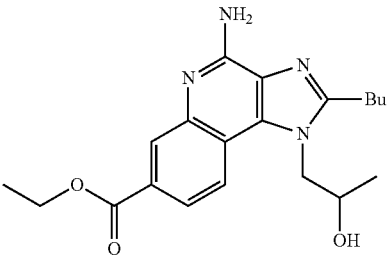
531
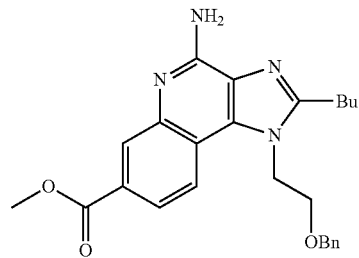
520
-continued
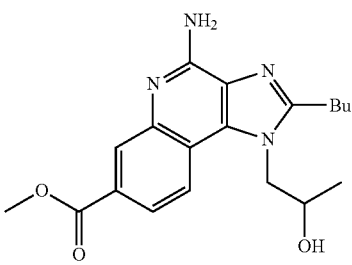
522
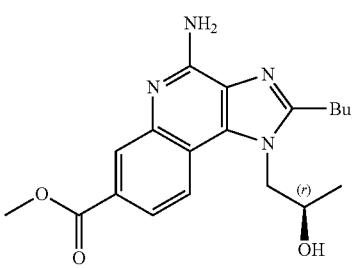
533
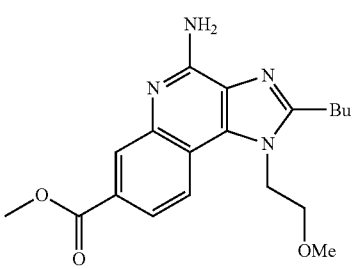
521
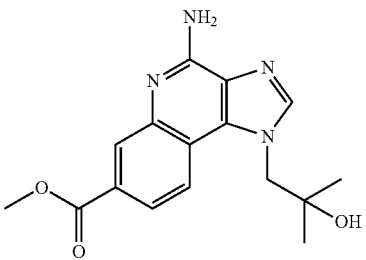
421
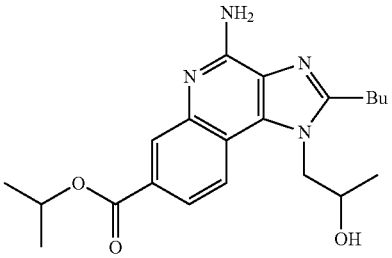
530
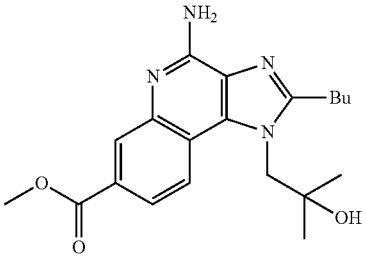
420

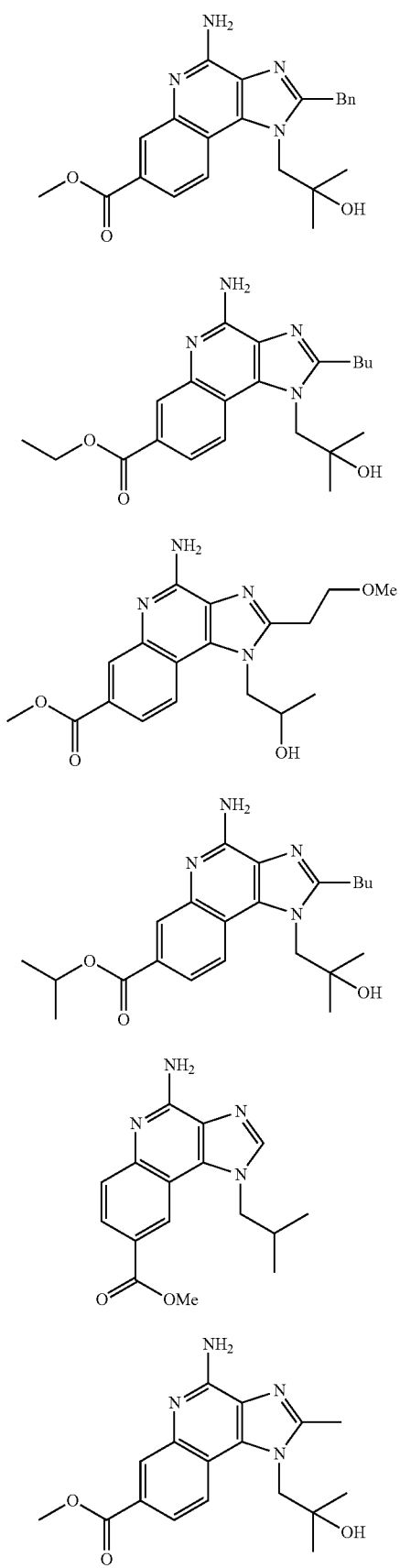
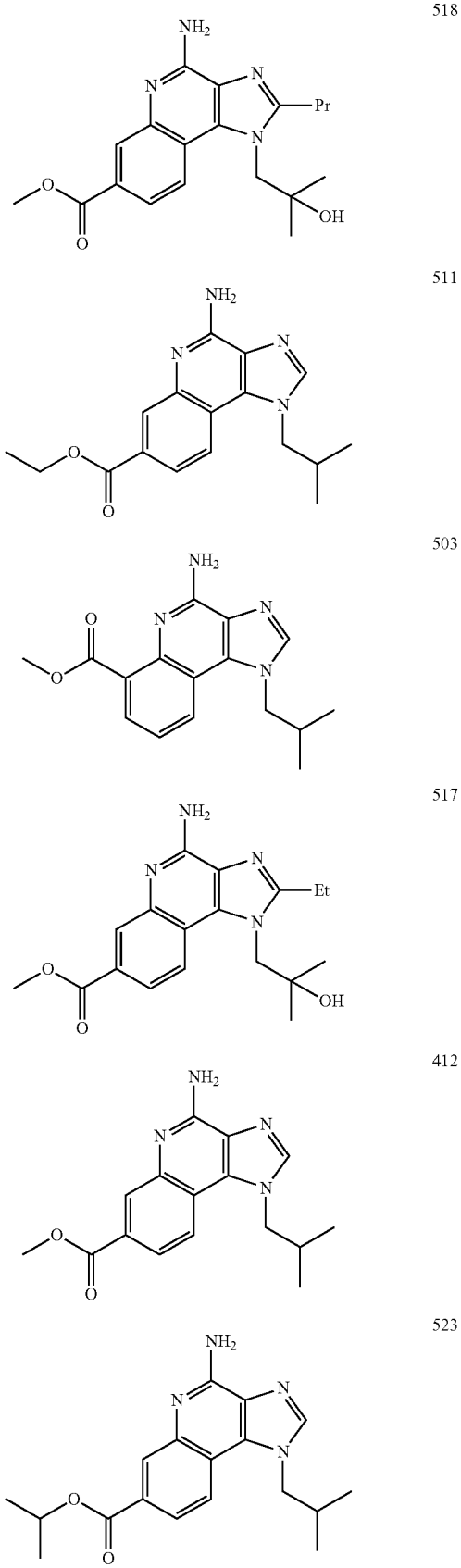

-continued

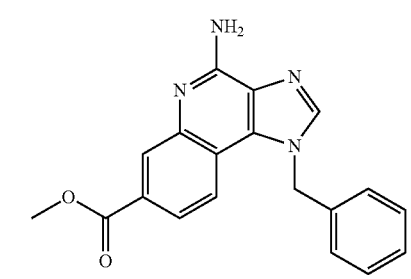
514

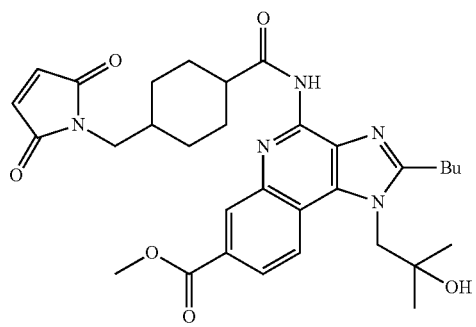
550

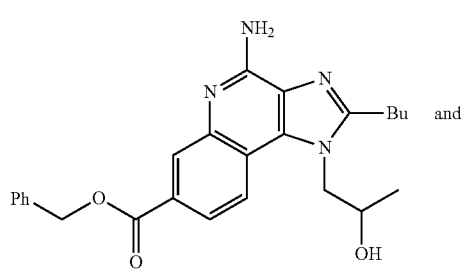
538

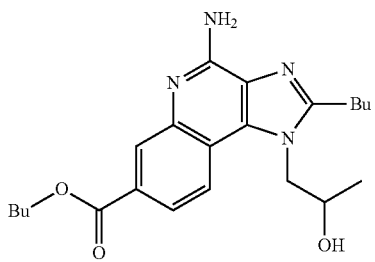 and
540 and salts thereof.

In one specific embodiment:

$R_1$ is $R^k$—O—C(=O)—;

$R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl, optionally substituted with one or more hydroxy, —SH, halo, oxiranyl, $(C_3-C_8)$cycloalkyl, aryl, $(C_1-C_6)$alkoxy, $(C_1-C_6)$alkylthio, or $NR^gR^h$;

$R_3$ is $(C_1-C_6)$alkyl, optionally substituted with one or more hydroxy, aryl, or oxiranyl;

$R^a$ is H or $(C_1-C_6)$alkyl;

$R^b$ is H or X—Y;

$R^g$ and $R^h$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

$R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;

$R^m$ and $R^n$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

X is a linking group; and

Y is an antigen or maleimide;

wherein the tricyclic ring structure in formula I can optionally be further substituted on one or more carbons with one or more groups independently selected from halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and $R^p$ and $R^q$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl.

In one specific embodiment the compound of formula (I) is a compound of formula (Ia):

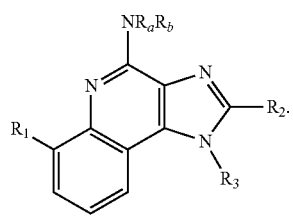
(Ia)

In one specific embodiment the compound of formula (I) is a compound of formula (Ib):

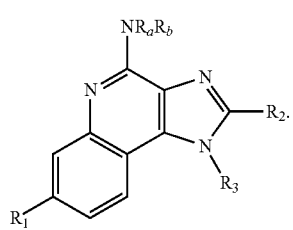
(Ib)

In one specific embodiment the compound of formula (I) is a compound of formula (Ic):

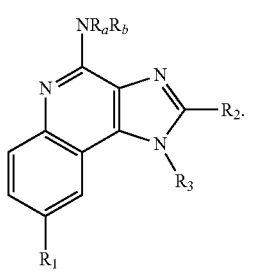
(Ic)

In one specific embodiment the compound of formula (I) is a compound of formula (Id):

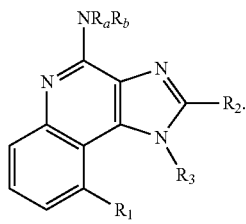

Linking Group X

In certain embodiments of the invention X is a linking group that joins the remainder of the compound of formula I to an antigen or to a maleimide. Compounds wherein Y is a maleimide are useful as intermediates for preparing compounds wherein Y is an antigen. The nature of the linking group X is not critical provided the resulting antigen conjugate retains the useful biological propertied described herein.

In one embodiment of the invention the linker has a molecular weight of from about 20 daltons to about 20,000 daltons.

In one embodiment of the invention the linker has a molecular weight of from about 20 daltons to about 5,000 daltons.

In one embodiment of the invention the linker has a molecular weight of from about 20 daltons to about 1,000 daltons.

In one embodiment of the invention the linker has a molecular weight of from about 20 daltons to about 200 daltons.

In another embodiment of the invention the linker has a length of about 5 angstroms to about 60 angstroms.

In another embodiment of the invention the linker separates the antigen from the remainder of the compound of formula I by about 5 angstroms to about 40 angstroms, inclusive, in length.

In another embodiment of the invention the linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment of the invention the linker comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the linker is a divalent radical formed from a protein.

In another embodiment of the invention the linker is a divalent radical formed from a peptide.

In another embodiment of the invention the linker is a divalent radical formed from an amino acid.

In another embodiment the linker is:

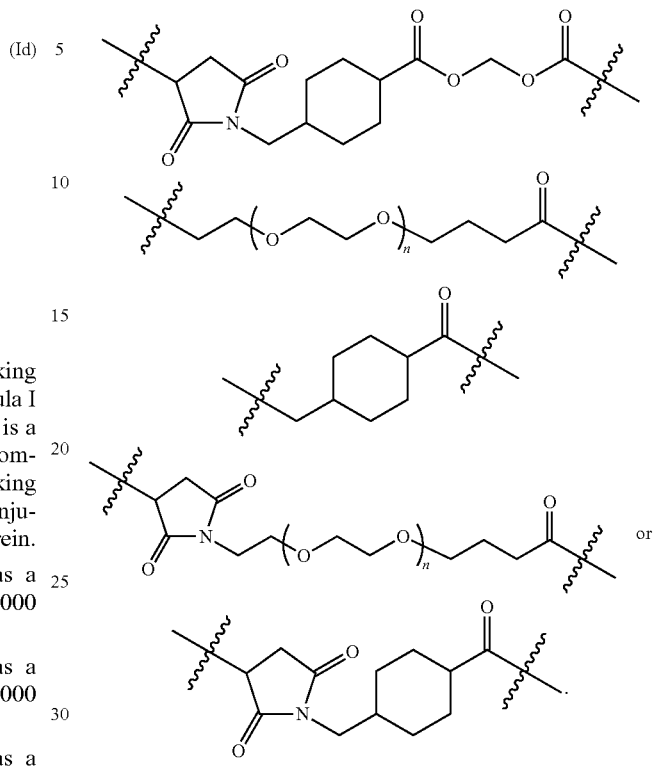

In another embodiment of the invention the linker is:

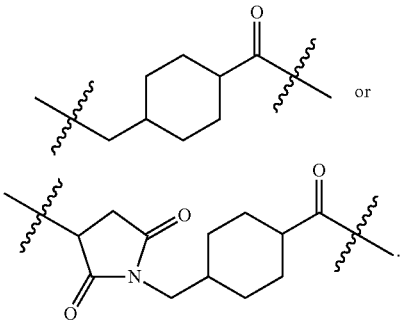

Antigen

An "antigen" as used herein includes any substance that causes the immune system to produce antibodies or antigen-specific T cells against the substance. The term also includes haptans. An antigen may be a foreign substance from the environment such as a chemical, bacteria, virus, or pollen. An antigen may also be formed within the body such as with bacterial toxins, tissue cells, or tumor cells. The antigen is the molecular structure encoded by the substance such as the pathogen or tumor against which the immune response is directed. Examples of antigens may come from pathogens such as bacteria or viruses (e.g. influenza, HIV, or HCV) Alternatively, the antigen may come from a tumor cell or a tumor cell lysate or synthetic peptides derived from tumors or infectious organisms. In one embodiment the antigen comprises a peptide sequence containing cysteine or lysine.

Processes for preparing compounds of formula I are provided as further embodiments of the invention and are illustrated by the following procedures in which the meanings of the generic radicals are as given above unless otherwise qualified. Certain compounds of formula I are useful as intermediates for preparing other compounds of formula I.

As shown in the data provided in the Examples below, representative compounds wherein $R_1$ is $R^k$—O—C(=O)— have been found to possess a unique and beneficial cytokine profile. Accordingly, compounds wherein $R_1$ is $R^k$—O—C(=O)— may be particularly useful in the methods of the invention.

A compound of formula I can be prepared as illustrated in Schemes 1 and 2.

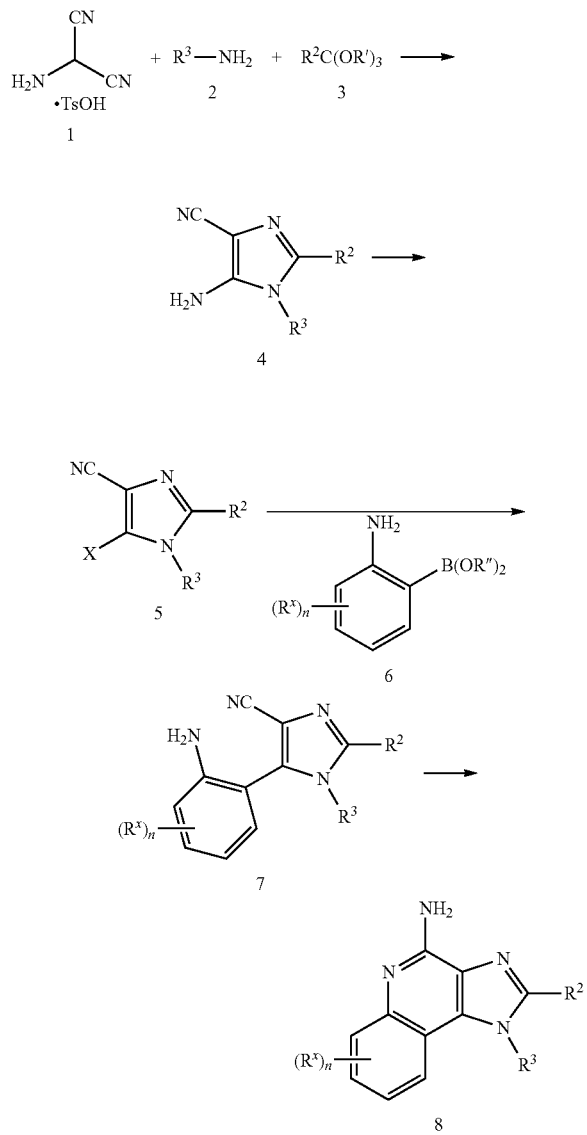

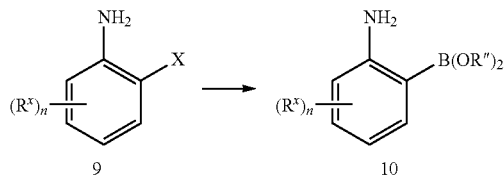

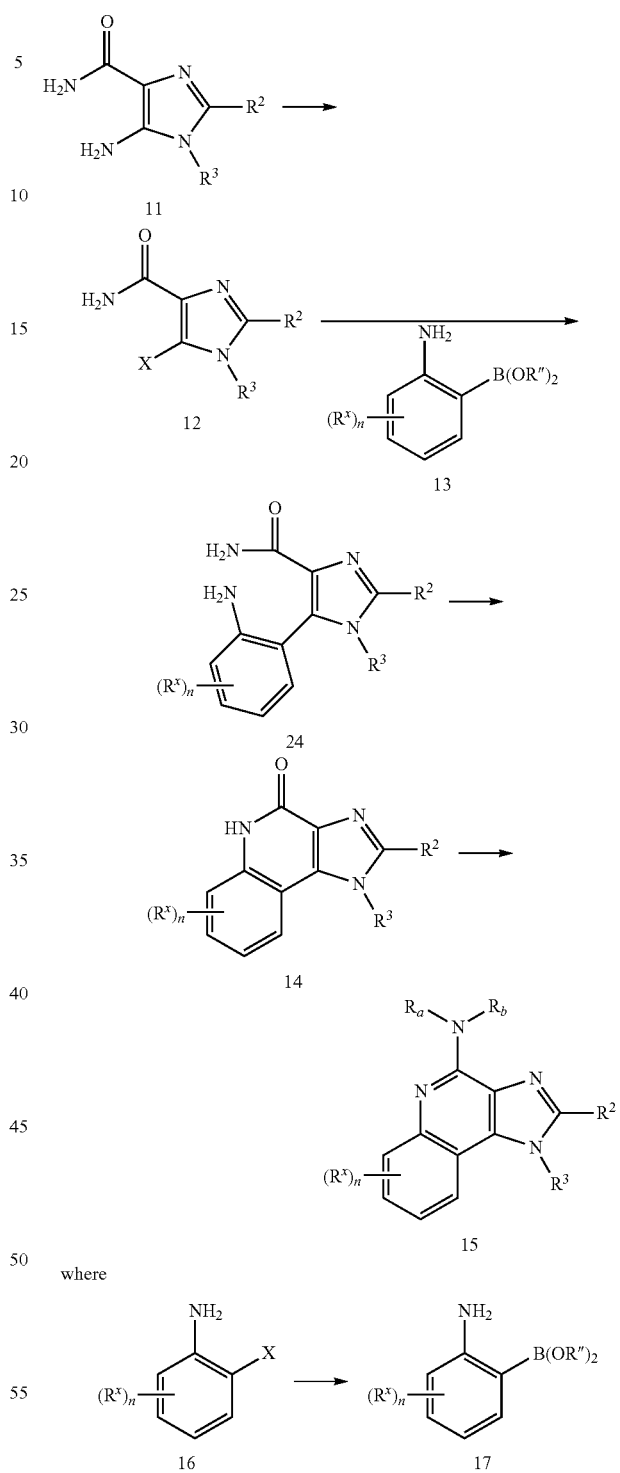

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLE 1

Preparation of 4-Amino-2-butyl-1-(2-hydroxy-2-methylpropyl)-7-methoxycarbonyl-1H-imidazo[4,5-c]quinoline (420)

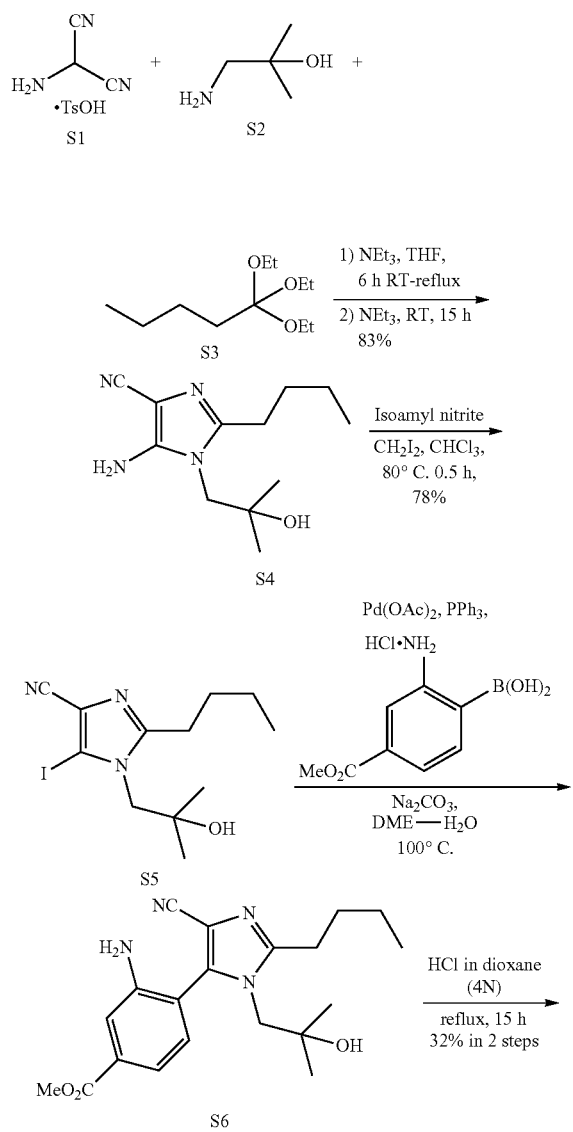

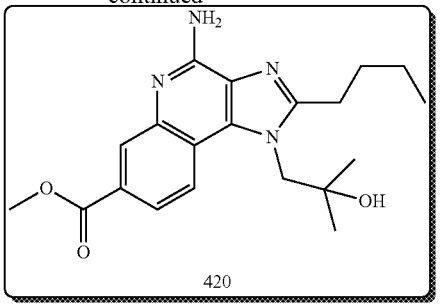

To 5-(2-amino-4-methoxycarbonylphenyl)-2-butyl-1-(2-hydroxy-2-methylpropyl)-1H-imidazole-4-carbonitrile S6 (118 mg, ~90% pure, 0.27 mmol, 1.0 equiv) was added 4 N HCl in dioxane (2.0 mL, 8.0 mmol, 30 equiv) at 25° C. The reaction was heated at reflux for 15 h then cooled to 25° C. The reaction was concentrated in vacuo and partitioned between 1:9 MeOH/EtOAc (50 mL) and saturated NaHCO$_3$ solution (10 mL). The aqueous layer was extracted with 1:9 MeOH/EtOAc (3×10 mL). The combined organic layers were washed with saturated aqueous NaCl, dried (MgSO$_4$), and concentrated in vacuo. Purification by flash column chromatography on silica gel (CH$_2$Cl$_2$-1/9 MeOH/CH$_2$Cl$_2$, gradient) afforded the title compound 420 (95 mg, 32% over 2 steps) as an off white solid: $^1$H NMR (CD$_3$OD, 600 Hz) δ 1.02 (t, J=6.6 Hz, 3H), 1.28 (br s, 6H), 1.51 (hex, J=7.8 Hz, 2H), 1.88 (pent, J=7.2 Hz, 2H), 3.13 (t, J=7.2 Hz, 2H), 3.95 (s, 3H), 7.86 (dd, J=8.4, 1.8 Hz, 1H), 8.33 (d, J=1.8 Hz, 1H), 8.37 (d, J=8.4 Hz, 1H); $^{13}$C NMR (CD$_3$OD, 150 Hz) δ 12.8, 22.2, 27.2, 29.7, 48.1, 51.3, 54.8, 71.1, 117.9, 118.6, 121.0, 121.3, 127.2, 127.9, 134.0, 143.6, 152.1, 157.3, 167.2; MS (APCI+): calcd C$_{20}$H$_{27}$N$_4$O$_3$ [M+H]$^+$ 371.5. found 371.5.

The intermediate compound S6 was prepared as follows.

a. 5-Amino-2-butyl-1-(2-hydroxy-2-methylpropyl)-1H-imidazole-4-carbonitrile (S4)

To a suspension of aminomalononitrile p-toluenesulfonate (2.0 g, 7.9 mmol, 1.0 equiv) in THF (30 mL) at 25° C. was added NEt$_3$ (1.3 mL, 9.5 mmol, 1.2 equiv) in one portion. The mixture was stirred for 30 min to afford a homogeneous solution. To this solution was added triethyl orthovalerate S3 (2.2 mL, 9.5 mmol, 1.2 equiv) and the solution was heated at reflux for 3 h. TLC indicated the presence of starting material, thus additional triethyl orthovalerate (1.1 mL, 4.7 mmol, 0.6 equiv) was added. The solution was heated at reflux for another 2 h then cooled to 25° C. Next, NEt$_3$ (1.3 mL, 9.5 mmol, 1.2 equiv) and 1-amino-2-methylpropan-2-ol S2 (844 mg, 9.5 mmol, 1.2 equiv) were added sequentially and the reaction was stirred at 25° C. for 15 h. The reaction was concentrated in vacuo and the resulting solid residue was redissolved in CH$_2$Cl$_2$ (100 mL) and washed with saturated aqueous Na$_2$CO$_3$ solution (25 mL). The aqueous layer was extracted with CH$_2$Cl$_2$ (3×20 mL). The combined organic fractions were washed with saturated aqueous NaCl, dried (MgSO$_4$) and concentrated in vacuo. Purification by flash column chromatography on silica gel (CH$_2$Cl$_2$-9/1 MeOH/CH$_2$Cl$_2$, gradient) afforded the title compound (1.55 g, 83%) as an off white solid: $^1$H NMR (CD$_3$OD, 600 Hz) δ 0.94 (t, J=6.0 Hz, 3H), 1.23 (s, 6H), 1.37 (hex, J=7.8 Hz, 2H), 1.66 (pent, J=6.0 Hz, 2H), 2.60 (t, J=6.0 Hz, 2H), 3.79 (s, 2H); $^{13}$C NMR (CD$_3$OD, 150 Hz) δ 12.7, 21.9, 26.0, 26.4, 29.1, 52.9, 71.2, 89.5, 116.2, 145.2, 149.2; MS (ESI+): calcd C$_{12}$H$_{21}$N$_4$O [M+H]$^+$ 237.3. found 237.4.

b. 2-Butyl-1-(2-hydroxy-2-methylpropyl)-5-iodo-1H-imidazole-4-carbonitrile (S5)

To a solution of 5-amino-2-butyl-1-(2-hydroxy-2-methylpropyl)-1H-imidazole-4-carbonitrile S4 (600 mg, 2.54 mmol, 1.0 equiv) and CH$_2$I$_2$ (2.0 mL) in CHCl$_3$ (25 mL) at 80° C. was added a solution of isoamylnitrite (1.36 mL, 10.2 mmol, 4.0 equiv) in CHCl$_3$ (5 mL) over 20 min. The reaction was stirred for additional 30 min at 80° C. then cooled to 25° C. The reaction was concentrated in vacuo and purification by silica gel column chromatography (1/9 EtOAc/hexanes-7/3 EtOAc/hexanes, gradient) afforded the title compound (687 mg, 78%) as a yellow solid: $^1$H NMR (CDCl$_3$, 600 Hz) δ 0.88 (t, J=6.0 Hz, 3H), 1.29 (s, 6H), 1.33 (hex, J=7.8 Hz, 2H), 1.66 (pent, J=7.8 Hz, 2H), 2.88 (t, J=7.8 Hz, 2H), 3.95 (s, 2H); $^{13}$C NMR (CDCl$_3$, 150 Hz) δ 13.7, 22.2, 28.3, 28.4, 29.6, 56.6, 71.6, 83.6, 115.1, 120.6, 155.4; MS (APCI+): calcd C$_{12}$H$_{19}$IN$_3$O [M+H]$^+$348.2. found 348.2.

c. 5-(2-Amino-4-methoxycarbonylphenyl)-2-butyl-1-(2-hydroxy-2-methylpropyl)-1H-imidazole-4-carbonitrile (S6)

To a suspension of Pd(OAc)$_2$ (11.2 mg, 0.05 mmol, 0.05 equiv) and PPh$_3$ (26.2 mg, 0.1 mmol, 0.1 equiv) in DME (4 mL) were sequentially added 2-butyl-1-(2-hydroxy-2-methylpropyl)-5-iodo-1H-imidazole-4-carbonitrile S5 (347 mg, 1 mmol, 1 equiv), 2-amino-4-methoxycarbonylphenylboronic acid hydrochloride salt (347 mg, 1.5 mmol, 1.5 equiv) and 1.5 M aqueous Na$_2$CO$_3$ (2.0 mL, 3 mmol, 3 equiv) at 25° C. The reaction was heated at 100° C. for 6 h. TLC and MS analysis indicated the presence of S5; consequently, additional Pd(OAc)$_2$ (5 mg) and PPh$_3$ (13 mg) were added and the reaction was heated further at 100° C. for 15 h. The reaction was then cooled down to 25° C. and partitioned between EtOAc (50 mL) and H$_2$O (10 mL). The aqueous layer was extracted with EtOAc (3×15 mL). The combined organic layers was washed with saturated aqueous NaCl (20 mL), dried (MgSO$_4$) and concentrated in vacuo. Purification by flash column chromatography on silica gel (1/9 EtOAc/hexanes-7/3 EtOAc/hexanes, gradient) afforded the title compound (118 mg, ~90% pure, 32%) as light yellow foam, which was used in the next step without further purification.

EXAMPLE 2

Preparation of 2-Butyl-7-methoxycarbonyl-4-{4-[(2,5-dioxo-2,5-dihydro-1H-pyrrol-1-yl)methyl]cyclohexanecarboxamido}-1-(2-hydroxy-2-methylpropyl)-1H-imidazo[4,5-c]quinoline (550)

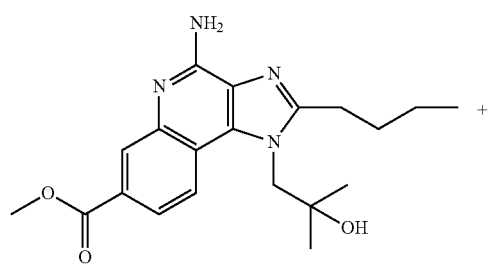

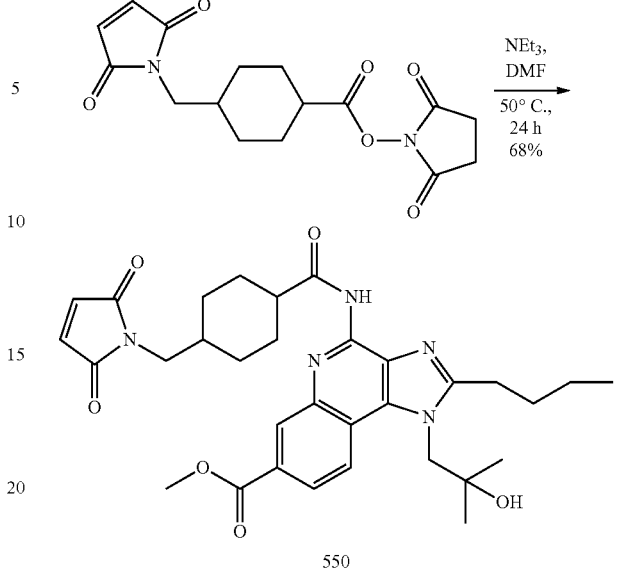

To a solution of 4-amino-2-butyl-1-(2-hydroxy-2-methylpropyl)-7-methoxycarbonyl-1H-imidazo[4,5-c]quinoline S7 (37 mg, 0.1 mmol, 1.0 equiv) and 2,5-dioxopyrrolidin-1-yl 4-[(2,5-dioxo-2,5-dihydro-1H-pyrrol-1-yl)methyl]cyclohexanecarboxylate (66 mg, 0.20 mmol, 2.0 equiv) in DMF (2.0 mL) at 25° C. was added NEt$_3$ (40 μL, 0.30 mmol, 3.0 equiv) in one injection. The reaction was heated at 50° C. for 24 h. The solvent was then removed in vacuo and the solid was redissolved in 1:9 MeOH/EtOAc (50 mL), washed successively with saturated NaHCO$_3$ solution (15 mL), H$_2$O (15 mL) and saturated aqueous NaCl (15 mL) and the organic layer concentrated. TLC and MS analysis indicated existence of both the imidazoquinoline starting material and the desired product. Purification by flash column chromatography on silica gel (CH$_2$Cl$_2$-1/9 MeOH/CH$_2$Cl$_2$, gradient) afforded the title compound 550 (40 mg, 68%) as a white solid: $^1$H NMR (CD$_3$OD, 600 Hz) δ 1.04 (t, J=7.2 Hz, 3H), 1.11-1.18 (m, 2H), 1.26 (br s, 6H), 1.51-1.66 (m, 4H), 1.68-1.85 (m, 3H), 1.91 (pent, J=7.2 Hz, 2H), 3.13 (t, J=7.2 Hz, 2H), 3.40 (d, J=7.2 Hz, 2H), 6.83 (s, 2H), 7.98 (d, J=9.0 Hz, 1H), 8.41 (d, J=9.0 Hz, 1H), 8.66 (s, 1H); $^{13}$C NMR (CD$_3$OD, 150 Hz) δ 12.9, 22.3, 27.2, 28.5, 28.7, 29.5, 29.6, 36.6, 43.1, 45.4, 51.4, 54.9, 71.1, 119.9, 121.4, 123.7, 126.5, 126.6, 126.6, 128.0, 128.8, 130.5, 133.9, 135.2, 142.5, 144.3, 158.2, 159.9, 160.0, 166.8, 171.4; MS (APCI+): calcd C$_{32}$H$_{40}$N$_5$O$_6$ [M+H]$^+$ 590.3. found 590.3.

EXAMPLE 3

Preparation of 4-Amino-1-isobutyl-7-methoxycarbonyl-1H-imidazo[4,5-c]-quinoline (412)

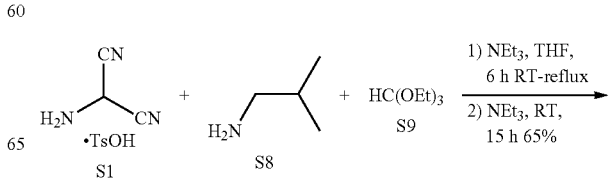

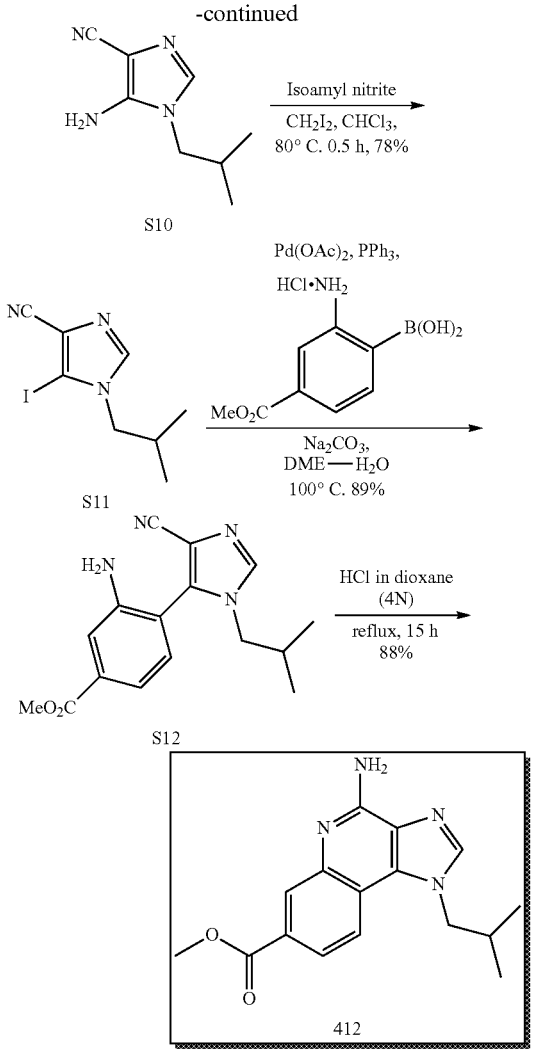

S10

S11

S12

412

To 5-(2-amino-4-methoxycarbonylphenyl)-1-isobutyl-1H-imidazole-4-carbonitrile S12 (150 mg, 0.50 mmol, 1.0 equiv) was added 4 N HCl in dioxane (2.0 mL, 8.0 mmol, 16 equiv). The reaction was heated at reflux condition for 15 h then cooled to 25° C. The reaction was concentrated in vacuo and partitioned between 1:9 MeOH/EtOAc (50 mL) and saturated aqueous NaHCO$_3$ solution (10 mL). The aqueous layer was extracted with 1:9 MeOH/EtOAc (3×10 mL). The combined organic layers were washed with saturated aqueous NaCl, dried (MgSO$_4$), and concentrated in vacuo. Purification by flash column chromatography on silica gel (CH$_2$Cl$_2$-1/9 MeOH/CH$_2$Cl$_2$, gradient) afforded the title compound 412 (132 mg, 88%) as an off white solid: $^1$H NMR (CD$_3$OD, 600 Hz) δ 1.01 (d, J=6.6 Hz, 6H), 2.26 (non, J=7.2 Hz, 1H), 3.96 (s, 3H), 4.43 (d, J=7.8 Hz, 2H), 7.89 (dd, J=7.8, 1.8 Hz, 1H), 8.05 (d, J=7.8 Hz, 1H), 8.19 (s, 1H), 8.32 (d, J=1.8 Hz, 1H); $^{13}$C NMR (CD$_3$OD, 150 Hz) δ 18.4, 28.7, 51.4, 54.2, 117.9, 120.5, 121.8, 127.1, 128.6, 128.8, 132.1, 143.6, 144.3, 152.5, 167.0; MS (APCI+): calcd C$_{16}$H$_{19}$N$_4$O$_2$ [M+H]$^+$ 299.2. found 299.2.

The intermediate compound S12 was prepared as follows.

a. 5-Amino-1-isobutyl-1H-imidazole-4-carbonitrile (S10)

To a suspension of aminomalononitrile p-toluenesulfonate (1 g, 4.0 mmol, 1 equiv) in THF (30 mL) at 25° C. was added NEt$_3$ (0.65 mL, 4.8 mmol, 1.2 equiv) in one portion. The mixture was stirred for 30 min to afford a homogeneous solution. To this solution was added triethyl orthoformate (0.80 mL, 4.8 mmol, 1.2 equiv) and the solution was heated at reflux for 3 h. TLC indicated the presence of starting material and additional triethyl orthoformate (0.4 mL, 2.4 mmol, 0.6 equiv) was added. The solution was heated at reflux for another 2 h then cooled to 25° C. NEt$_3$ (0.65 mL, 4.8 mmol, 1.2 equiv) and isobutylamine (350 mg, 4.8 mmol, 1.2 equiv) were added sequentially and the reaction was stirred at 25° C. for 15 h. The reaction was concentrated in vacuo and the crude residue was redissolved in CH$_2$Cl$_2$ (100 mL) and washed with saturated Na$_2$CO$_3$ solution (25 mL) The aqueous layer was extracted with CH$_2$Cl$_2$ (3×20 mL). The combined organic fractions were washed with saturated aqueous NaCl, dried (MgSO$_4$), and concentrated in vacuo. Purification by flash column chromatography on silica gel (CH$_2$Cl$_2$-1/9 MeOH/CH$_2$Cl$_2$, gradient) afforded the title compound (426 mg, 65%) as a light yellow solid: $^1$H NMR (CDCl$_3$, 600 Hz) δ 0.96 (d, J=6.6 Hz, 6H), 2.01-2.07 (m, 1H), 3.57 (d, J=7.8 Hz, 2H), 3.94 (br s, 2H), 7.05 (s, 1H); $^{13}$C NMR (CDCl$_3$, 150 Hz) δ 19.8, 28.9, 51.6, 115.7, 116.5, 133.5, 144.8; MS (ESI+): calcd C$_8$H$_{13}$N$_4$ [M+H]$^+$ 165.1. found 165.1.

b. 5-Iodo-1-isobutyl-1H-imidazole-4-carbonitrile (S11)

To a solution of 5-amino-1-isobutyl-1H-imidazole-4-carbonitrile S10 (410 mg, 2.5 mmol, 1 equiv) and CH$_2$I$_2$ (2 mL) in CHCl$_3$ (25 mL) at 80° C. was added a solution of isoamylnitrite (1.36 mL, 10.2 mmol, 4.0 equiv) in CHCl$_3$ (5.0 mL) over 20 min. The reaction was heated for additional 30 min, then cooled to 25° C. and concentrated in vacuo. Purification by silica gel column chromatography (1/9 EtOAc/hexanes-7/3 EtOAc/hexanes, gradient) afforded the title compound (536 mg, 78%) as an orange solid: $^1$H NMR (CDCl$_3$, 600 Hz) δ 0.92 (d, J=7.2 Hz, 6H), 2.12 (non, J=10.2 Hz, 1H), 3.76 (d, J=7.8 Hz, 2H), 7.62 (s, 1H); $^{13}$C NMR (CDCl$_3$, 150 Hz) δ 19.6, 29.5, 56.1, 82.7, 114.6, 122.5, 141.3; LRMS (APCI+): calcd C$_8$H$_{11}$IN$_3$ [M+H]$^+$ 276.1. found 276.0.

c. 5-(2-Amino-4-methoxycarbonylphenyl)-1-isobutyl-1H-imidazole-4-carbonitrile (S12)

To a suspension of Pd(OAc)$_2$ (11.2 mg, 0.05 mmol, 0.05 equiv) and PPh$_3$ (26.2 mg, 0.1 mmol, 0.1 equiv) in DME (4 mL) were sequentially added 5-iodo-1-isobutyl-1H-imidazole-4-carbonitrile S5 (275 mg, 1 mmol, 1 equiv), 2-amino-4-methoxycarbonylphenyl-boronic acid hydrochloride salt (347 mg, 1.5 mmol, 1.5 equiv) and 1.5 M aqueous Na$_2$CO$_3$ (2.0 mL, 3.0 mmol, 3.0 equiv) at 25° C. The reaction was heated at 100° C. for 3 h. TLC and MS analysis indicated complete conversion of S5. The reaction was then cooled down to 25° C. and partitioned between EtOAc (50 mL) and H$_2$O (10 mL). The aqueous layer was extracted with EtOAc (3×15 mL) and the combined organic layers were washed with saturated aqueous NaCl (20 mL), dried (MgSO$_4$) and concentrated in vacuo. Purification by flash column chromatography on silica gel (1/9 EtOAc/hexanes-7/3 EtOAc/hexanes, gradient) afforded the title compound (265 mg, 89%) as a light yellow foam: $^1$H NMR (CDCl$_3$, 600 Hz) δ 0.71 (d, J=9.6 Hz, 3H), 0.75 (d, J=9.6 Hz, 3H), 1.75 (hept, J=9.6 Hz, 1H), 3.64-3.67 (m, 2H), 3.90 (s, 3H), 7.15 (d, J=7.8 Hz, 1H), 7.44 (d, J=7.8 Hz), 7.45 (s, 1H), 7.57 (s, 1H); $^{13}$C NMR (CDCl$_3$, 150 Hz) δ 19.6, 19.7, 29.5, 52.3, 53.6, 117.0, 128.4, 128.5, 131.7, 131.9, 131.9, 132.0, 132.1, 133.2, 139.8, 166.5; LRMS (ESI+): calcd C$_{16}$H$_{19}$N$_4$O$_2$ [M+H]$^+$299.2. found 299.1.

EXAMPLE 4

Preparation of Additional Compounds of the Invention

Using procedures similar to those described herein the following compounds of formula I were also prepared.

| Cmpd # | Structure | Name | Characterization |
|---|---|---|---|
| 527 | (structure) | 4-Amino-1-(2-hydroxyl-2-methylpropyl)-7-methoxy carbonyl-2-pentyl-1H-imidazo[4,5-c]quinoline | $^1$H NMR (DMF-$d_7$, 600 MHz) δ 0.92 (t, J = 7.2 Hz, 3H), 1.31 (brs, 6H), 1.42-1.46 (m, 4H), 1.91 (p, J = 7.2 Hz, 2H), 3.14 (t, J = 7.8 Hz, 2H), 3.96 (s, 3H), 4.67 (brs, 2H), 5.01 (s, 1H), 6.69 (brs, 2H), 7.78 (dd, J = 8.4, 1.8 Hz, 1H), 8.31 (d, J = 1.8 Hz, 1H), 8.53 (d, J = 9.0 Hz, 1H); $^{13}$C NMR (DMF-$d_7$, 150 MHz) δ 14.5, 23.2, 28.2, 28.3, 28.4, 32.4, 52.6, 55.8, 72.0, 120.1, 121.0, 122.8, 128.0, 128.8, 129.0, 134.4, 145.5, 153.6, 157.7, 167.8; HRMS (ESI+): calcd $C_{21}H_{29}N_4O_3$ [M + H]+ 385.2234, found 385.2234 (error 0 ppm). |
| 528 | (structure) | (S)-4-Amino-2-butyl-1-(2-hydroxypropyl)-7-methoxycarbonyl-1H-imidazo[4,5-c]quinoline | $^1$H (DMF-$d_7$, 400 MHz): δ 8.31 (s, 1H), 8.24 (d, J = 8.61, 1H), 7.80 (dd, J = 8.61, 1.17), 6.69 (s, 2H), 5.30 (d, J = 4.69, 1H), 4.70 (dd, J = 2.93, 15.06, 1H), 4.46 (dd, J = 9.2, 15.06), 4.26 (m, 1H), 3.95 (s, 3H), 2.06 (m, 2H), 1.90 (pent., J = 7.43, 2H), 1.51 (sextet, J = 7.43, 2H), 1.39 (d, J = 6.26, 3H), 0.99 (t, J = 7.43, 3H). $^{13}$C (DMF-$d_7$, 100 MHz): δ 167.2, 156.0, 153.2, 144.9, 132.8, 128.7, 128.5, 127.5, 121.1, 120.9, 119.1, 66.3, 52.8, 52.0, 29.7, 27.3, 22.6, 20.8, 13.8. HRMS (APCI+): calcd $C_{19}H_{25}N_4O_3$ [M + H]+ 357.1921, found 357.1926 (error 1.4 ppm). |
| 529 | (structure) | 4-Amino-2-butyl-1-(2-hydroxyethyl)-7-methoxycarbonyl-1H-imidazo[4,5-c]quinoline | $^1$H (DMF-$d_7$, 400 MHz): δ 8.37-8.27 (2H), 7.82 (dd, J = 8.61, 1.76, 1H), 6.95 (s, 2H), 5.28 (t, J = 5.28, 1H), 4.77 (t, J = 5.28, 1H), 4.05 (m, 2H), 3.96 (s, 3H), 3.07 (t, J = 7.83, 2H), 1.90 (quintet, J = 7.63, 2H), 1.52 (sextet, J = 7.63, 2H), 0.99 (t, J = 7.43, 3H). $^{13}$C (DMF-$d_7$, 100 MHz): δ 167.8, 157.0, 153.7, 133.7, 129.2, 128.6, 122.1, 122.0, 119.5, 61.6, 52.8, 48.9, 27.9, 23.4, 14.5. HRMS (APCI+): calcd $C_{18}H_{23}N_4O_3$ [M + H]+ 343.1765, found 343.1754 (error 3.1 ppm). |

| Cmpd # | Structure | Name | Characterization |
|---|---|---|---|
| 531 | 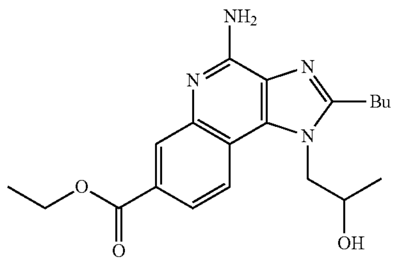 | 4-Amino-2-butyl-1-(2-hydroxypropyl)-7-ethoxycarbonyl-1H-imidazo[4,5-c]quinoline | $^1$H (DMF-d$_7$, 400 MHz): δ 8.33 (d, J = 1.88, 1H), 8.23 (d, J = 8.48, 1H), 7.81 (dd, J = 1.81, 8.48, 1H), 6.70 (s, 2H), 5.32 (d, J = 4.29, 1H), 4.70 (dd, J = 3.07, 15.0, 1H), 4.52-4.36 (m, 3H), 4.27 (m, 1H), 3.06 (m, 2H), 1.90 (quintet, J = 7.54, 2H), 1.52 (sextet, J = 7.54, 2H), 1.45-1.36 (m, 2H), 0.99 (t, J = 7.54, 3H). $^{13}$C (DMF-d$_7$, 100 MHz): δ 167.5, 156.7, 154.0, 145.7, 133.6, 129.4, 129.3, 128.6, 121.9, 121.7, 119.8, 67.1, 61.8, 53.6, 30.5, 28.1, 23.4, 21.6, 15.0, 14.6. HRMS (APCI+): calcd C$_{20}$H$_{27}$N$_4$O$_3$ [M + H]+ 371.2078, found 371.2087 (error 2.59 ppm). |
| 520 | 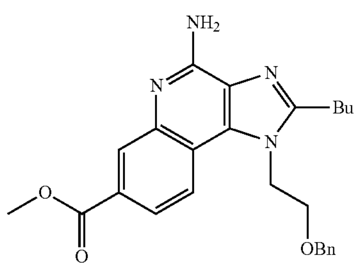 | 4-Amino-1-(2-(benzyloxy)ethyl)-2-butyl-7-methoxycarbonyl 1H-imidazo[4,5-c]quinoline | $^1$H NMR (CDCl$_3$, 400 Hz) δ 8.53 (s, 1H), 7.95-7.85 (2H), 7.26-7.09 (5H), 5.48 (s, 2H), 4.70 (t, J = 5.67, 2H), 4.49 (s, 2H), 3.96 (s, 3H), 3.94 (t, J = 5.67, 2H), 2.97 (t, J = 7.83, 2H), 1.86 (quintet, J = 7.83, 2H), 1.49 (sextet, J = 7.43, 2H), 0.98 (t, J = 7.43, 3H). $^{13}$C (CDCl$_3$, 100 MHz): δ 167.3, 155.4, 151.6, 144.0, 137.0, 132.7, 129.3, 128.4, 127.9, 127.6, 122.1, 119.3, 118.5, 73.5, 67.9, 52.2, 45.6, 29.9, 27.2, 22.6, 13.8. HRMS (APCI+): calcd C$_{25}$H$_{29}$N$_4$O$_3$ [M + H]+ 433.2234, found 433.2235 (error 0.14 ppm). |
| 522 | 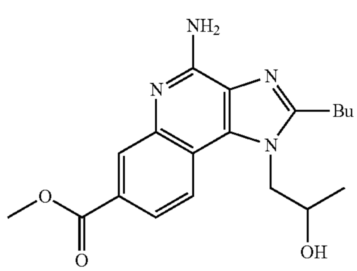 | 4-Amino-2-butyl-1-(2-hydroxypropyl)-7-methoxycarbonyl-1H-imidazo[4,5-c]quinoline | $^1$H (DMF-d$_7$, 400 MHz): δ 8.31 (d, J = 1.61, 1H), 8.24 (d, J = 8.73, 1H), 7.80 (dd, J = 8.5, 1.84, 1H), 6.68 (s, 2H), 5.29 (s, 1H), 4.70 (dd, J = 15.2, 3.22, 1H), 4.46 (dd, J = 14.94, 9.19, 1H), 4.26 (m, 1H), 3.95 (s, 3H), 3.06 (m, 2H), 1.90 (quintet, J = 7.81, 2H), 1.52 (sextet, J = 7.35, 2H), 1.39 (d, J = 6.21, 2H), 0.99 (t, J = 7.35, 3H). $^{13}$C (DMF-d$_7$, 100 MHz): δ 167.1, 156.1, 153.1, 144.5, 132.8, 128.4, 128.3, 127.6, 121.2, 121.1, 119.0, 66.3, 52.8, 52.0, 29.7, 27.3, 22.6, 20.8, 13.8. HRMS (APCI+): calcd C$_{19}$H$_{25}$N$_4$O$_3$ [M + H]+ 357.1921, found 357.1926 (error 1.4 ppm). |

| Cmpd # | Structure | Name | Characterization |
|---|---|---|---|
| 533 | 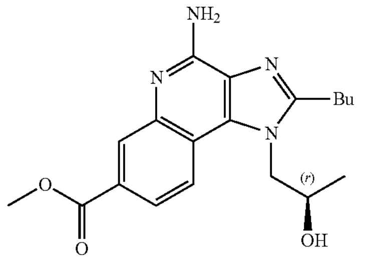 | (R)-4-Amino-2-butyl-1-(2-hydroxypropyl)-7-methoxycarbonyl-1H-imidazo[4,5-c]quinoline | $^1$H (DMF-d$_7$, 400 MHz): δ 8.33 (d, J = 1.57, 1H), 8.27 (d, J = 8.80, 1H), 7.84 (dd, J = 8.61, 1.76, 1H), 7.03 (s, 2H), 5.33 (d, J = 3.52, 1H), 4.71 (dd, J = 15.06, 3.13, 1H), 4.47 (dd, J = 15.06, 9.39, 1H), 4.27 (m, 1H), 3.96 (s, 3H), 3.07 (m, 2H), 1.90 (quintet, J = 7.43, 2H), 1.52 (sextet, J = 7.43, 2H), 1.40 (d, J = 6.26, 3H), 0.99 (t, J = 7.43, 3H). $^{13}$C (DMF-d$_7$, 100 MHz): δ 167.0, 156.4, 152.8, 143.5, 133.1, 128.3, 127.9, 127.5, 121.4, 121.3, 118.8, 66.3, 52.9, 52.1, 29.6, 27.3, 22.6, 20.8, 13.8. HRMS (APCI+): calcd C$_{19}$H$_{25}$N$_4$O$_3$ [M + H]+ 357.1921, found 357.1919 (error 0.74 ppm). |
| 521 | 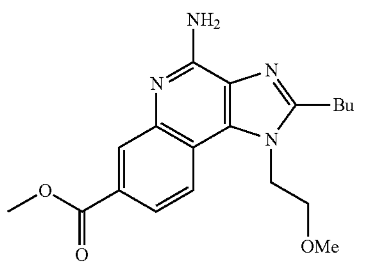 | 4-Amino-2-butyl-1-(2-methoxyethyl)-7-methoxycarbonyl-1H-imidazo[4,5-c]quinolone | $^1$H (CDCl$_3$, 400 MHz): δ 8.31 (d, J = 1.76, 1H), 8.27 (d, J = 8.61, 1H), 7.80 (dd, J = 8.61, 1.76, 1H), 6.69 (s, 2H), 4.86 (t, J = 5.28, 2H), 3.96 (s, 3H), 3.91 (t, J = 5.28, 2H), 3.26 (s, 3H), 3.03 (t, J = 7.63, 2H), 1.89 (quintet, J = 7.63, 2H), 1.52 (sextet, J = 7.63, 2H), 0.99 (t, J = 7.43, 3H). $^{13}$C (CDCl$_3$, 100 MHz): δ 168.0, 156.5, 154.0, 145.8, 133.4, 129.5, 129.4, 128.5, 121.7, 119.7, 72.2, 59.5, 52.8, 46.4, 27.7, 23.4, 14.5. HRMS (APCI+): calcd C$_{19}$H$_{25}$N$_4$O$_3$ [M + H]+ 357.1921, found 357.1920 (error 0.3 ppm). |
| 421 | 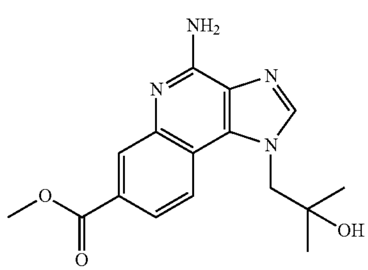 [SMILES: COC(=O)c1ccc2c(c1)nc(N)c1ncn(CC(C)(C)O)c12] | 4-amino-1-(2-hydroxy-2-methylpropyl)-7-methoxycarbonyl-1H-imidazo[4,5-c]quinoline | $^1$H NMR (CD$_3$OD, 600 Hz) δ 1.30 ( br s, 6H), 3.96 (s, 3H), 4.67 (s, 2H), 7.92 (dd, J = 9.0, 1.8 Hz, 1H), 8.21 (s, 2H), 8.36 (d, J = 1.8 Hz, 1H), 8.44 (d, J = 9.0 Hz, 1H); $^{13}$C NMR (CD$_3$OD, 150 Hz) δ 26.0, 51.3, 56.7, 69.9, 118.3, 121.5, 121.6, 126.5, 128.2, 128.6, 133.3, 143.3, 145.3, 152.4, 167.0; LRMS (APCI+): calcd C$_{16}$H$_{19}$N$_4$O$_3$ [M + H]$^+$ 315.1, found 315.1. |

| Cmpd # | Structure | Name | Characterization |
|---|---|---|---|
| 530 | 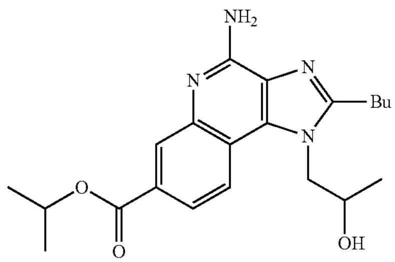 | 4-Amino-2-butyl-1-(2-hydroxypropyl)-7-isopropoxycarbonyl-1H-imidazo[4,5-c]quinoline | $^1$H (DMF-d$_7$, 400 MHz): δ 8.32 (d, J = 1.76, 1H), 8.23 (d, J = 8.61, 1H), 7.81 (dd, J = 1.76, 8.91, 1H), 6.72 (s, 2H), 5.31 (d, J = 4.89, 1H), 5.29 (septet, J = 6.26, 1H), 4.70 (dd, J = 3.13, 15.06, 1H), 4.46 (dd, J = 9.0, 15.06, 1H), 4.77 (m, 1H), 3.06 (m, 2H), 1.90 (pentet, J = 7.63, 2H), 1.52 (sextet, J = 7.43, 2H), 1.41 (d, J = 6.26, 6H), 1.41 (d, J = 6.29, 3H), 0.99 (t, J = 7.43, 3H). $^{13}$C (DMF-d$_7$, 100 MHz): δ 167.0, 156.8, 153.9, 145.6, 133.6, 129.3, 129.0, 121.8, 121.7, 119.7, 69.2, 67.1, 53.6, 30.5, 28.1, 23.4, 22.5, 21.6, 14.6. HRMS (APCI+): calcd C$_{21}$H$_{29}$N$_4$O$_3$ [M + H]+ 385.2234, found 385.2234 (error 0.07 ppm). |
| 535 | 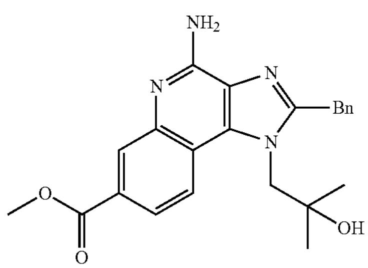 | 4-Amino-2-benzyl-1-(2-hydroxyl-2-methylpropyl)-7-methoxycarbonyl-1H-imidazo[4,5-c]quinoline | $^1$H NMR (DMF-d$_7$, 600 MHz) δ 1.33 (br s, 6H), 3.95 (s, 3H), 4.65 (br s, 4H), 6.78 (br s, 2H), 7.25-7.27 (m, 1H), 7.33-7.35 (m, 4H), 7.76 (d, J = 9.0 Hz, 1H), 8.30 (s, 1H), 8.49 (d, J = 9.0 Hz, 1H); $^{13}$C NMR (DMF-d$_7$, 150 MHz) δ 28.1, 34.9, 52.6, 56.2, 72.1, 120.1, 121.1, 122.7, 127.5, 128.3, 129.1, 129.2, 129.5, 129.7, 134.7, 138.7, 145.8, 153.8, 155.8, 167.8; HRMS (ESI+): calcd C$_{23}$H$_{25}$N$_4$O$_3$ [M + H]$^+$ 405.1927, found 405.1935 (error 2.0 ppm). |
| 525 | 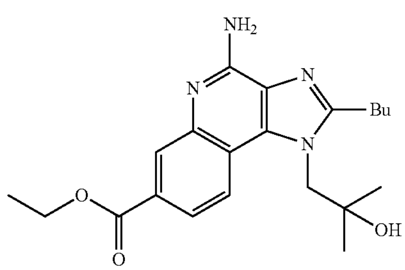 | 4-Amino-2-butyl-1-(2-hydroxyl-2-methylpropyl)-7-ethoxycarbonyl-1H-imidazo[4,5-c]quinoline | $^1$H NMR (CD$_3$OD, 600 MHz) δ 1.02 (t, J = 7.2 Hz, 3H), 1.19 (br s, 6H), 1.43 (t, J = 7.2 Hz, 3H), 1.51 (hex, J = 7.2 Hz, 2H), 1.89 (pent, J = 7.2 Hz, 2H), 3.12 (t, J = 7.8 Hz, 2H), 4.41 (q, J = 7.2 Hz, 2H), 4.65 (br s, 2H), 7.85 (d, J = 9.0 Hz, 1H), 8.33 (s, 1H), 8.34 (d, J = 9.0 Hz, 1H); $^{13}$C NMR (CD$_3$OD, 150 MHz) δ 14.4, 14.8, 23.8, 27.9, 28.8, 31.2, 56.4, 62.4, 72.7, 120.1, 122.5, 122.8, 128.2, 128.7, 129.8, 135.5, 145.2, 153.7, 158.8, 168.3; HRMS (ESI+): calcd C$_{21}$H$_{29}$N$_4$O$_3$ [M + H]$^+$ 385.2240, found 385.2245 (error 1.3 ppm). |

-continued

| Cmpd # | Structure | Name | Characterization |
|---|---|---|---|
| 536 | 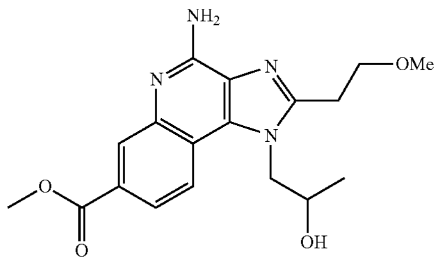 [SMILES: COCCc1nc2c(N)nc3cc(C(=O)OC)ccc3c2n1CC(C)O] | 4-Amino-1-(2-hydroxypropyl)-2-(2-methoxyethyl)-7-carboxylate-1H-imidazo[4,5-c]quinoline | $^1$H (DMSO-d$_6$, 400 MHz): δ 8.18 (s, 1H), 8.12 (d, J = 8.80, 1H), 7.75 (dd, J = 0.78, 8.80, 1H), 4.59 (dd, J = 2.74, 15.26, 1H), 4.37 (dd, J = 9.0, 15.26, 1H), 4.03 (m, 1H), 3.89 (s, 3H), 3.84 (t, J = 6.85, 2H), 3.30 (s, 3H), 3.24 (m, 2H), 1.27 (d, J = 6.06, 3H) $^{13}$C (DMSO-d$_6$, 100 MHz): δ 166.5, 152.8, 152.4, 144.1, 132.0, 127.8, 127.6, 126.9, 120.7, 120.4, 118.2, 70.0, 65.4, 58.1, 52.1, 52.0, 27.5, 20.9. HRMS (APCI+): calcd C$_{18}$H$_{23}$N$_4$O$_4$ [M + H]+ 359.1714, found 359.1717 (error 0.9 ppm). |
| 526 | 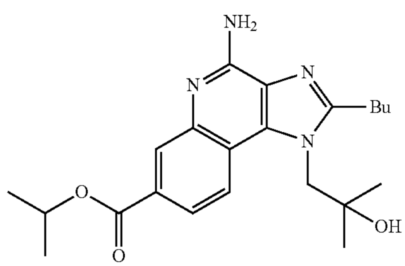 | 4-Amino-2-butyl-1-(2-hydroxyl-2-methyl-propyl)-7-isopropylcarbonyl-1H-imidazo[4,5-c]quinoline | $^1$H NMR (CD$_3$OD, 600 MHz) δ 1.02 (t, J = 7.8 Hz, 3H), 1.28 (br s, 6H), 1.41 (d, J = 6.0 Hz, 6H), 1.52 (hex, J = 7.8 Hz, 2H), 1.89 (pent, J = 7.8 Hz, 2H), 3.13 (t, J = 7.8 Hz, 2H), 4.59 (br s, 2H), 5.26 (hept, J = 6.0 Hz, 1H); $^{13}$C NMR (CD$_3$OD, 150 MHz) δ 14.4, 22.3, 23.8, 28.4, 28.7, 31.2, 56.4, 70.0, 72.7, 111.9, 120.1, 122.5, 122.8, 128.5, 130.2, 135.5, 145.1, 153.6, 158.8, 167.8; HRMS (ESI+): calcd C$_{22}$H$_{31}$N$_4$O$_3$ [M + H]$^+$ 399.2396, found 399.2398 (error 0.5 ppm). |
| 504 | 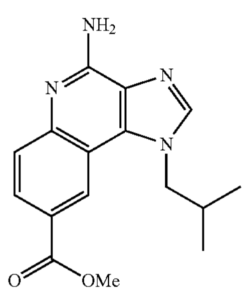 [SMILES: COC(=O)c1ccc2nc(N)c3ncn(CC(C)C)c3c2c1] | 4-amino-1-isobutyl-8-methoxycarbonyl-1H-imidazo[4,5-c]quinoline | $^1$H NMR (DMF-d$_7$, 400 Hz) δ 1.21 (d, J = 6.8 Hz, 6H), 2.42-2.49 (m, 1H), 4.12 (s, 3H), 4.68 (d, J = 7.2 Hz, 2H), 7.27 (br s, 2H), 7.88 (d, J = 8.4 Hz, 1H), 8.17 (d, J = 8.4 Hz, 1H), 8.49 (s, 1H), 8.89 (s, 1H); $^{13}$C NMR (DMF-d$_7$, 100 Hz) δ 19.2, 28.9, 51.8, 54.2, 114.8, 122.2, 123.4, 126.7, 126.8, 129.1, 132.5, 144.0, 148.9, 154.5, 166.9. LRMS (APCI+): calcd C$_{16}$H$_{19}$N$_4$O$_2$ [M + H]$^+$ 299.2, found 299.2. |
| 516 | 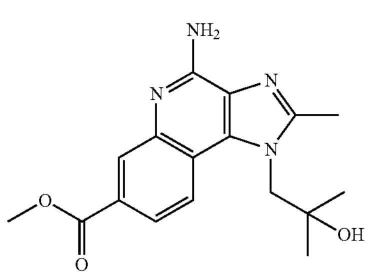 [SMILES: COC(=O)c1ccc2c(c1)nc(N)c1nc(C)n(CC(C)(C)O)c12] | 4-amino-1-(2-hydroxy-2-methylpropyl)-7-methoxycarbonyl-2-methyl-1H-imidazo[4,5-c]quinoline | $^1$H NMR (CD$_3$OD, 400 Hz) δ 1.30 (br s, 6H), 2.76 (s, 3H), 3.95 (s, 3H), 7.86 (dd, J = 8.4, 1.6 Hz, 1H), 8.33 (d, J = 1.6 Hz, 1H), 8.37 (d, J = 8.4 Hz, 1H); $^{13}$C NMR (CD$_3$OD, 100 Hz) δ 15.2, 27.4, 52.9, 56.8, 72.9, 111.6, 120.1, 122.7, 122.9, 128.3, 128.7, 135.7, 145.0, 153.5, 155.4, 168.7; LRMS (APCI+): calcd C$_{19}$H$_{25}$N$_4$O$_3$ [M + H]$^+$ 329.2, found 329.2. |

| Cmpd # | Structure | Name | Characterization |
|---|---|---|---|
| 518 | 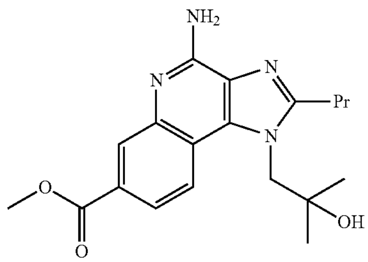 | 4-amino-1-(2-hydroxy-2-methylpropyl)-7-methoxycarbonyl-2-propyl-1H-imidazo[4,5-c]quinoline | $^1$H NMR (CD$_3$OD, 600 Hz) δ 1.09 (t, J = 7.2 Hz, 3H), 1.28 (br s, 6H), 1.92-1.96 (m, 2H), 3.09 (t, J = 7.8 Hz, 2H), 3.95 (s, 3H), 7.84 (d, J = 9.0 Hz, 1H), 8.32 (s, 1H), 8.34 (d, J = 9.0 Hz, 1H); $^{13}$C NMR (CD$_3$OD, 150 Hz) δ 12.8, 20.8, 25.8, 29.3, 51.3, 54.8, 71.1, 118.3, 118.6, 121.0, 121.3, 127.1, 127.9, 133.9, 143.6, 152.1, 157.0, 167.2; LRMS (APCI+): calcd C$_{19}$H$_{25}$N$_4$O$_3$ [M + H]$^+$ 357.2, found 357.2. |
| 511 | 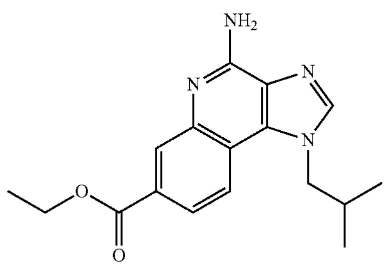 [SMILES: CCOC(=O)c1ccc2c(c1)nc(N)c1ncn(CC(C)C)c12] | 4-Amino-7-ethoxycarbonyl-1-(2-methylpropyl)-1H-imidazo[4,5-c]quinoline | $^1$H NMR (CD$_3$OD, 600 MHz) δ 0.99 (d, J = 7.2 Hz, 1H), 1.43 (t, J = 7.2 Hz, 3H), 2.24 (hept, J = 7.2 Hz, 1H), 4.41 (q, J = 7.2 Hz, 2H), 7.87 (dd, J = 7.8, 1.8 Hz, 1H), 8.01 (d, J = 7.2 Hz, 1H), 8.17 (s, 1H), 8.31 (d, J = 1.2 Hz, 1H); $^{13}$C NMR (CD$_3$OD, 150 MHz) δ 14.8, 19.9, 30.2, 55.7, 62.5, 119.4, 122.0, 123.4, 128.5, 130.3, 130.5, 133.7, 144.9, 145.8, 154.0, 168.0; HRMS (ESI+): calcd C$_{17}$H$_{21}$N$_4$O$_2$ [M + H]$^+$ 313.1665, found 313.1668 (error 1.0 ppm). |
| 503 | 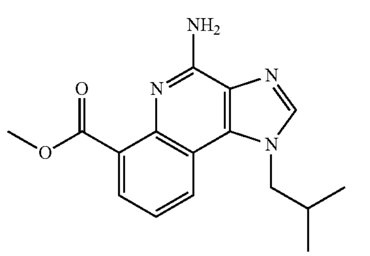 [SMILES: COC(=O)c1cccc2c1nc(N)c1ncn(CC(C)C)c12] | : 4-Amino-6-methoxycarbonyl-1-(2-methylpropyl)-1H-imidazo[4,5-c]quinoline | $^1$H NMR (CD$_3$OD, 600 MHz) δ 0.99 (d, J = 6.6 Hz, 6H), 2.24 (hept, J = 6.6 Hz, 1H), 3.98 (s, 3H), 4.40 (d, J = 7.8 Hz, 2H), 7.35 (t, J = 7.2 Hz, 1H), 7.78 (d, J = 7.2 Hz, 1H), 8.13 (d, J = 6.0 Hz, 1H), 8.14 (s, 1H); $^{13}$C NMR (CD$_3$OD, 150 MHz) δ 19.9, 30.1, 53.0, 55.7, 117.0, 122.3, 125.2, 129.0, 129.4, 133.8, 145.4, 153.7, 171.2. HRMS (ESI+): calcd C$_{16}$H$_{19}$N$_4$O$_2$ [M + H]$^+$ 299.1508, found 299.1499 (error −3.0 ppm). |
| 517 | 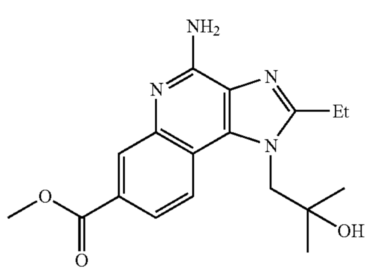 | 4-amino-2-ethyl-1-(2-hydroxy-2-methylpropyl)-7-methoxycarbonyl-1H-imidazo[4,5-c]quinoline | $^1$H NMR (CD$_3$OD, 600 Hz) δ 1.30 (br s, 6H), 1.47 (t, J = 7.8 Hz, 3H), 3.15 (q, J = 7.8 Hz, 2H), 3.96 (s, 3H), 7.87 (dd, J = 9.0, 1.2 Hz, 1H), 8.34 (d, J = 1.2 Hz, 1H), 8.38 (d, J = 9.0 Hz, 1H); $^{13}$C NMR (CD$_3$OD, 150 Hz) δ 10.8, 20.8, 25.8, 51.3, 54.8, 71.1, 118.0, 118.5, 121.0, 121.4, 127.1, 127.9, 134.1, 143.6, 152.1, 158.2, 167.2; LRMS (APCI+): calcd C$_{19}$H$_{25}$N$_4$O$_3$ [M + H]$^+$ 343.2, found 343.2. |

| Cmpd # | Structure | Name | Characterization |
|---|---|---|---|
| 523 | 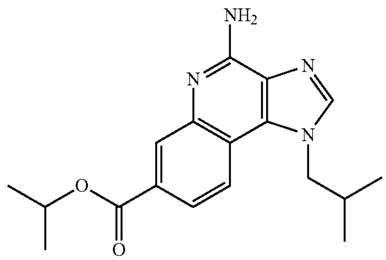 [SMILES: CC(C)Cn1cnc2c(N)nc3cc(C(=O)OC(C)C)ccc3c21] | 4-Amino-7-isopropylcarbonyl-1-(2-methylpropyl)-1H-imidazo[4,5-c]quinoline | $^1$H NMR (DMF-$d_6$, 600 MHz) δ 0.99 (d, J = 7.2 Hz, 6H), 1.40 (d, J = 6.6 Hz, 6H), 2.28 (hept, J = 7.2 Hz, 1H), 4.54 (d, J = 7.8 Hz, 1H), 5.24 (hept, J = 6.6 Hz, 1H), 6.85 (br s, 2H), 7.85 (d, J = 7.8 Hz, 1H), 8.21 (d, J = 9.0 Hz, 1H), 8.34 (d, J = 1.2 Hz, 1H); 8.35 (s, 1H); $^{13}$C NMR (DMF-$d_6$, 150 MHz) δ 20.0, 22.4, 30.2, 54.9, 69.2, 119.6, 122.0, 122.1, 129.3, 129.7, 131.0, 132.8, 145.5, 146.0, 154.3, 166.9; HRMS (ESI+): calcd $C_{18}H_{23}N_4O_2$ [M + H]$^+$ 327.1821, found 327.1829 (error 2.4 ppm). |
| 422 | 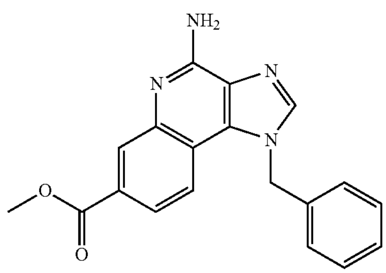 [SMILES: COC(=O)c1ccc2c(c1)nc(N)c1ncn(Cc3ccccc3)c12] | 4-amino-1-benzyl--7-methoxycarbonyl-1H-imidazo[4,5-c]quinoline | $^1$H NMR (DMF-$d_7$, 600 Hz) δ 3.91 (s, 3H), 6.07 (s, 2H), 6.86 (br s, 2H), 7.24-7.28 (m, 3H), 7.32-7.40 (m, 2H), 7.62 (dd, J = 9.0, 1.2 Hz, 1H), 8.04 (d, J = 9.0 Hz, 1H), 8.26 (d, J = 1.2 Hz, 1H), 8.54 (s, 1H); $^{13}$C NMR (DMF-$d_7$, 150 Hz) δ 50.2, 51.9, 118.4, 120.7, 121.5, 126.6, 127.9, 128.2, 128.3, 129.2, 130.4, 132.2, 137.2, 144.7, 145.2, 153.5, 166.9; LRMS (APCI+): calcd $C_{19}H_{17}N_4O_2$ [M + H]$^+$ 333.1, found 333.2. |
| 538 | 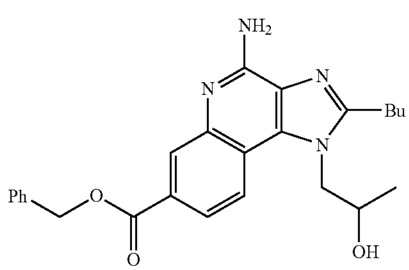 | 4-Amino-2-butyl-1-(2-hydroxypropyl)-7-benzyloxycarbonyl-1H-imidazo[4,5-c]quinoline | $^1$H NMR (DMSO-$d_6$, 400 Hz) δ 8.22 (s, 1H), 8.12 (d, J = 8.61, 1H), 7.78 (d, J = 8.49, 1H), 7.59-7.31 (m, 5H), 6.68 (s, 2H), 5.08 (d, J = 4.30, 1H), 4.55 (d, J = 13.30, 1H), 4.31 (dd, J = 9.0, 14.87, 1H), 4.03 (m, 1H), 2.96 (t, J = 7.43, 2H), 1.81 (pentet, J = 7.43, 2H), 1.45 (sextet, J = 7.24, 2H), 1.26 (d, J = 5.87, 3H), 0.95 (t, J = 7.43, 3H). $^{13}$C (DMSO-$d_6$, 100 MHz): δ 165.9, 155.4, 152.5, 144.0, 136.1, 132.1, 128.6, 128.1, 127.9, 126.8, 120.8, 118.3, 66.1, 65.4, 52.1, 29.3, 26.6, 22.0, 21.0, 13.8. HRMS (APCI+): calcd $C_{25}H_{29}N_4O_3$ [M + H]+ 433.2234, found 433.2234 (error 0.07 ppm). |

| Cmpd # | Structure | Name | Characterization |
|---|---|---|---|
| 540 | 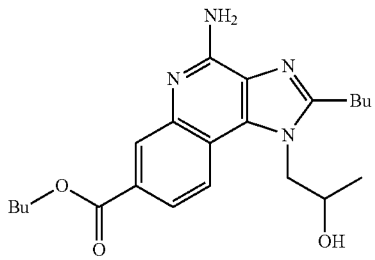 | 4-Amino-2-butyl-1-(2-hydroxypropyl)-7-butoxycarbonyl-1H-imidazo[4,5-c]quinoline | $^1$H NMR (DMSO-$d_6$, 400 Hz) δ 8.18 (s, 1H), 8.11 (d, J = 8.6, 1H), 7.74 (d, J = 8.7, 1H), 6.65 (s, 2H), 5.07 (d, J = 4.89, 1H), 4.56 (m, 1H), 4.31 (m, 1H), 4.03 (m, 1H), 2.97 (t, J = 7.83, 2H), 1.82 (pent, J = 7.83, 2H), 1.73 (pent, J = 7.83, 2H), 1.46 (sextet, J = 7.43, 2H), 1.27 (d, J = 6.06, 3H), 1.01-0.91 (m, 6H). $^1$H NMR (DMSO-$d_6$, 100 Hz) δ 166.1, 155.3, 152.5, 144.1, 132.0, 127.7, 127.6, 127.1, 120.7, 120.4, 118.2, 65.4, 64.2, 52.0, 30.3, 29.3, 26.6, 22.0, 21.0, 18.9, 13.8, 13.6. HRMS (APCI+): calcd $C_{22}H_{31}N_4O_3$ [M + H]+ 399.2391, found 399.2408 (error 4.19 ppm). |

EXAMPLE 5

Figure 34:
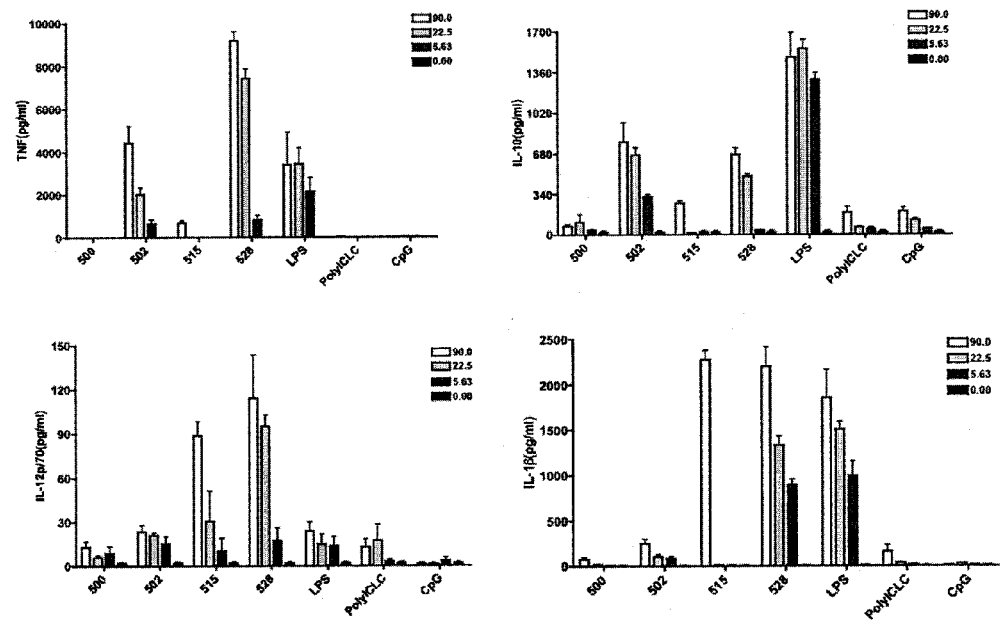
FIG. 34 shows results from Example 5 for compound 528.
Figure 35:
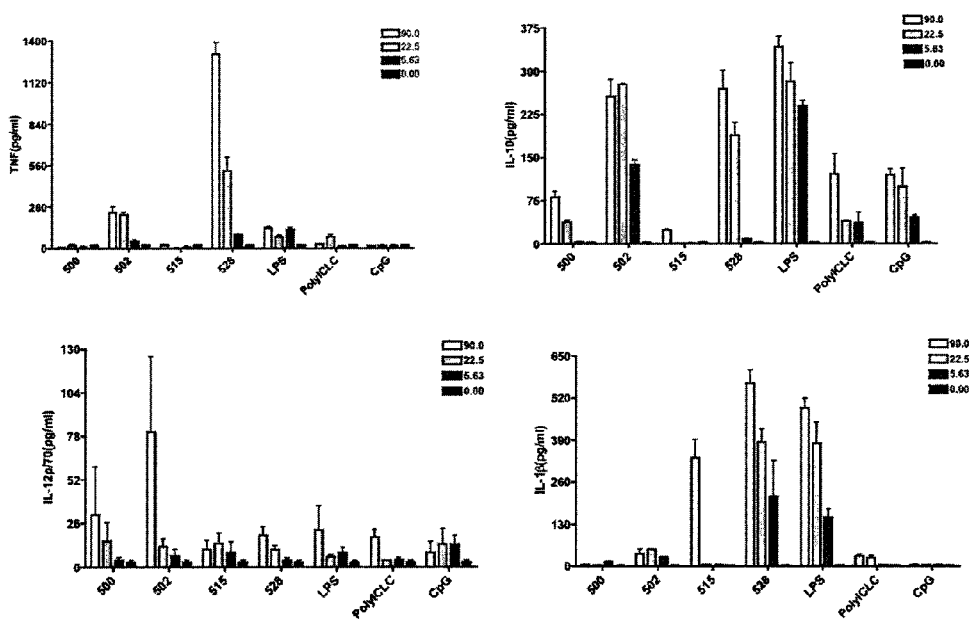
FIG. 35 shows results from Example 5 for compound 528.

Evaluation of the Effects of Representative Compounds on Human Monocyte-Derived Dendritic Cells and PBMC Cells Materials and Methods
1. Dendritic cells were generated from peripheral blood monocytes as described (Brossart P, et al. Blood. 1998; 92: 4238-4247). In brief, CD14 positive monocytes were from a healthy human peripheral blood mononuclear cells (PBMC) obtained via isolation with Lymphocyte Separation Medium (Mediatech, Inc, Manassas, Va.) and after purification with CD14 microbeads from Miltenyi Biotec Inc (Aubun, Calif.). The CD14 positive monocytes (>95% CD14) were cultured into immature monocyte-derived dendritic cells (MoDC) by further 6 day culture with GM-CSF (100 ng/ml) and IL-4 (100 ng/ml)(R&D, MN).
2. 0.1 million of MoDC were plated into 96-well plate and stimulated for 48 hours with 5 different concentration of following TLRs: 412, 420, 421, 414 and 415 at concentration of 0, 0.325, 1.3, 5.2 and 20.8 nmol/ml in triplicate. In other experiments (FIGS. 34 and 35), fresh PBMC (not DC) were used as the responder cells to the indicated compounds and cytokines levels were measured by bead array according to the manufacture's protocol (BD biosciences).

Immunostaining and Flowcytometric Analysis:
48 hours after stimulation, the cells were stained with anti-HLA-DR, CD11c, CD-86, CD80, CD83, CD8a, CD123 and relevant isotype control (eBioscience, San Diego, Calif.). The cells were loaded on FACS-canto II and analyzed with FACSDiva and Flowjo Cytometric Bead Assay (CBA):
The supernatant were harvested 48 hours after stimulation with TLRs. Inflammatory cytokines level was identified with CBA, following the producer's instruction (BD, San Jose, Calif.)

Results
Results are shown in FIGS. 3-15 and can be summarized as follows. See FIG. 16 for the structures of test compounds.
Compound 420 enhanced MoDC maturation by raising CD86 of co-stimulator level and CD83 on human MoDC with the same efficiency as Resiquimod and significantly stronger than imiquimod.
Compound 420 induced higher production of "inflammatory cytokines", compared to imiquimod (but less stronger than Resquimod). So Compound 420 seems to be safer than Resiquimod if used in a larger dose or if used systemically.
One unique biological function of Compound 420 is induction of IL-1β that is a critical molecule of alarming system when senses an invading microorganism.
Resiquimod showed a unique effect on MoDC that changes myeloid DC into plasmacytoid DC.
If we can explain clearly the signal pathway base of two unique functions, it maybe a novel discovery in immune modulation between TLRs and DC phenotypes.

EXAMPLE 6

Evaluation of IL-6 Level after Stimulation with Compounds of the Invention

Material and Method
TLR7 mutant mice and C57BL/6j mice, 8-12 weeks old, were obtained from Jackson Lab (Bar Harbor, Me.). TLR7 mutant gene was introduced to 129S1/Sv derived from CJ7 embryonic stem cells. The cell line was backcrossed ten times to C57BL/6Ncr. No TLR7 RNA expression is detected in bone marrow-derived macrophages. The homologues TLR7 mutant mice were developed from backcrossing heterologous mutant mice with wild type C57BL/6j in our Lab. All animals were housed under specific pathogen-free condition and cared for in accordance with the guidelines of University of Minnesota Resource Animal Research.

Single cell suspension of splenocytes from C57BL/6j or TLR7 mutant mice was isolated after whole spleen was squeezed through 70 um cell strainer and red blood cell lysis process. Splenocytes were pulsed in triplicate with 2.08 nmol/ml or 20.8 nmol/ml of Imiquimod (IMQ), hydroxyl Imiquimod (IMQ-OH) or 10 ug/ml of CpG685 in complete RPMI-1640 medium (10% heat-inactivated FBS, glutamine, 1% penicillin/streptomycin, 55 nmol 2-ME, 10 mmol HEPES). Supernatant from the culture medium was harvested 12 hours and 24 hours after pulsing and frozen at −80° C. until detection. A cytometric bead array (BD Biosciences, San Jose, Calif.) were used for measurement of IL-6 level according to the manufacture's instruction. An analysis was performed on FACScanto-II machine with FACSAria II software and further analyzed with Flowjo software (Tree Star, Inc, Ashland, Oreg.). Standard curves and negative control (PBS) were included for calculation of the cytokine concentration in the samples.

Screening Binding Ability of Various Compounds of the Invention to TLR7/8 Cells In Vitro A TLR7 or TLR8 positive cell lines, HEK-Blue TLR cells (Invivogen, San Diego, Calif.), were used for this screening assay. HEK-Blue TLR cells are engineered HEK293 cells. They stably express TLR gene and an inducible NF-kB-SEAP (secreted embryonic alkaline phosphase) report gene. Bounding of ligands with TLR in HEK-Blue cells induces SEAP that has pNPP substrate of phosphase becoming blue. Screening assays were conducted following the manufacture's instruction. Imiquimod-derived new TLR ligand compounds, 410, 411, 412, 413, 420, 421, IMQ (414), IMQ-maleimide (551) and Resquimod (415) at 20.8 nmol/ml or 5.2 nmol/ml concentration, were added in triplicate in HEK-Blue-TLR7 or TLR8 cells, cultured at 37° C. and 5% $CO_2$ condition. 24 hours later, 5 ul of supernatant of cultures was mixed with 200 ul of pNPP-included detection medium. After one hour SEAP activity was read out as OD at 650 nm with a microplate reader (BioTek Synergy 2, Vermont). No compound solvent (PBS+<1% DMSO) negative control was included.

Inflammatory Cytokine Detection in BMDC and Splenocytes

Bone marrow cells were harvested from femurs and tibias of C57BL/6j. After red blood cells were removed with ammonium-chloride-potassium buffer, the bone marrow cells were cultured with complete RPMI-1640 medium and 2 ng/ml of granulocyte macrophage colony-stimulating factor (GM-CFS) at 5% $CO_2$ and 37° C. for 6 days. Medium was changed twice during 6 days culture. Single cell suspension of splenocytes was prepared in the same way as one in IL-6 detection assay. BMDC or splenocytes were stimulated in triplicate with Imiquimod-derived new TLR ligand compounds, 412, 420, 421, 422, IMQ (414) and Resquimod (415) at various concentration of 20.8 nmol/ml, 5.2 nmol/ml, 1.3 nmol/ml, 0.325 nmol/ml and 0 nmol/ml. 48 hours after stimulation, the supernatants were harvested and frozen at −80° C. until detection. A cytometric bead array (CBA, BD Bioscience) was performed on inflammatory cytokines following the manufacture's instruction. 500 events were collected. Analysis of all samples was performed on FACScanto-II machine with software and further analyzed with Flowjo. Standard curves and negative control (PBS) were included for each cytokine to calculate the cytokine concentration in the samples.

Detection of Co-Stimulator Level on BMDC

Two days after stimulation with compounds, the BMDC were stained in triplicate with different fluorocore-labeled antibodies obtained from eBioscience (San Diego, Calif.). The antibodies include anti-MHC-II (I-A/I-E, clone M5/114.15.2), anti-CD86 (clone GL1), anti-CD80 (clone 16-10A1), anti-CD8α(clone 53-6.7), anti-CD11 b (clone, M1/70), antiCD-205 (clone 205yekta), anti-CD3 (clone 17A2) and anti-CD11c (clone N418). All samples were acquired on a FACScanto II flow cytometer (BD Biosciences, San Jose, Calif.). Between 50,000 and 100,000 events were collected. All data were analyzed with Flowjo software (Tree Star, Inc, Ashland, Oreg.). Gate is based on CD3-CD11c+ population.

Proliferation of Pmel CD8 and IFNγ Production after Cross-Presentation

BMDC from C56BL/6j and single cell suspension of splenocytes from pmel mice (T-cell receptor transgenic mice containing human $gp100_{25-33}$ \H2 Db specific receptors, Jackson Lab) were prepared as above. BMDC were pulsed in triplicate with 3.5 ug of human gp100 peptide per well (CAL-LAVGATKVPRNQDWLGVSRQLRTK, GenScript, Piscataway, N.J.) and various IMQ-derived new TLR7 ligands (412, 420, 421, 422, IMQ, and Resquimod) at the concentration of 10.4 nmol/ml and hgp100 peptide control and PBS negative control for 48 hours. BMDCs were washed twice with complete RPMI medium and followed by coculture with pmel CD8 splenocytes CFSE-labeled that were isolated from pmel splenocytes with CD8+ T Cell isolation Kit (Miltenyi Biotec, Auburn, Calif.) at a ratio of 1:3 of DC/CD8. Four days after coculture, supernatants were harvested and frozen at −80° C. until detection of INFγ with CBA kit. CBA for IFNγ measurement was conducted according to manufacture's instruction. The cell pellets were washed and stained with fluoro-core-labeled antibodies, all of which were obtained from eBioscience. They are anti-CD3 (clone, 17A2) and anti-CD8α(clone 53-6.7). Flowcytometric data were acquired from the stained samples on FACSCanto II flowcytometer and analyzed with Flowjo software. Gate was from CD3+ CD8+ population.

IL-2 Production of OT-I Cells after Stimulation with IMQ-Derived New TLR7 Ligands Single cell suspension of C57BL/6j was prepared as previously. The cells were pulsed in triplicate with new IMQ-derived TLR7 ligands at 20.8 nmol/ml concentration and added with and without 15 ug of ovalbumin (Sigma-Aldrich, St. Louis, Mo.) per well. Four days later, the cells were washed twice with complete RPMI medium and cultured with isolated OT-I CD8 T cells using CD8+ isolation Kit, (Miltenyl Biotec, Auburn, Calif.). After four days coculture, the supernatant were harvested and detected. CBA was conducted for IL-2 production according to BD Bioscience's instruction. Data were acquired on FACSCanto-II flowcytometer and 500 events were collected and analyzed with Flowjo software.

Results

Figure 4:
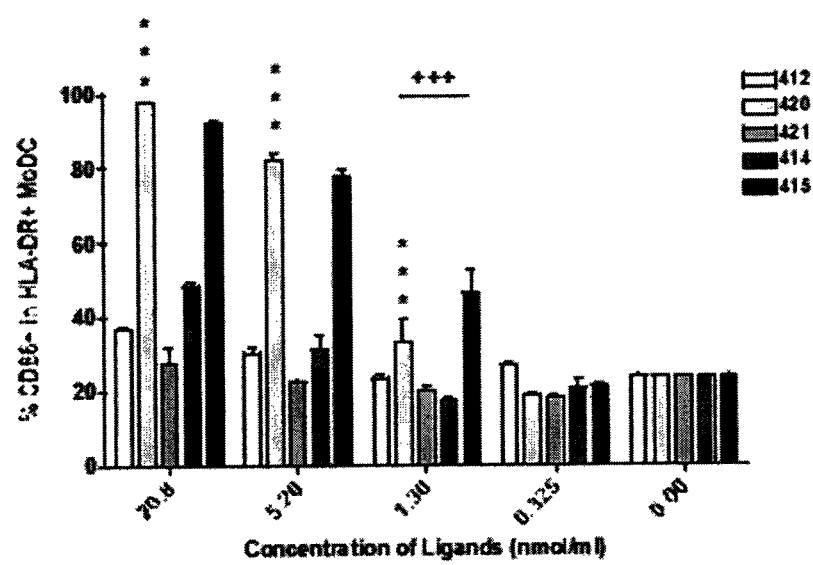
Figure 5:
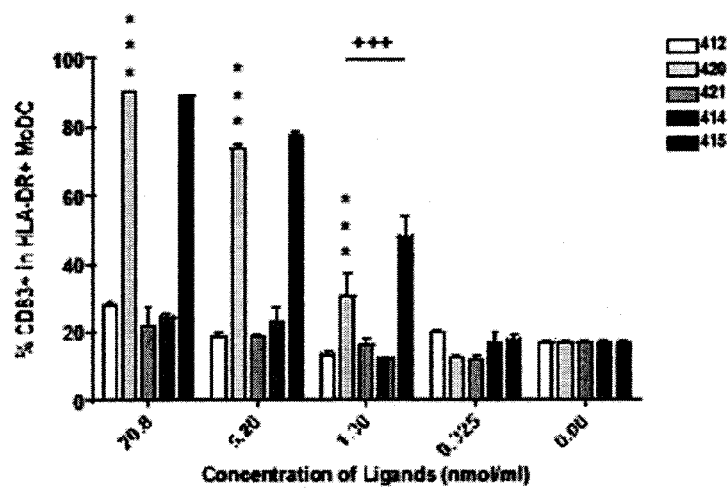
Figure 6:
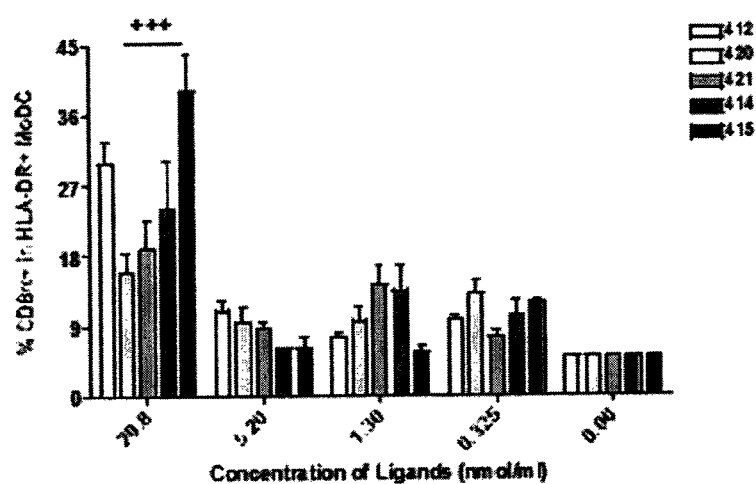
Figure 7:
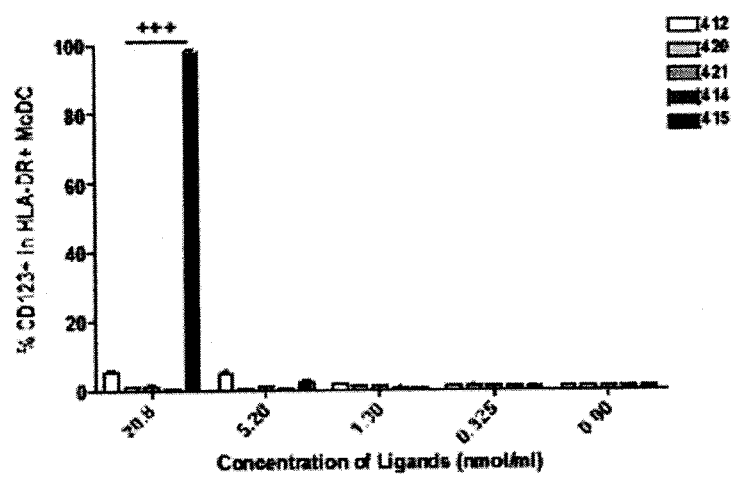
Figure 8:
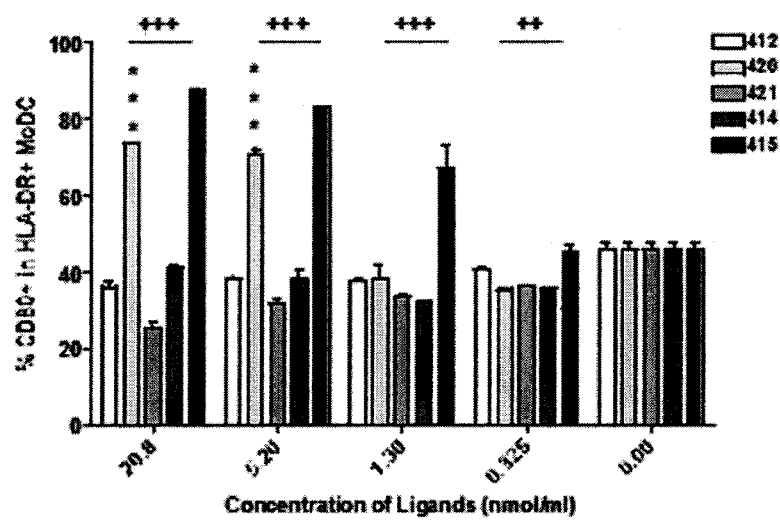
Figure 9:
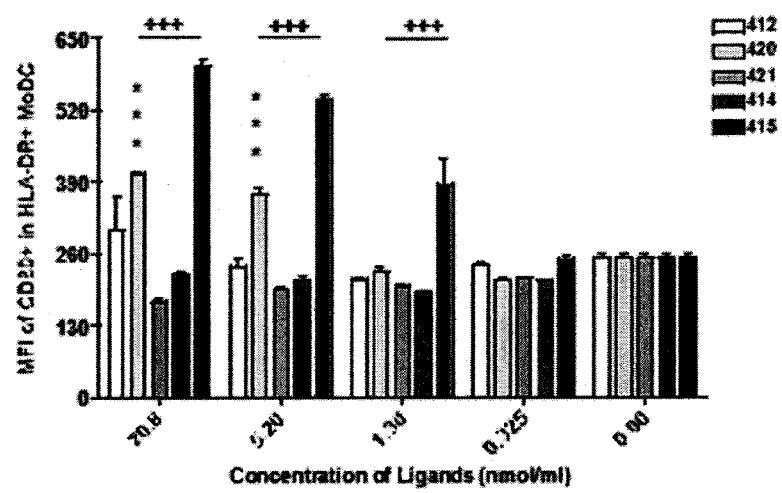
Figure 10:
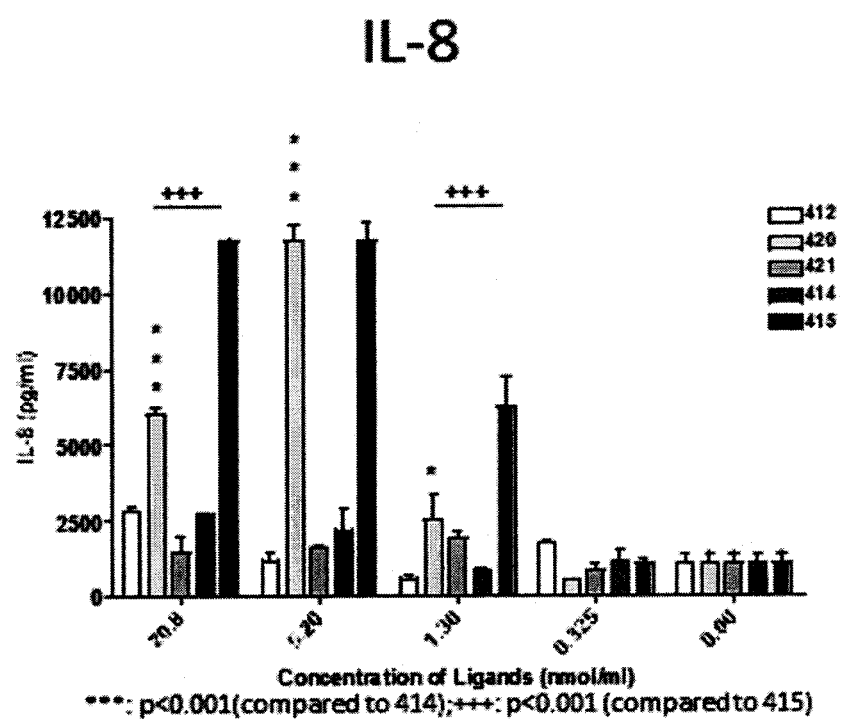
Figure 11:
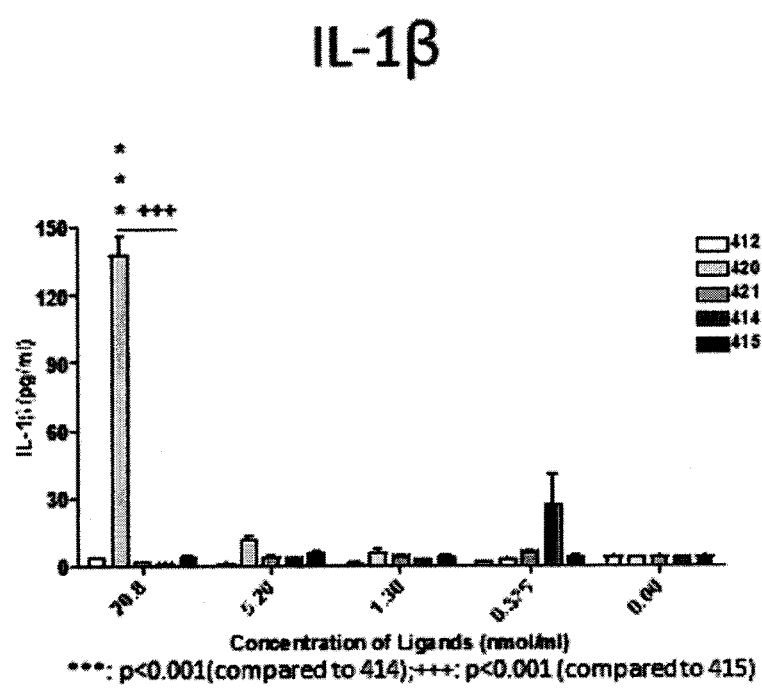
Figure 12:
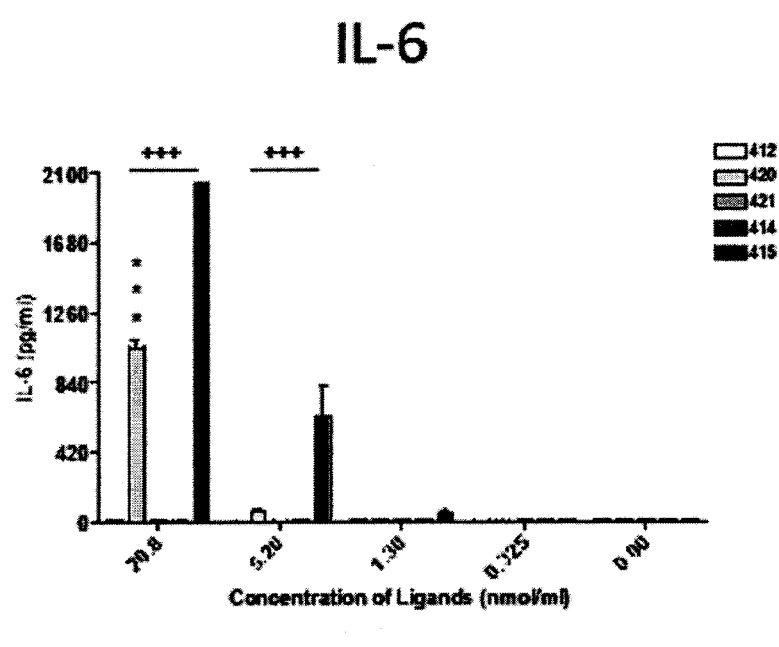
Figure 13:
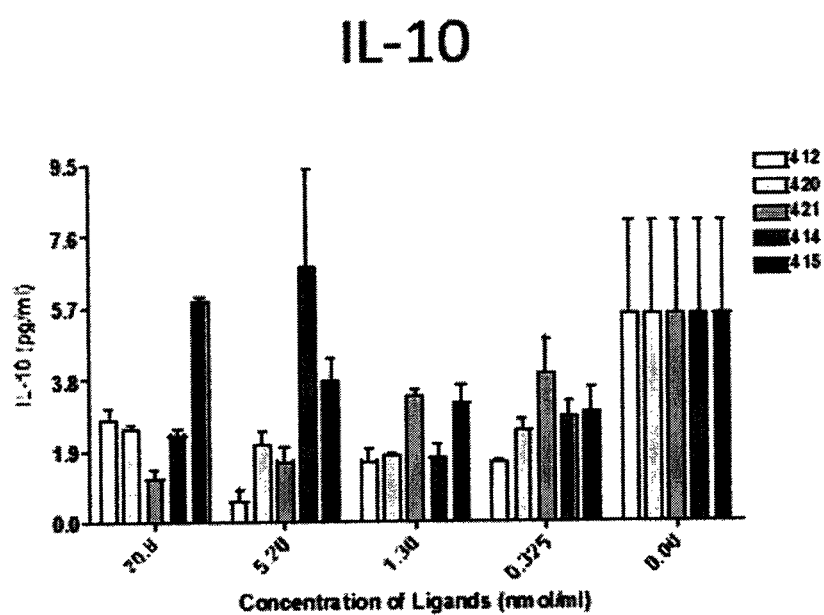
Figure 14:
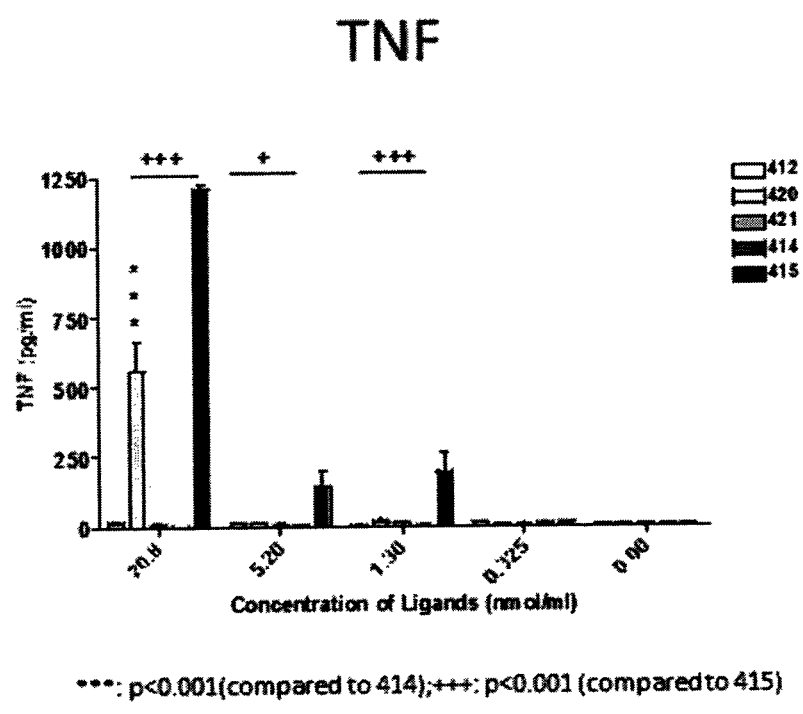
Figure 15:
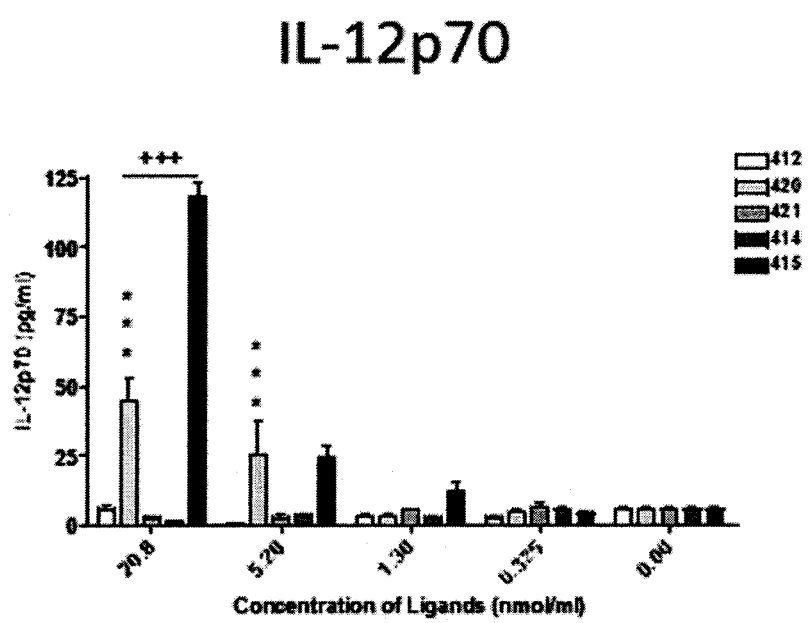
Figure 16:
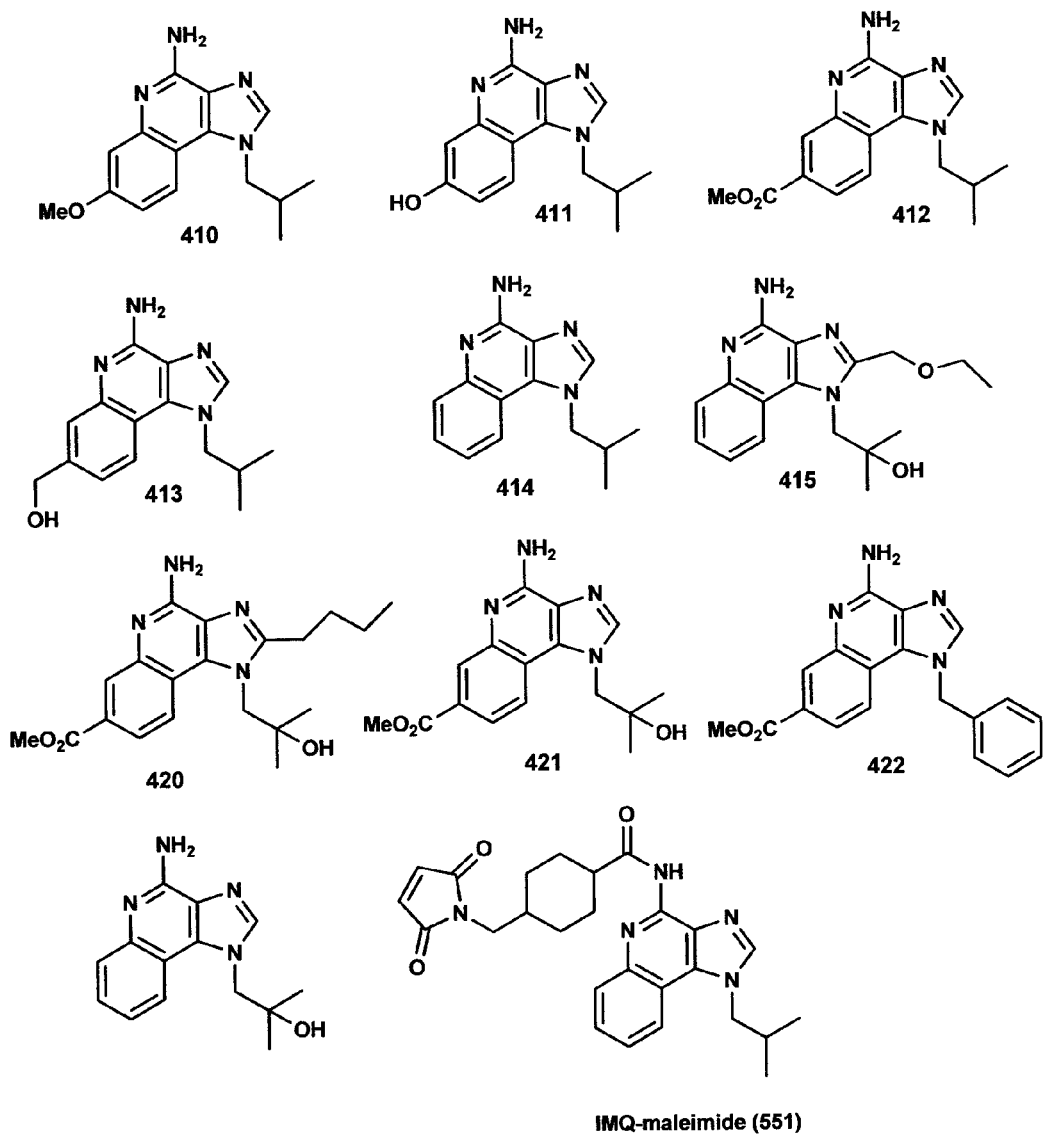
FIGS. 16-31 show results from Example 6.
Figure 17:
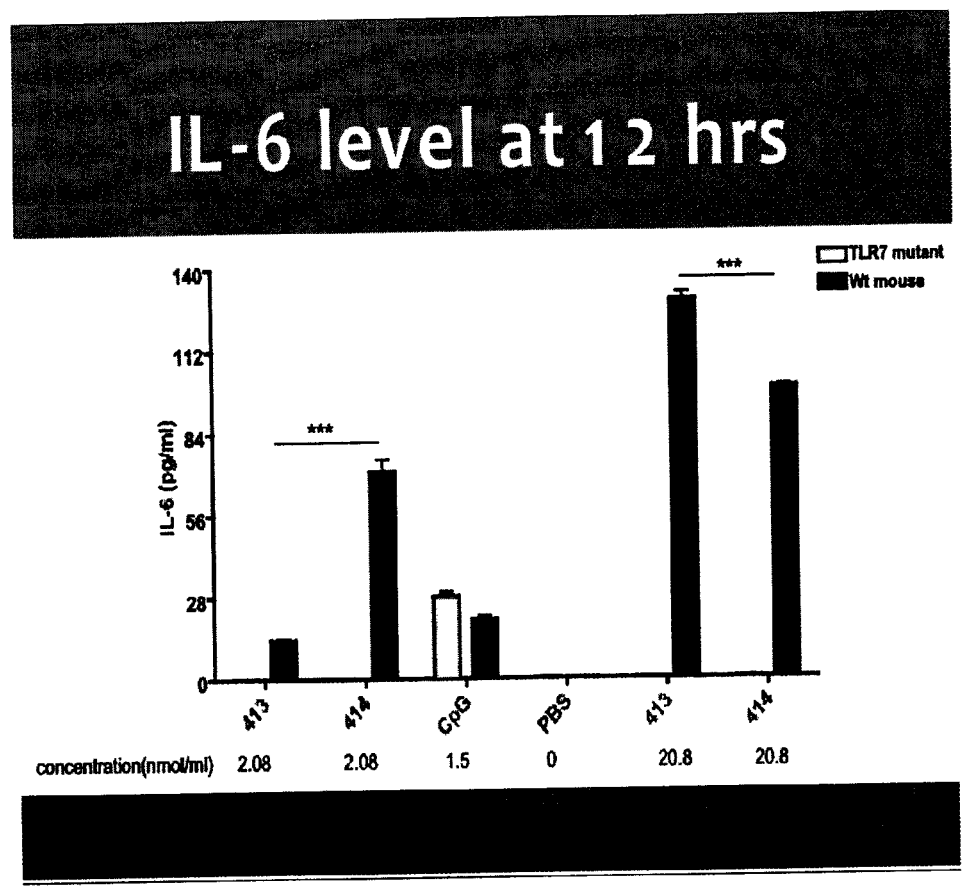
Figure 18:
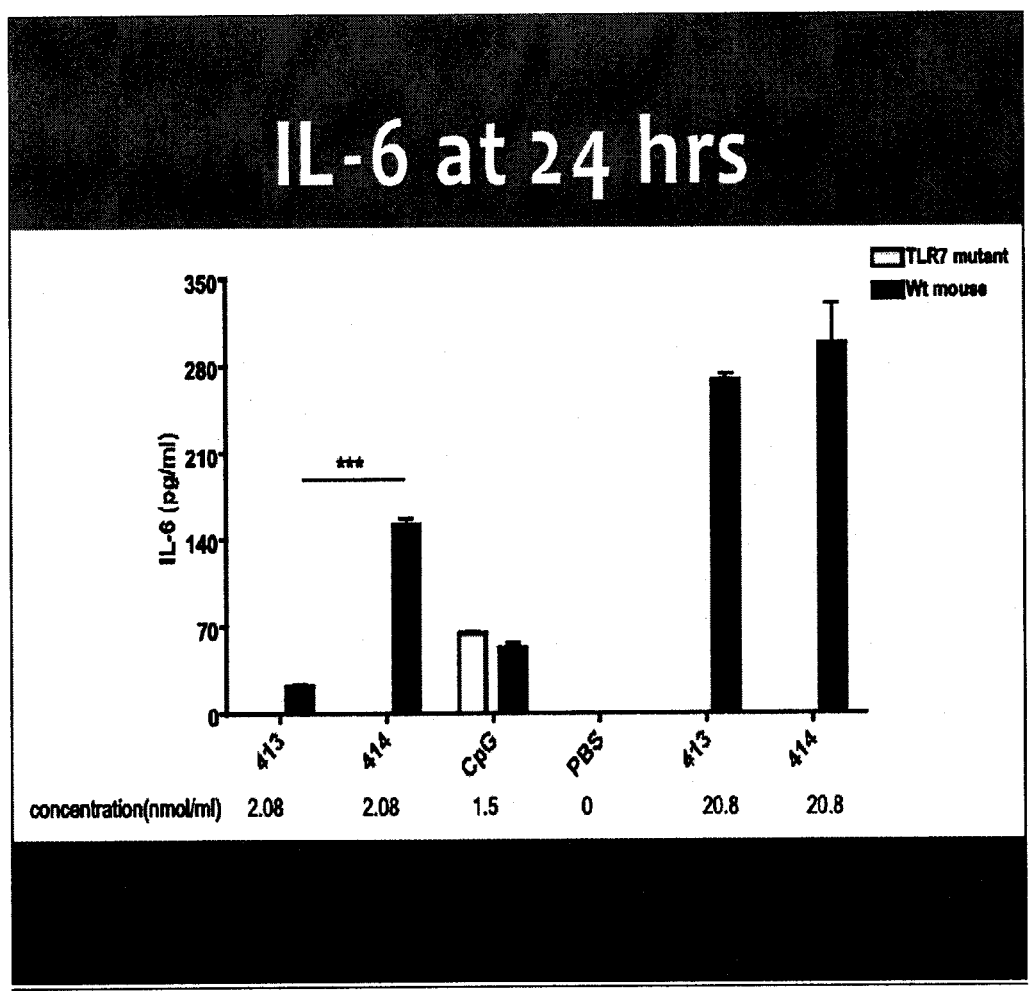
Figure 19:
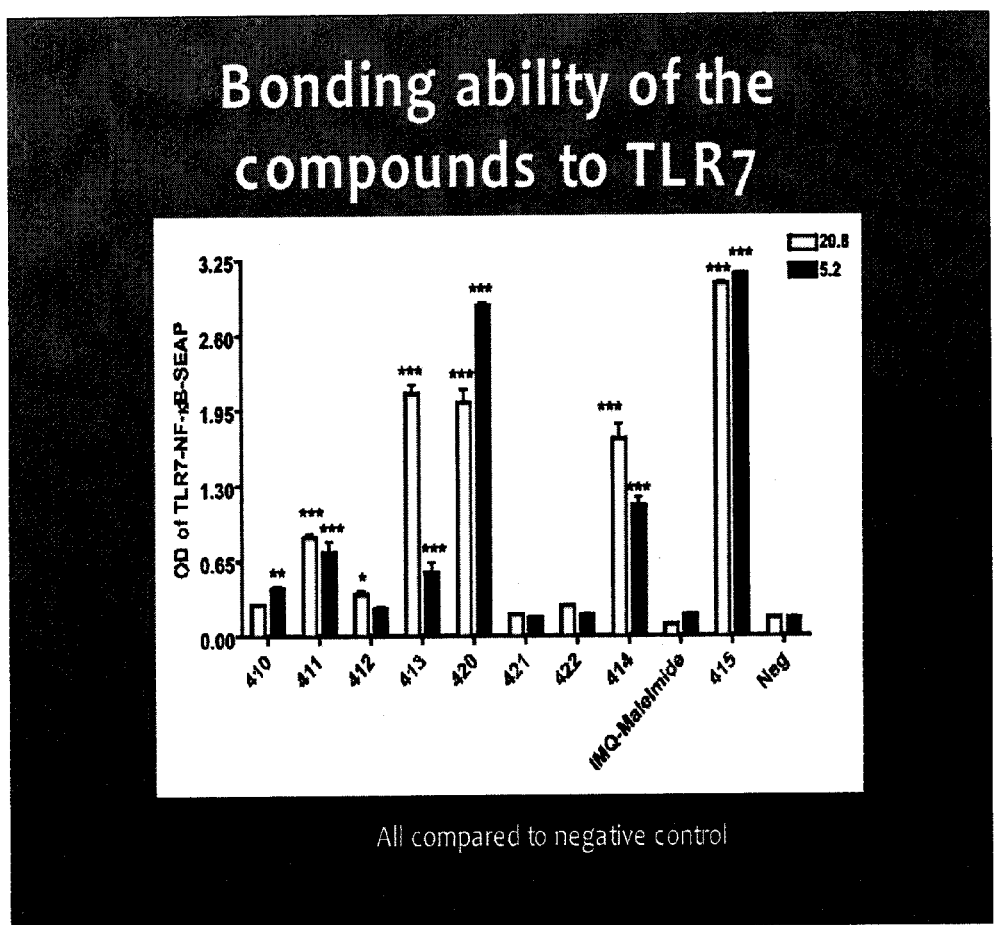
Figure 20:
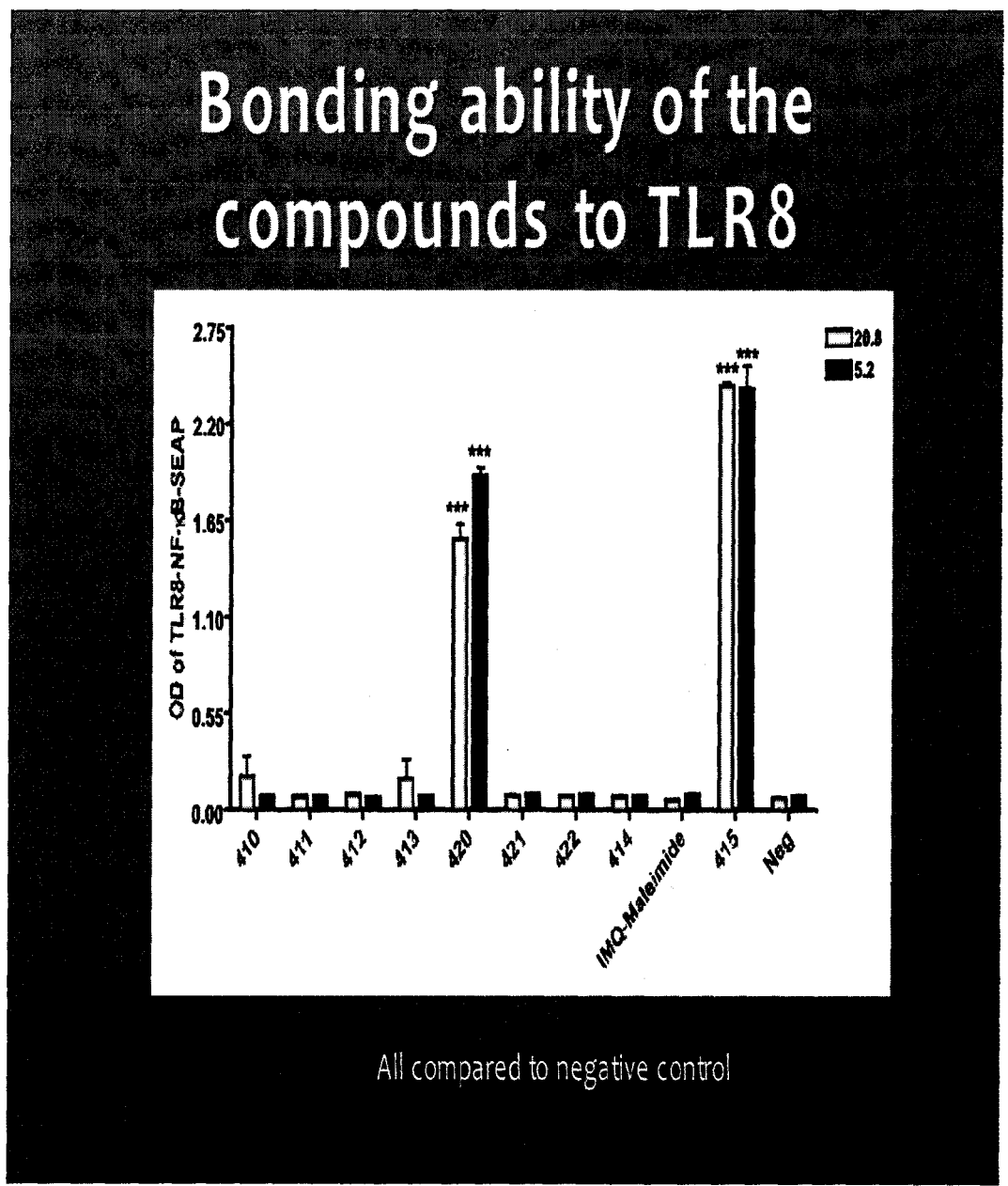
Figure 21A:
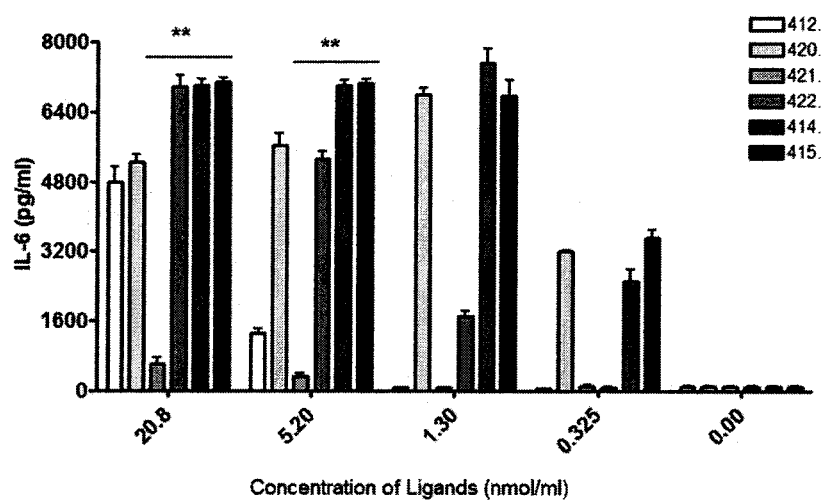
Figure 21B:
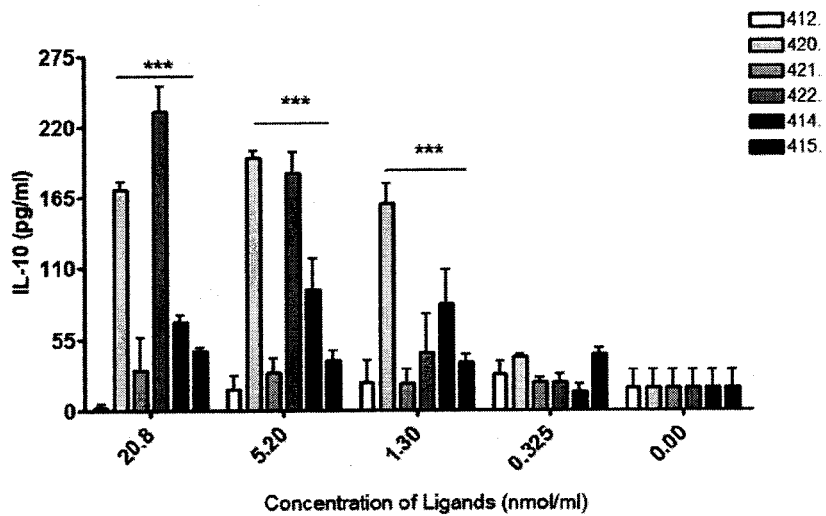
Figure 21C:
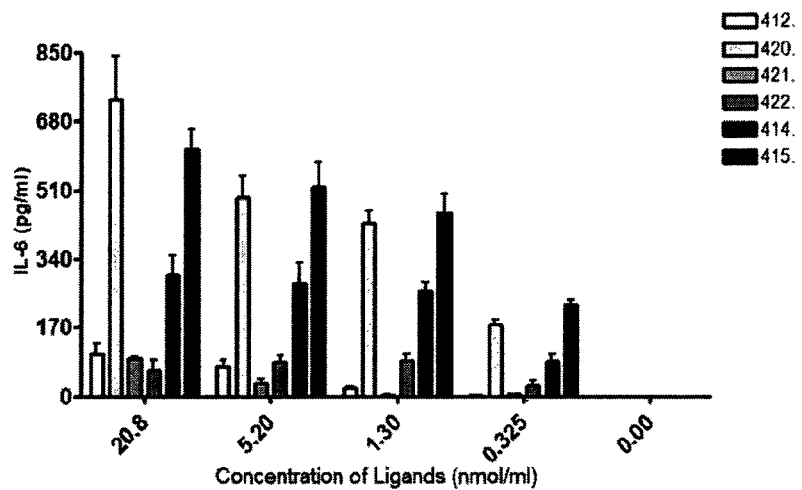
Figure 21D:
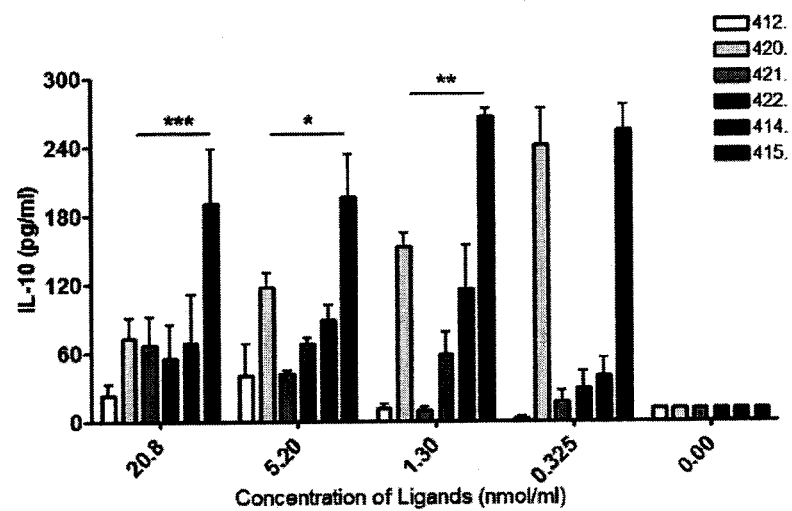
Figure 22A:
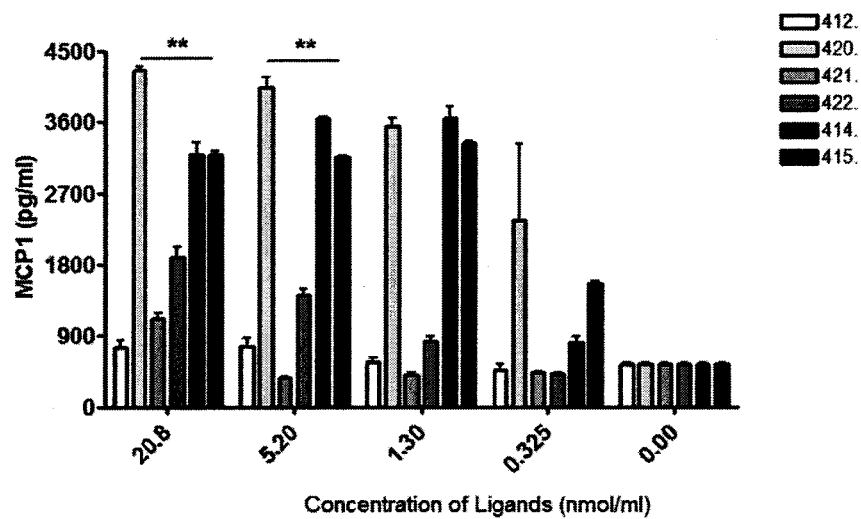
Figure 22B:
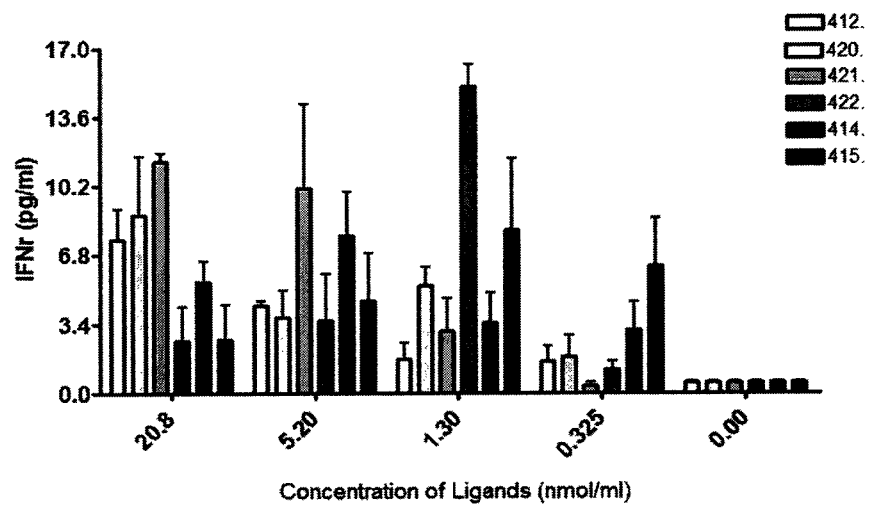
Figure 22C:
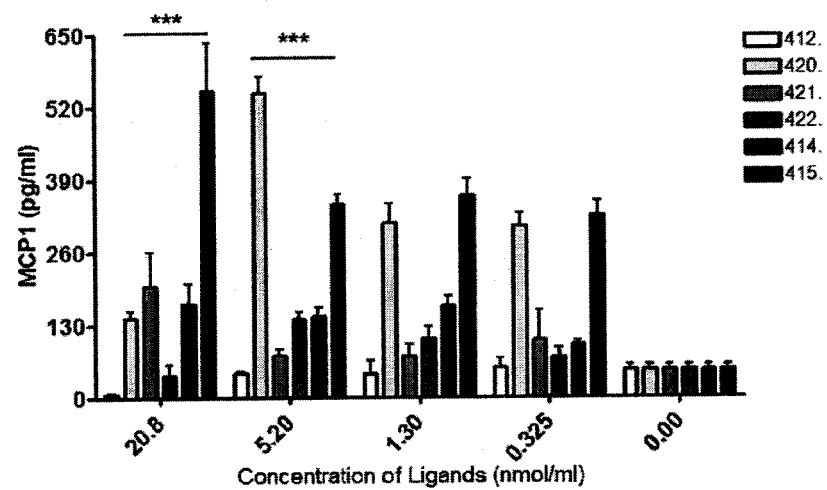
Figure 22D:
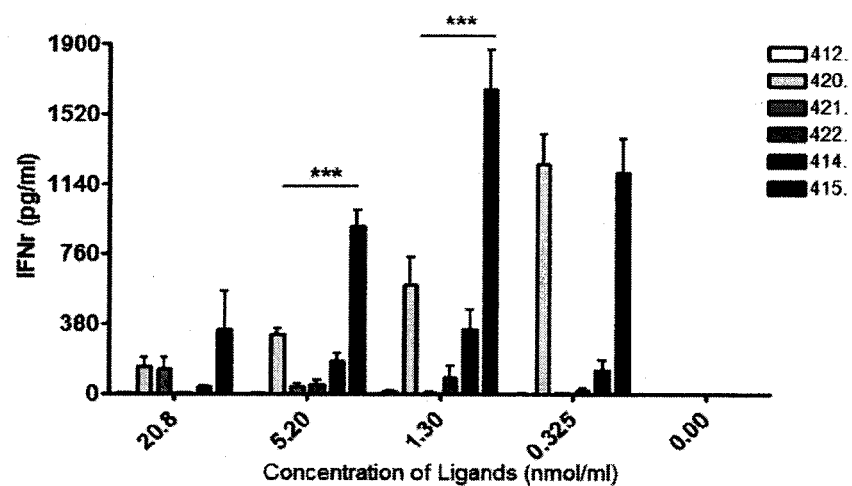
Figure 23A:
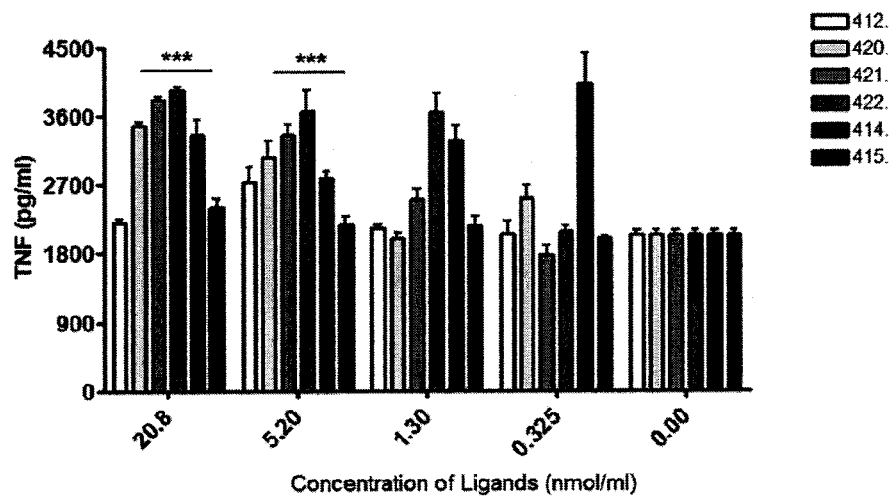
Figure 23B:
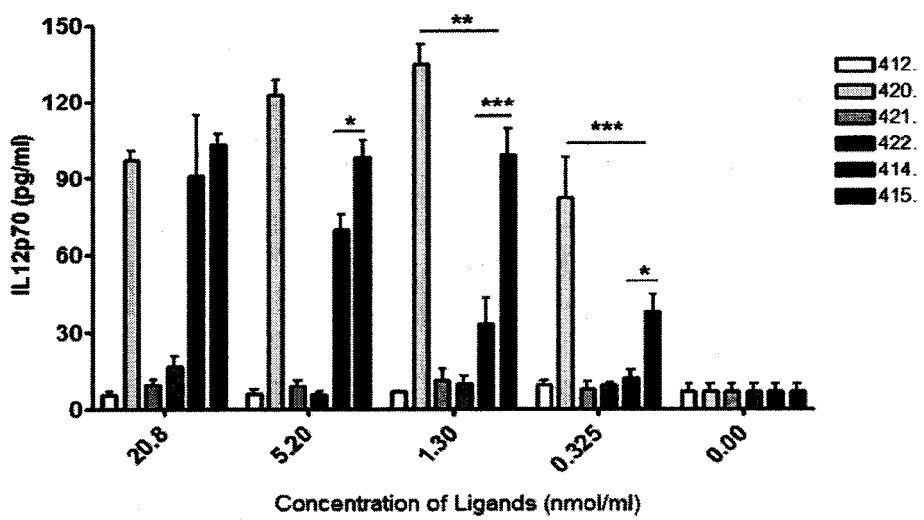
Figure 23C:
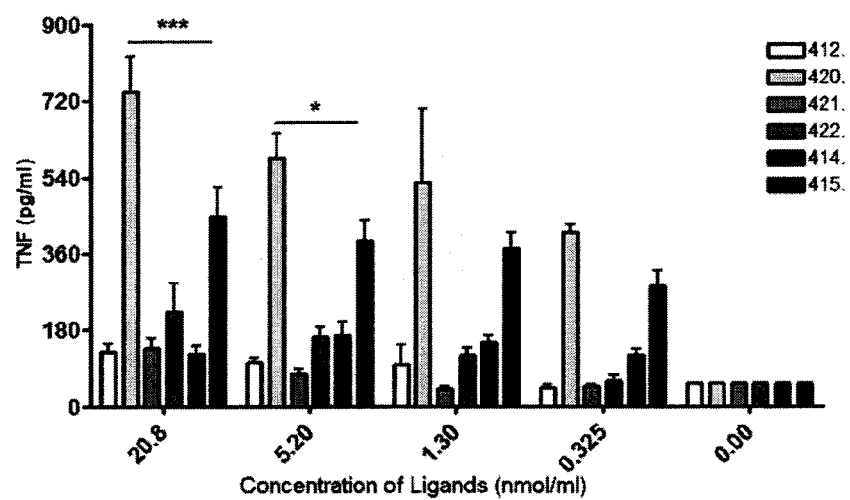
Figure 23D:
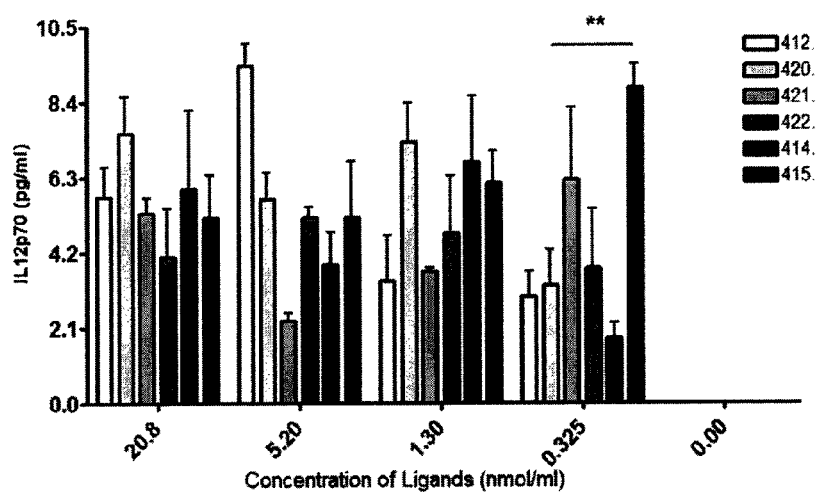
Figure 24:
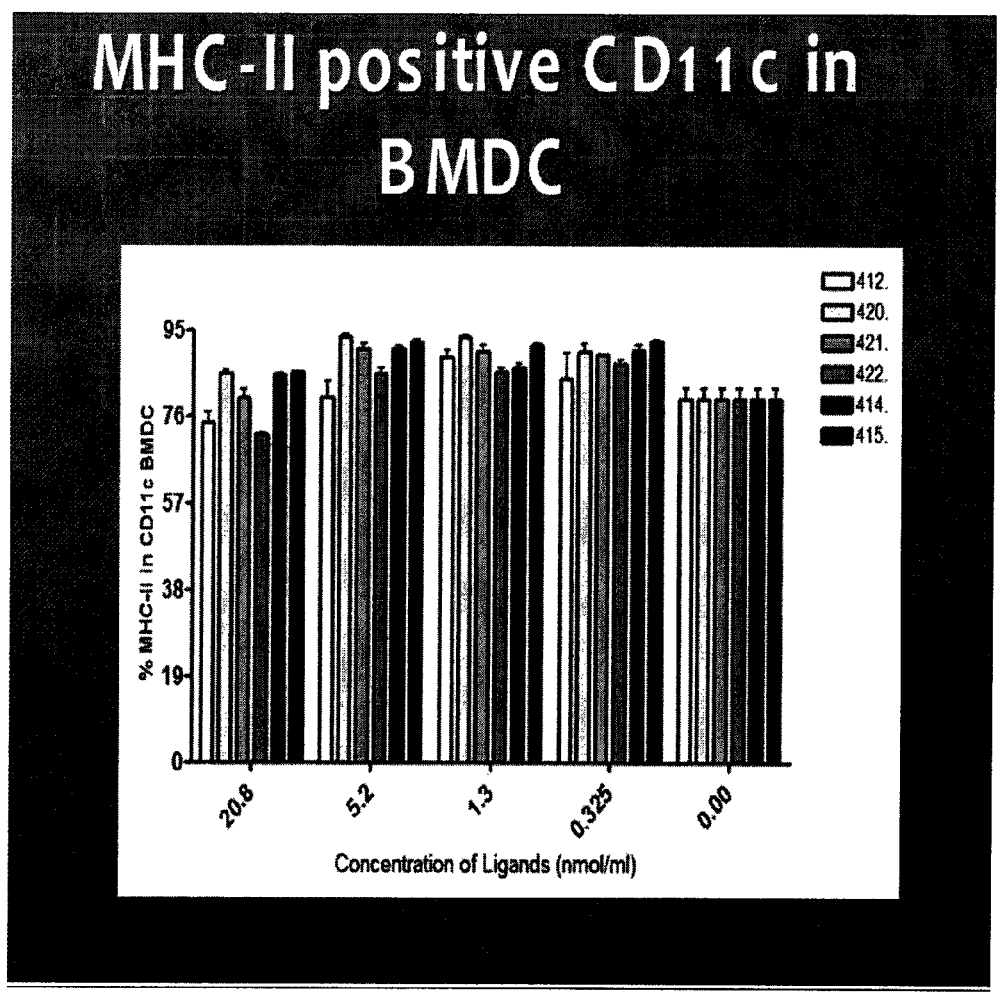
Figure 25:
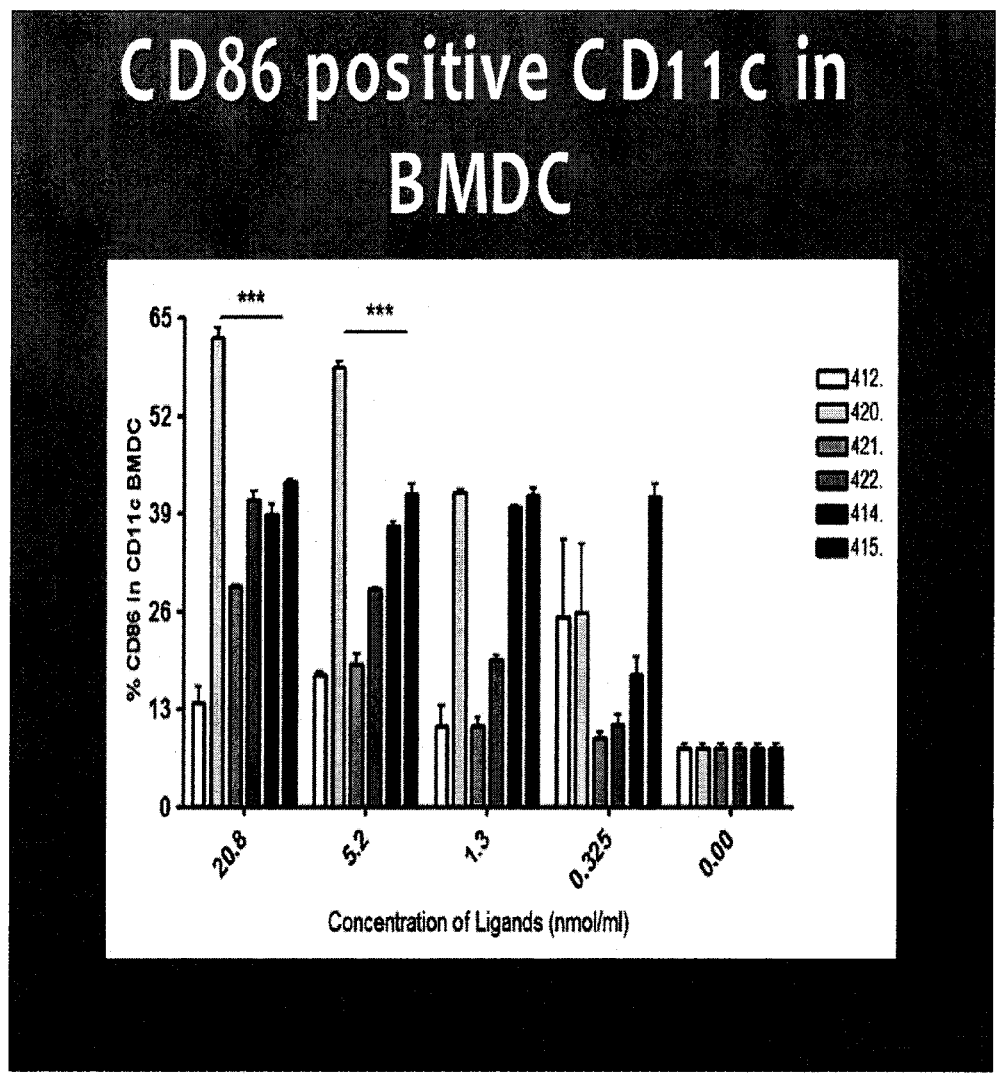
Figure 26:
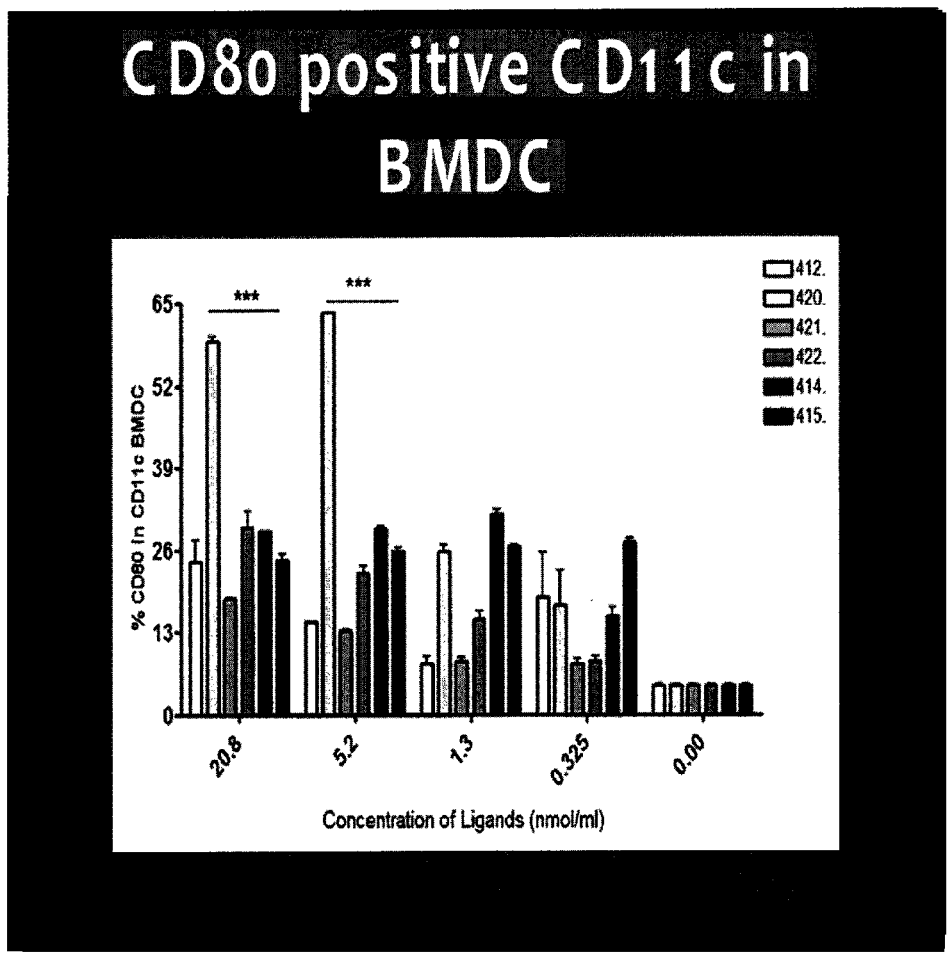
Figure 27:
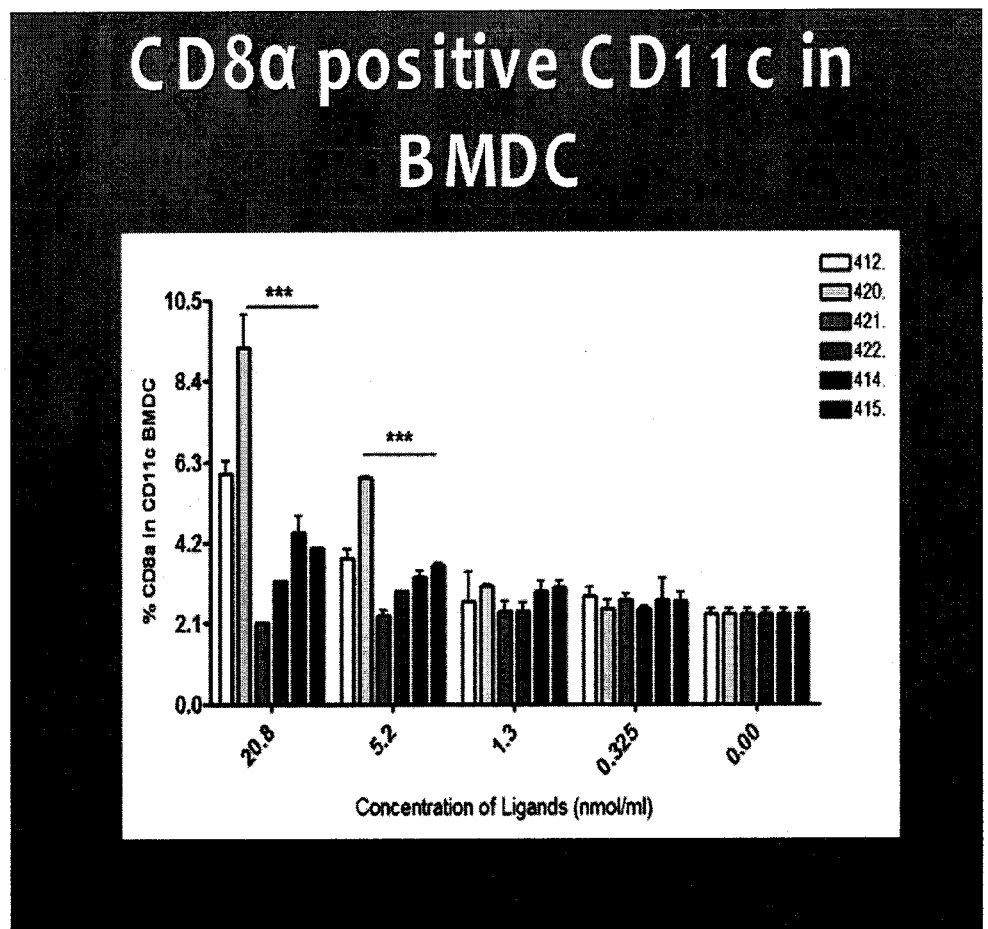
Figure 28:
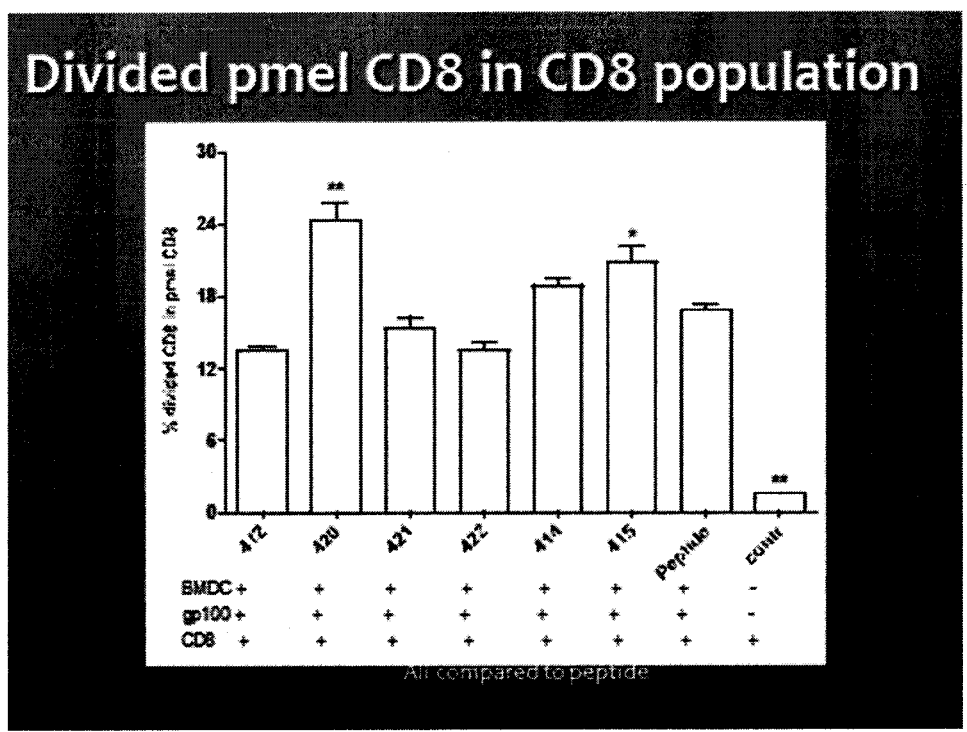
Figure 29:
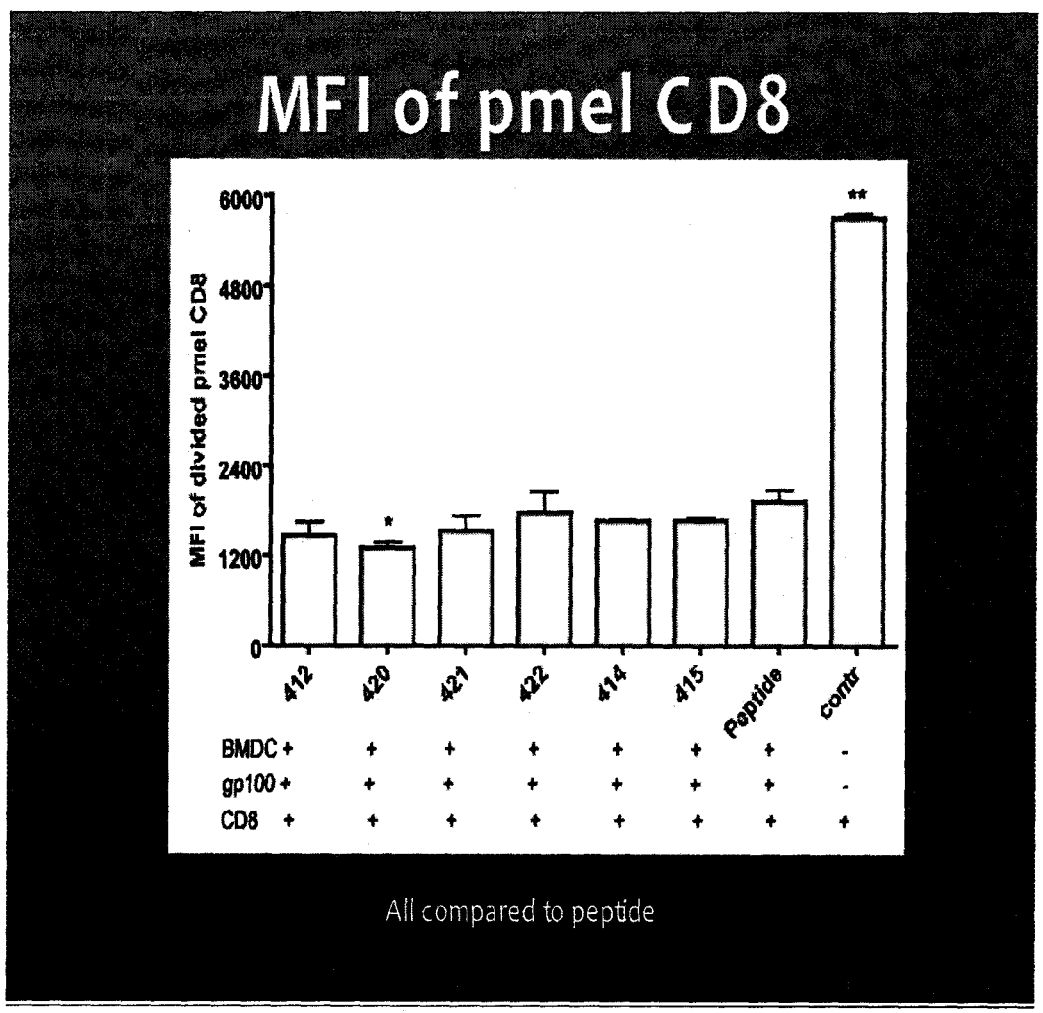
Figure 30:
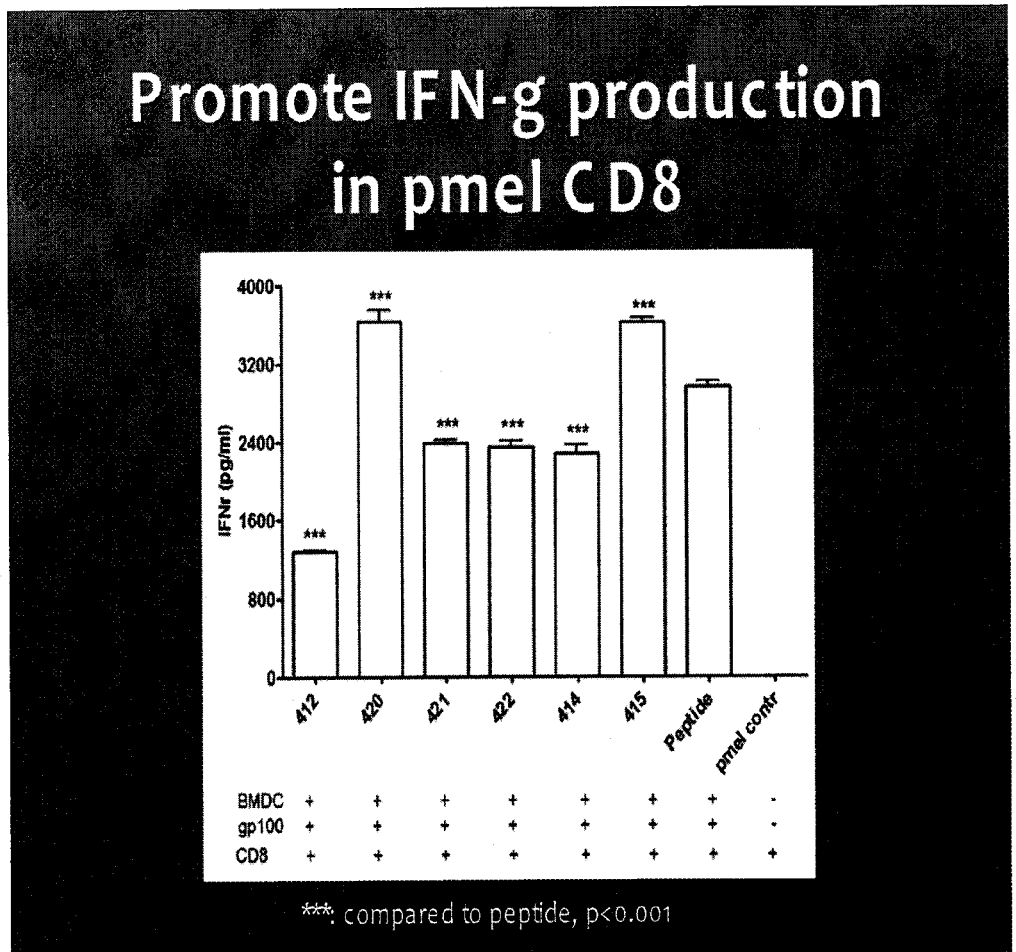
Figure 31:
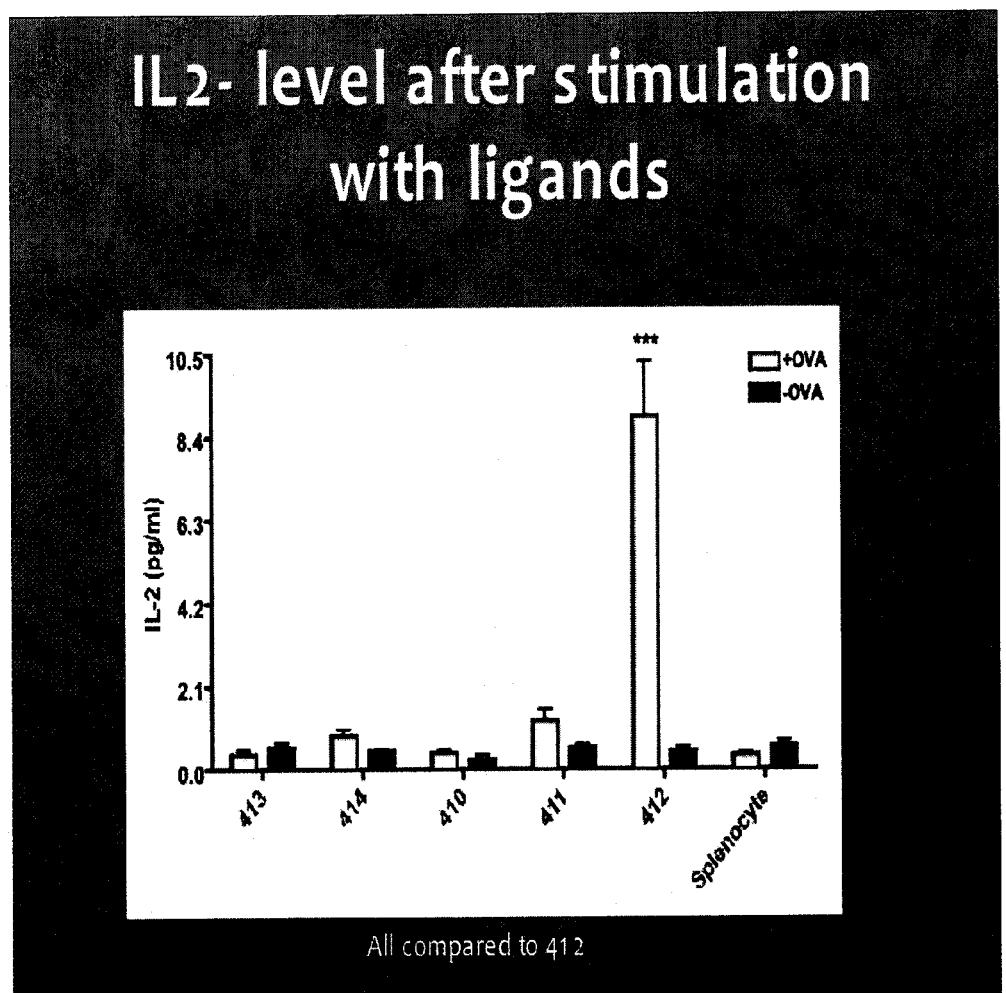

The structures of compounds which were evaluated are shown in FIG. 16. Results are shown in FIGS. 17-31. There are several key differences in activity that are expected to translate into clinically relevant differences in immune response between the present invention and resquimod or imiquimod. First, compound 420 caused significantly greater elaboration of proinflammatory TNFa compared to the other drugs (FIG. 23). Second, in mouse splenocytes, which is a complex mixture of immune cells as would be present in the body, compound 420 caused less IL-10 (anti-inflammatory) secretion compared to resquimod. Third, in human moDC, compound 420 was the only drug tested that caused appreciable IL-1b secretion (FIG. 11). In human moDC resquimod differentiated the cells into primarily CD123+ plasmacytoid DC whereas compound 420 did not (FIG. 4). All together, the data show that compound 420 induces unique cytokine and DC differentiation activity which is expected to change T cell and antibody responses to better target tumors and infectious agents.

EXAMPLE 7

Detection of GARC-1 Mutant-Specific CD8 T Cells in the Blood of Glioma-Bearing Mice Vaccinated with the Mutant Peptides (GARC-1, KRAS and p53) and Compound 522

Animal Model

C57BL/6 female mice (6-8 weeks old) were purchased from Jackson Laboratory and maintained in a specific pathogen-free facility according to the guidelines of the University of Minnesota Institutional Animal Care and Use Committee. The GL261 model was established in C57BL/6 mice by inoculation with 15,000 GL261 glioma cells in 1 µl PBS. Tumor cells were injected stereotactically into the right striatum; coordinates were 2.5 mm lateral and 0.5 mm anterior of bregma, and 3 mm deep from the cortical surface of the brain.

Vaccination Protocol

The animals received vaccinations on days 5, 8, 11, 14, 21, 28 and 35 after tumor inoculation. Each vaccine consisted of mutant peptides: GARC-1, KRAS and p53 (50 µg each peptide) mixed with annexin (2 µg) or 522 (50 µg) in a final volume of 150 µl and 200 µl, respectively, and injected subcutaneously in the hind flank on the right thigh. Using RNA-seq, a recently developed approach to transcriptome profiling that uses deep-sequencing technologies, we confirmed the presence in our GL261 glioma of point mutations in GARC-1 D81N and in p53 tumor suppressor R153P, and identified a new point mutation in KRAS oncogene G12C. We designed mutant peptides that encompass these point mutations: GARC-1 (FRVRASAALLNKLYAMGLVPT) (SEQ ID NO:1), KRAS (TEYKLVVVGACGVGKSALTIQ) (SEQ ID NO:2) and p53 (WVSATPPAGSPVRAMAIYKKS) (SEQ ID NO:3), and the peptides were synthesized by New England Peptide. Recombinant human Annexin II (ANX) was purchased from Serotec, and 522 was kindly provided by Dr. David Ferguson, Department of Medicinal Chemistry, University of Minnesota.

Flow Cytometry

Blood (50 µl) was collected from mice, from the retroorbital sinus, on days 17 and 25 after tumor inoculation, and whole blood cells were surface stained with fluorescent dye-conjugated antibodies. The following antibodies were used: Alexa Fluor 700-conjugated anti-CD3 (eBioscience), Pacific Blue-conjugated anti-CD8 (BioLegend), and PE-conjugated H-2D$^b$/GARC-1$_{77-85}$ tetramer (produced by the NIH Tetramer Core Facility at Emory University, Atlanta, Ga.). A Becton Dickinson Canto three-laser flow cytometer was used for data acquisition, and FlowJo software was used for data analysis.

Figure 32:
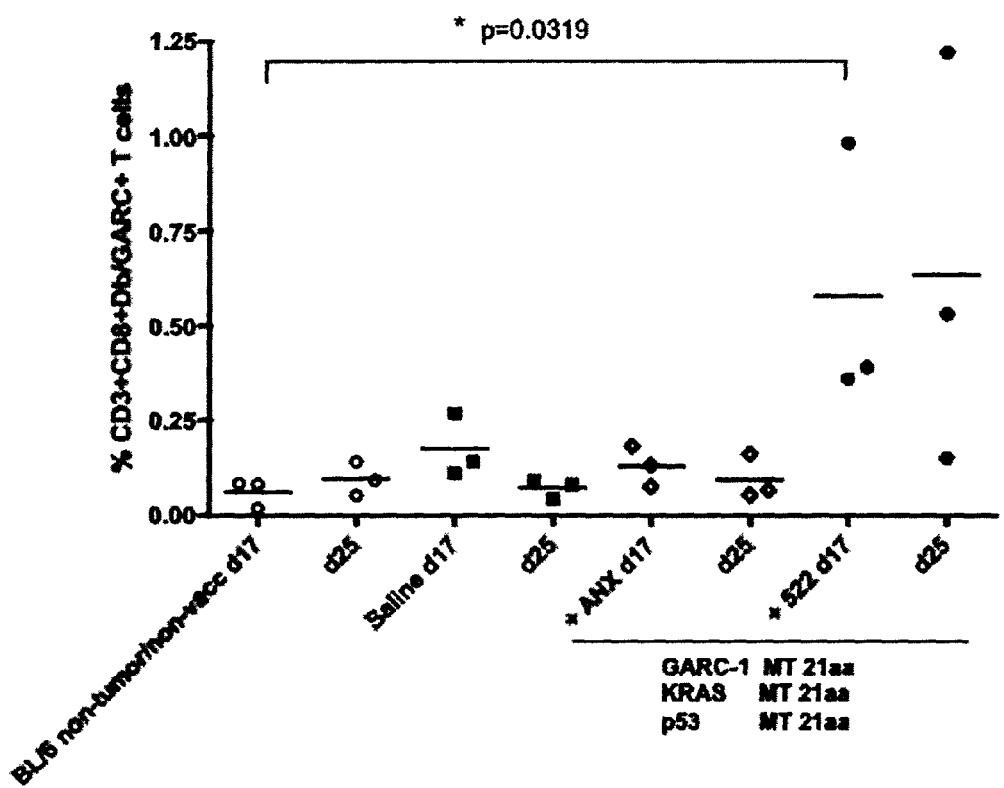
FIG. 32 shows results from Example 7.

Results are shown in FIG. 32.

EXAMPLE 8

Vaccination with New Adjuvant-Loaded GL261 on Mouse Brain Tumor Model

Figure 33:
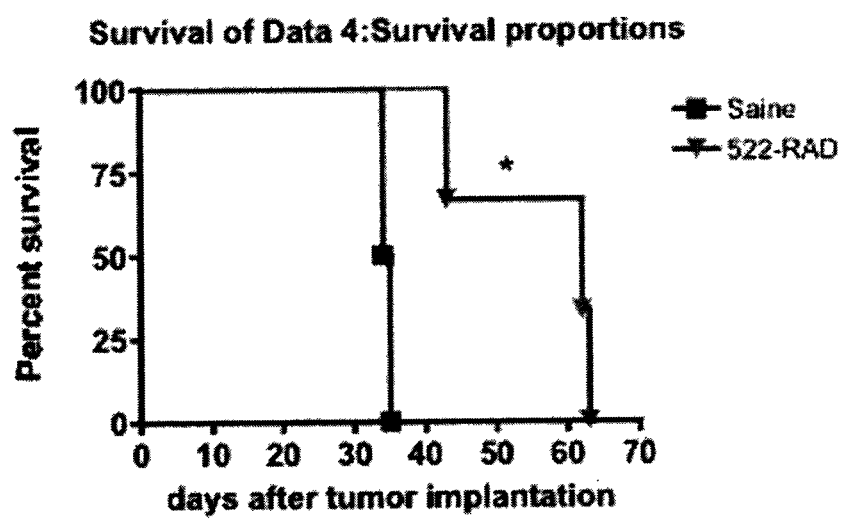
FIG. 33 shows results from Example 8.

Gl261-fluc cells were cultured at 5% oxygen, 5% $CO_2$ and 10% FBS DMEM and exposed to 45 uM of 522 for 24 hours and followed by 2 hours' before irradiated with X-RAD 320 Biological Irradiator (GE, Fairfield, Conn.) at 30Gy. Female C57BL/6 at the age of 6-8 weeks old were injected with 15000 of GL261-Fluc intracranially to establish tumors. For vaccination, 1 million of irradiated GL261, 522 loaded cells were injected subcutaneously into each inner side of thigh. Results for compound 522 are shown in FIG. 33.

EXAMPLE 9

TLR7/8-NF-κB Reporter Assay; and Measurement of Proimflammatory Cytokines with Cytometric Bead Assay TLR7/8-NF-κB Reporter Assay Human embryonic kidney (HEK) cells that were stably transfected with human TLR7 or TLR8 and an NF-κB—responsive secreted embryonic alkaline phosphatase (SEAP) gene (HEK-TLR7/8) were purchased from InvivoGen (San Diego, Calif.). The procedure used to measure TLR7 or TLR8 agonist activity was conducted as described by Hood et al. (Hood J. D, et al., *Human Vaccines*, 2010, 6, 4, 322-335). Briefly, HEK-TLR7/8 cells were stimulated with 3.3 or 30 µM of compound in a 96-well plate in DMEM containing 10% FBS and 0.01% Normocin (InvivoGen) for 24 hrs. Twenty microliters of the supernatant from each well was incubated with Quanti-blue substrate solution (InvivoGen) at 37° C. for 1 hour and absorbance was read at 650 nm using a Synergy plate reader (Biotek, Winooski, Vt.).

Measurement of Proimflammatory Cytokines with Cytometric Bead Assay

Bone marrow derived dendritic cells (BMDC) were generated by isolating a single cell suspension of marrow from the femur of C57BL/6 mice (6-8 weeks of age). Red blood cells were lysed with 0.83% NH4Cl, 0.1% KHCO3 and 0.009%. 5 million cells were seeded in each of well of a 6 well plate in complete RPMI media (Invitrogen, Grand Island, N.Y.), supplemented with mouse 20 ng/ml Granulocyte-Macrophage Colony Stimulating Factor (PeproTech, Rocky Hill, N.J.). After 6 days after culture, BMDC were stimulated with 3.3 or 30 µM of compound for 3 days. Twenty five microliters of supernatant was then removed and assayed for TNFα, IL-12p40, IL-1β and IL-10 using a flow cytometric bead array according to the manufacturers' instructions (BD Bioscience, San Jose, Calif.). Flow cytometry was performed on a FACS canto-II (BD Bioscience) and data were analyzed using Flowjo software (Tree Star, Inc. Ashland, Oreg.)

Data for representative compounds of the invention is provided in the following tables.

| Compound | $EC_{50}$ of TLR7(uM) (mean ± SD) | $EC_{50}$ of TLR8(uM) (mean ± SD) | TNF(pg/ml) (mean ± SD) |
|---|---|---|---|
| 527 | 2.60 ± 0.18 | 7.15 ± 0.29 | 2091.19 +± 72.51 |
| 528 | 2.93 ± 0.55 | 2.86 ± 0.32 | 1819.48 ± 110.76 |
| 529 | 22.95 ± 5.28 | 4.41 ± 0.49 | 1996.92 ± 58.42 |
| 531 | 5.23 ± 0.16 | 4.73 ± 0.55 | 1448.39 ± 74.42 |
| 520 | 2.42 ± 0.19 | 30.97 ± 10.59 | 2595.16 ± 458.09 |
| 522 | 3.31 ± 0.64 | 4.88 ± 0.27 | 1609.48 ± 217.08 |
| 533 | 4.38 ± 0.39 | 1.47 ± 0.20 | 1775.11 ± 88.03 |
| 521 | 5.67 ± 0.81 | N/A | 1513.71 ± 148.88 |
| 421 | NO $EC_{50}$ | N/A | 1450.58 ± 137.02 |
| 530 | 2.50 ± 0.15 | 5.82 ± 0.20 | 1783.27 ± 318.85 |
| 420 | 1.52 ± 0.07 | 49.62 ± 1.02 | 1353.00 ± 552.00 |
| 535 | 4.79 ± 0.46 | N/A | 1199.42 ± 42.18 |
| 525 | 2.21 ± 0.44 | 19.85 ± 1.04 | 1288.25 ± 37.76 |
| 536 | 20.23 ± 4.11 | 31.67 ± 1.54 | 1693.66 ± 89.85 |
| 526 | 3.94 ± 0.25 | 17.24 ± 5.33 | 2046.83 ± 236.04 |
| 504 | 21.21 ± 5.22 | 21.23 ± 19.95 | 69.99 ± 8.76 |
| 516 | 49.16 ± 17.27 | N/A | 862.12 ± 234.54 |
| 518 | 23.83 ± 4.34 | N/A | 1850.23 ± 253.34 |
| 511 | 7.92 ± 1.49 | N/A | 100.90 ± 10.80 |
| 503 | N/A | N/A | 80.86 ± 18.63 |
| 517 | 29.12 ± 4.33 | N/A | 1610.66 ± 139.49 |
| 412 | N/A | N/A | 92.69 ± 13.99 |

-continued

| Compound | EC$_{50}$ of TLR7(uM) (mean ± SD) | EC$_{50}$ of TLR8(uM) (mean ± SD) | TNF(pg/ml) (mean ± SD) |
|---|---|---|---|
| 523 | N/A | N/A | 112.62 ± 11.34 |
| 422 | NO EC50 | N/A | 651.83 ± 51.38 |

| Compound | IL-12/23p40(pg/ml) (mean ± SD) | IL-1 beta(pg/ml) (mean ± SD) | IL-10(pg/ml) (mean ± SD) |
|---|---|---|---|
| 527 | 3707.68 ± 205.49 | 5577.00 ± 501.21 | 252.19 ± .96 |
| 528 | 10077.99 ± 1791.65 | 3569.42 ± 503.92 | 188.28 ± 6.45 |
| 529 | 8527.52 ± 888.86 | 3292.19 ± 332.52 | 133.54 ± 9.28 |
| 531 | 5680.99 ± 460.85 | 2913.93 ± 577.65 | 155.18 ± 2.59 |
| 520 | 2123.48 ± 306.06 | 2566.80 ± 421.14 | 272.43 ± 44.67 |
| 522 | 7363.64 ± 963.38 | 2269.43 ± 161.33 | 129.39 ± 1.55 |
| 533 | 4990.28 ± 404.59 | 2160.95 ± 146.15 | 148.30 ± 13.47 |
| 521 | 5216.38 ± 502.74 | 1534.39 ± 122.23 | 164.57 ± 9.76 |
| 421 | 1773.41 ± 62.13 | 1143.84 ± 116.25 | 93.95 ± 14.00 |
| 530 | 10606.12 ± 1562.79 | 1093.52 ± 178.27 | 183.69 ± 21.61 |
| 420 | 1285.91 ± 276.04 | 893.44 ± 306.08 | 109.73 ± 43.93 |
| 535 | 2466.60 ± 52.79 | 857.42 ± 48.67 | 113.48 ± 0.66 |
| 525 | 3747.45 ± 124.69 | 830.83 ± 198.90 | 146.73 ± 6.33 |
| 536 | 2295.82 ± 487.97 | 698.60 ± 143.52 | 216.94 ± 33.35 |
| 526 | 2588.84 ± 209.78 | 396.91 ± 16.96 | 273.69 ± 44.70 |
| 504 | 954.26 ± 39.16 | 237.25 ± 52.53 | 17.44 ± 3.57 |
| 516 | 348.04 ± 19.95 | 180.11 ± 124.72 | 69.38 ± 27.87 |
| 518 | 1302.95 ± 132.18 | 93.64 ± 6.57 | 70.67 ± 9.89 |
| 511 | 470.78 ± 63.50 | 46.52 ± 1.64 | 15.65 ± 5.36 |
| 503 | 50.47 ± 8.65 | 44.36 ± 4.40 | 12.75 ± 3.23 |
| 517 | 794.26 ± 275.63 | 38.51 ± 2.23 | 44.54 ± 1.62 |
| 412 | 334.188 ± 32.33 | 32.42 ± 2.24 | 18.01 ± 4.37 |
| 523 | 188.56 ± 91.72 | 30.35 ± 2.81 | 7.59 ± 1.38 |
| 422 | 31.22 ± 6.91 | 12.82 ± 3.75 | 15.72 ± 0.93 |

EXAMPLE 10

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

[chemical structure of formula I showing tricyclic imidazoquinoline with substituents $NR_aR_b$, $R_2$, $R_1$, $R_3$ and ring positions 2, 6, 7, 8, 9]

wherein:
- $R_1$ is $R^k$—O—C(=O)—;
- $R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl optionally substituted with one or more hydroxy, —SH, halo, oxiranyl, $(C_3-C_8)$cycloalkyl, aryl, $(C_1-C_6)$alkoxy, $(C_1-C_6)$alkylthio, or $NR^gR^h$;
- $R_3$ is $(C_1-C_6)$alkyl, optionally substituted with one or more hydroxy, $(C_1-C_6)$alkoxy, aryl, aryl$(C_1-C_6)$alkoxy or oxiranyl;
- $R_a$ is H or $(C_1-C_6)$alkyl;
- $R_b$ is H or X—Y;
- $R^g$ and $R^h$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;
- $R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;
- $R^m$ and $R^n$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;
- X is a linking group; and
- Y is an antigen or maleimide;

wherein the tricyclic ring structure in formula I can optionally be further substituted on one or more carbons with one or more groups independently selected from halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and $R^p$ and $R^q$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;

or a salt thereof.

2. The compound of claim 1 wherein:
- $R_1$ is $R^k$—O—C(=O)—;
- $R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl, optionally substituted with one or more hydroxy, —SH, halo, oxiranyl, $(C_3-C_8)$cycloalkyl, aryl, $(C_1-C_6)$alkoxy, $(C_1-C_6)$alkylthio, or $NR^gR^h$;
- $R_3$ is $(C_1-C_6)$alkyl, optionally substituted with one or more hydroxy, aryl, or oxiranyl;
- $R_a$ is H or $(C_1-C_6)$alkyl;
- $R_b$ is H or X—Y;
- $R^g$ and $R^h$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;
- $R^k$ is H, $(C_1-C_6)$alkyl, $(C_2-C_6)$alkenyl, $(C_2-C_6)$alkynyl, $(C_3-C_8)$cycloalkyl, trifluoromethyl, aryl, or aryl$(C_1-C_6)$alkyl, wherein each $(C_1-C_6)$alkyl can optionally be substituted with one or more halo, $(C_1-C_6)$alkanoyloxy, $(C_1-C_6)$alkoxy, $(C_3-C_8)$cycloalkyl;
- $R^m$ and $R^n$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl;
- X is a linking group; and
- Y is an antigen or maleimide;

wherein the tricyclic ring structure in formula I can optionally be further substituted on one or more carbons with one or more groups independently selected from halo, hydroxy, nitro, $(C_1-C_6)$alkyl, $(C_1-C_6)$alkenyl, $(C_1-C_6)$alkynyl, $(C_1-C_6)$alkoxy, $(C_1-C_6)$alkanoyl, $(C_1-C_6)$alkanoyloxy, $(C_1-C_6)$alkoxycarbonyl, trifluoromethyl, trifluoromethoxy, cyano, and $NR^pR^q$; and $R^p$ and $R^q$ are each independently H or $(C_1-C_6)$alkyl; or taken together with the nitrogen to which they are attached form a aziridino, azetidino, morpholino, piperazino, pyrrolidino or piperidino ring, which ring may optionally be substituted with one or more $(C_1-C_6)$alkyl.

3. The compound of claim 1 wherein $R_2$ is H, $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl, optionally substituted with one or more hydroxy, halo, oxiranyl, $(C_3-C_8)$cycloalkyl, aryl, $(C_1-C_6)$alkoxy, or $NR^gR^h$.

4. The compound of claim 1 wherein $R_1$ is methoxycarbonyl, ethoxycarbonyl, isopropoxycarbonyl, benzyloxycarbonyl, or butoxycarbonyl.

5. The compound of claim 1 wherein $R_2$ is $NR^gR^h$, $(C_1-C_6)$alkanoyl, $(C_1-C_6)$alkoxycarbonyl, $(C_1-C_6)$alkanoyloxy, $R^mR^nNC(=O)$—, or $(C_1-C_6)$alkyl, optionally substituted with one or more hydroxy, halo, oxiranyl, $(C_3-C_8)$cycloalkyl, aryl, $(C_1-C_6)$alkoxy, oxiranyl, or $NR^gR^h$.

6. The compound of claim 1 wherein $R_2$ is $(C_1-C_6)$alkyl, optionally substituted with one or more hydroxy, halo, oxiranyl, $(C_3-C_8)$cycloalkyl, aryl, $(C_1-C_6)$alkoxy, oxiranyl, or $NR^gR^h$.

7. The compound of claim 1 wherein $R_2$ is $(C_1-C_6)$alkyl, optionally substituted with one or more hydroxy, oxiranyl, or $(C_1-C_6)$alkoxy.

8. The compound of claim 1 wherein $R_2$ is $(C_1-C_6)$alkyl, substituted with one or more hydroxy.

9. The compound of claim 1 wherein $R_2$ is H, methyl, ethyl, propyl, butyl, or pentyl.

10. The compound of claim 1 wherein $R_3$ is $(C_1-C_6)$alkyl, substituted with one or more hydroxy.

11. The compound of claim 1 wherein $R_3$ is isobutyl, benzyl, 2-hydroxy-2-methylpropyl, 2-hydroxypropyl, 2-hydroxyethyl, 2-methoxyethyl, or 2-benzyloxyethyl.

12. The compound of claim 1 wherein $R_b$ is H.

13. The compound of claim 1 wherein $R_b$ is X—Y.

14. The compound of claim 13 wherein X is $(C_1-C_6)$alkyl, $(C_2-C_6)$alkenyl, or $(C_1-C_6)$alkynyl, which $(C_1-C_6)$alkyl, $(C_2-C_6)$alkenyl, or $(C_1-C_6)$alkynyl is optionally substituted with oxo.

15. The compound of claim 13 wherein X is:

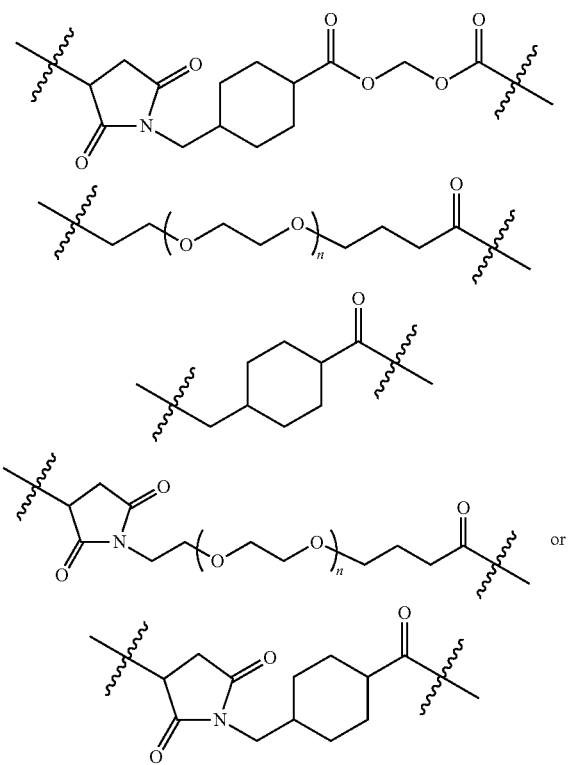

and n is 2, 3, 4, 5, or 6.

16. The compound of claim 13 wherein Y is maleimide.

17. The compound of claim 13 wherein Y is an antigen associated with a bacteria or virus.

18. The compound of claim 1 wherein the compound of formula (I) is a compound of formula (Ib):

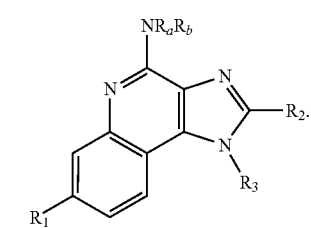

19. The compound of claim 1 wherein the compound of formula (I) is a compound of formula (Ic):

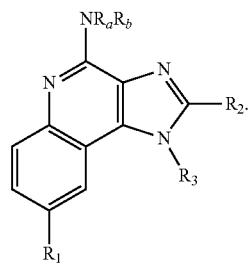

20. The compound of claim 1 wherein the compound of formula (I) is a compound of formula (Id):

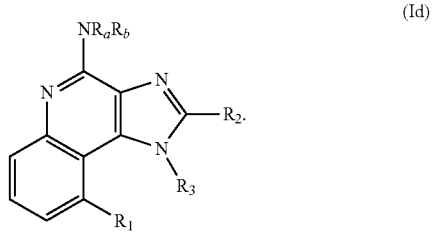

21. A compound selected from:

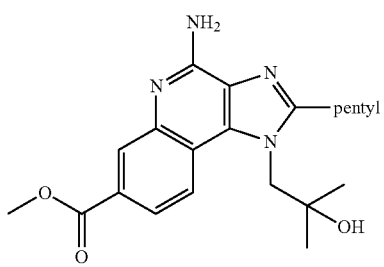

527

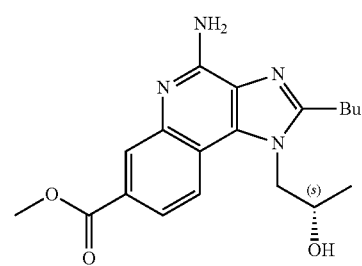

528

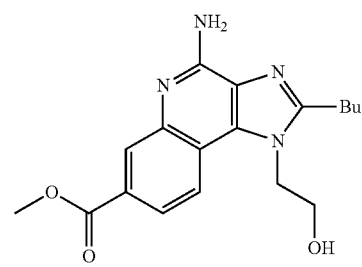

529

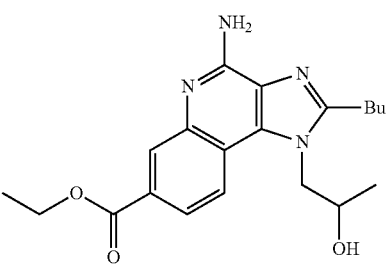

531

| 520 | 420 |
|---|---|
| 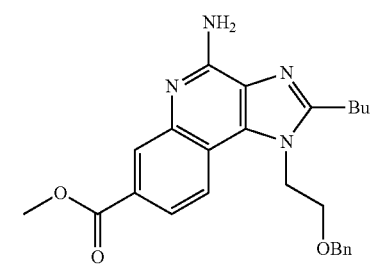 | 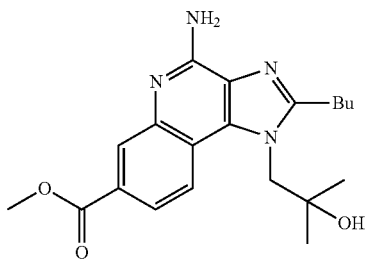 |
| 522 | 535 |
| 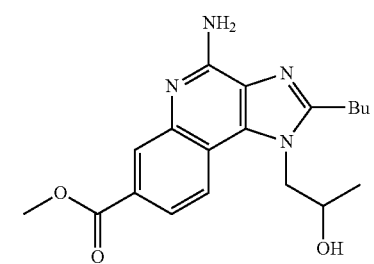 | 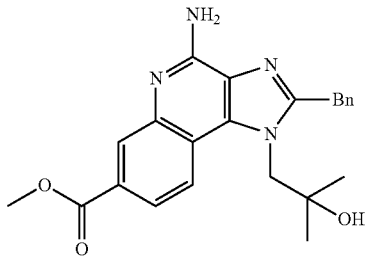 |
| 533 | 525 |
| 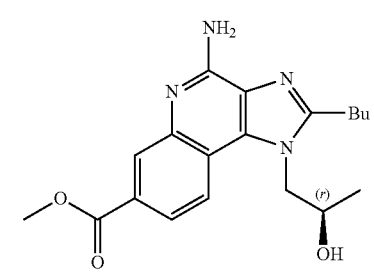 | 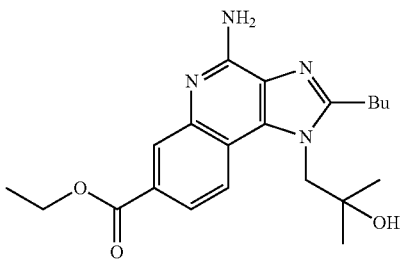 |
| 521 | 536 |
| 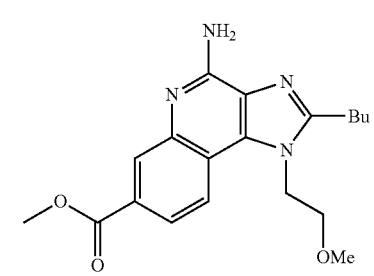 | 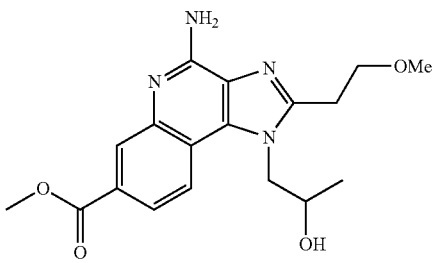 |
| 421 | 526 |
| 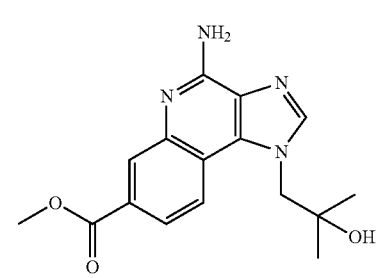 | 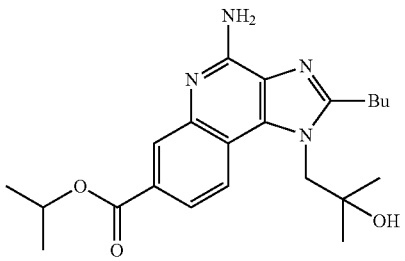 |
| 530 | 504 |
| 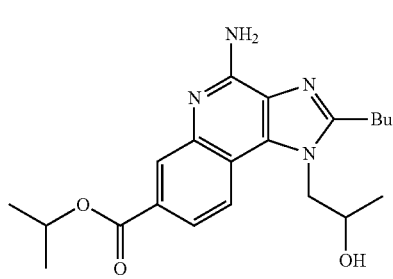 | 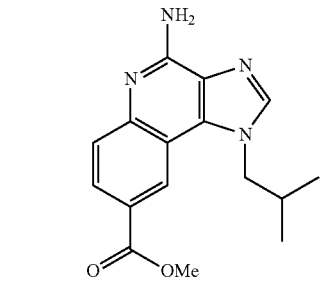 |

-continued

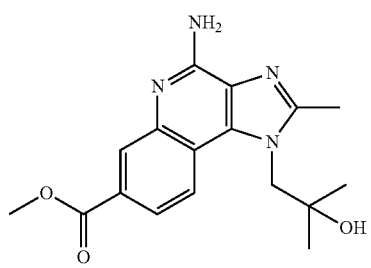 516

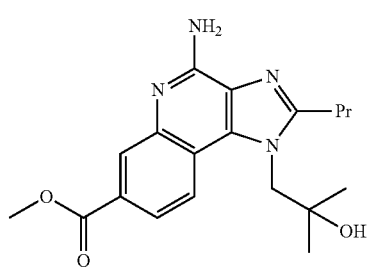 518

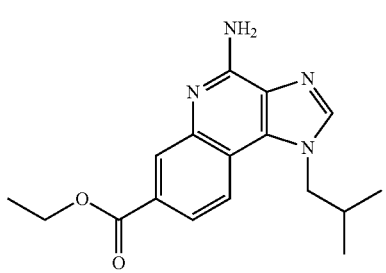 511

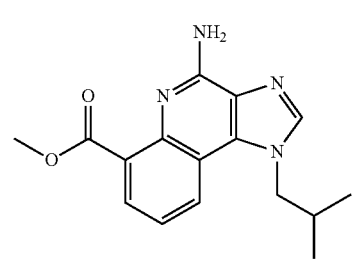 503

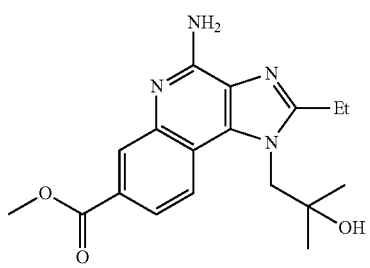 517

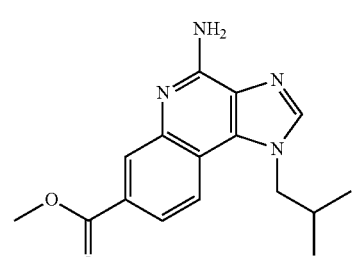 412

-continued

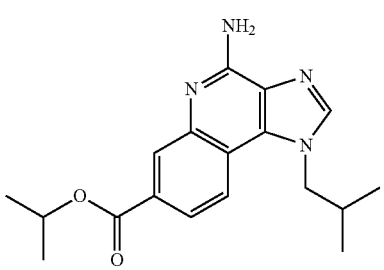 523

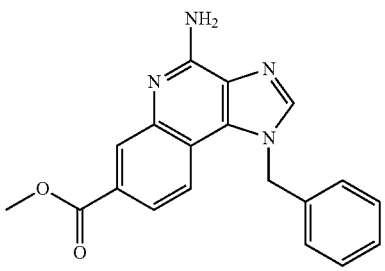 514

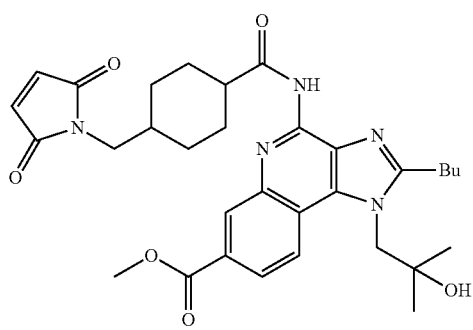 550

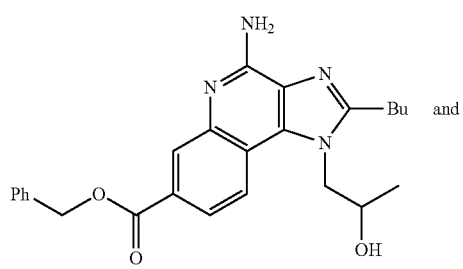 538

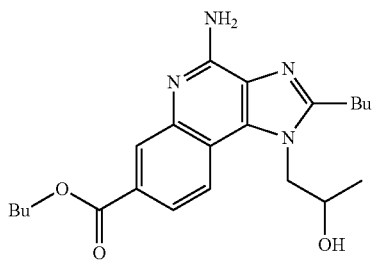 540 and salts thereof.

22. A pharmaceutical composition comprising a compound of formula I, or a pharmaceutically acceptable salt thereof, as described in claim 1, and a pharmaceutically acceptable diluent or carrier.

23. A method for stimulating an immune response in an animal comprising administering a compound of formula I, or a pharmaceutically acceptable salt thereof, as described in claim 1, to the animal.

24. A method for treating cancer in an animal comprising administering a compound of formula I, or a pharmaceutically acceptable salt thereof, as described in claim 1, to the animal.

25. The compound of claim 13 wherein Y is an antigen associated with an influenza, HIV, or HCV.

26. The compound of claim 13 wherein Y is an antigen associated with a tumor cell or a tumor cell lysate.

* * * * *